(12) United States Patent
Haley et al.

(10) Patent No.: US 7,425,638 B2
(45) Date of Patent: Sep. 16, 2008

(54) CIS-IMIDAZOLINES

(75) Inventors: Gregory Jay Haley, San Diego, CA (US); Norman Kong, West Caldwell, NJ (US); Emily Aijun Liu, Nutley, NJ (US); Klaus B. Simonsen, San Diego, CA (US); Binh Thanh Vu, North Caldwell, NJ (US); Stephen Evan Webber, San Diego, CA (US)

(73) Assignee: Hoffmann-La Roche Inc., Nutley, NJ (US)

( * ) Notice: Subject to any disclaimer, the term of this patent is extended or adjusted under 35 U.S.C. 154(b) by 224 days.

(21) Appl. No.: 10/867,154

(22) Filed: Jun. 14, 2004

(65) Prior Publication Data

US 2004/0259884 A1 Dec. 23, 2004

Related U.S. Application Data

(60) Provisional application No. 60/479,351, filed on Jun. 17, 2003, provisional application No. 60/566,528, filed on Apr. 29, 2004, provisional application No. 60/573,900, filed on May 24, 2004.

(51) Int. Cl.
  *C07D 233/22* (2006.01)
  *C07D 401/06* (2006.01)
(52) U.S. Cl. ............... 548/334.1; 514/396; 514/397
(58) Field of Classification Search ........... 548/334.1
  See application file for complete search history.

(56) References Cited

U.S. PATENT DOCUMENTS 6,734,302 B2 * 5/2004 Kong et al. ............... 544/139

FOREIGN PATENT DOCUMENTS

| EP | 363 061 | 4/1990 |
|---|---|---|
| EP | 0 433 682 A2 | 6/1991 |
| WO | WO 92/03421 | 3/1992 |
| WO | WO 00/78725 | 12/2000 |
| WO | WO 02/20017 A2 | 3/2002 |
| WO | WO 03/051359 A1 | 6/2003 |

OTHER PUBLICATIONS

Seung Hoon Cheon et al, Archives of Pharmacal Research, XP009036613,vol. 20, No. 2, pp. 138-143 (1997).

* cited by examiner

*Primary Examiner*—Laura L. Stockton
(74) *Attorney, Agent, or Firm*—George W. Johnston; Patricia S. Rocha-Tramaloni; David E. Wildman

(57) ABSTRACT

The present invention provides compounds according to formula I

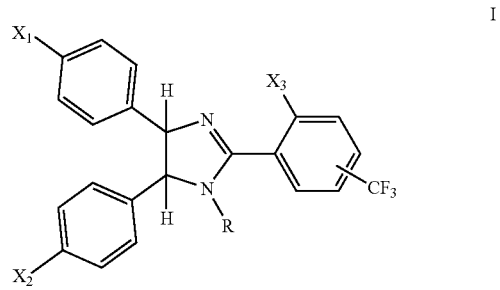

having the designations provided herein, and pharmaceutically acceptable salts and esters thereof. These compounds inhibit the interaction of MDM2 protein with a p53-like peptide and have antiproliferative activity.

5 Claims, No Drawings

CIS-IMIDAZOLINES

PRIORITY TO RELATED APPLICATIONS

This application claims the benefit of Provisional Application(s) Ser. No. 60/479,351, filed Jun. 17, 2003, Ser. No. 60/566,528 filed Apr. 29, 2004 and Ser. No. 60/573,900 filed May 24, 2004.

FIELD OF THE INVENTION

This invention is related to at least one compound selected from a compound of formula I

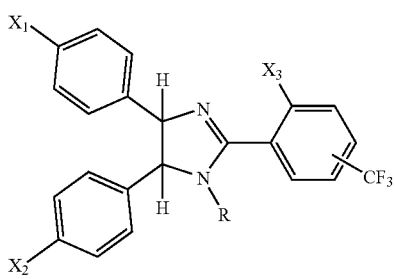

or pharmaceutically acceptable salts thereof, wherein $X_1$, $X_2$, $X_3$, and R are described in this application. This compound is believed to inhibit the interaction of MDM2 protein with a p-53-like peptide and have anti-proliferative activity.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

Wells et al. *J. Org. Chem.*, 1972, 37, 2158-2161, report synthesis of imidazolines. Hunter et al., *Can. J. Chem.*, 1972, Vol. 50, pgs. 669-77, report the preparation of amarine and isoamarine compounds which had previously been studied for chemiluminescence (McCapra et al. *Photochem. and Photobiol.* 1965, 4, 1111-1121). Zupanc et al. *Bull. Soc. Chem. & Tech.* (Yugoslavia) 1980-81, 27/28, 71-80, report the use of triaryl imidazolines as starting materials in the preparation of EDTA derivatives. EP 363 061 to Matsumoto reports imidazoline derivatives useful as immunomodulators. The compounds were indicated to have low toxicity. Treatment and/or prevention of rheumatoid arthritis, multiple sclerosis, systemic lupus, erythemathodes, and rheumatic fever were implicated. WO 00/78725 to Choueiry et al. report a method for making substituted amidine compounds, and indicate that imidazoline-type compounds may be useful in the treatment of diabetes or related diseases involving impaired glucose disposal.

SUMMARY OF THE INVENTION

The present invention provides at least one compound selected from a compound of formula I

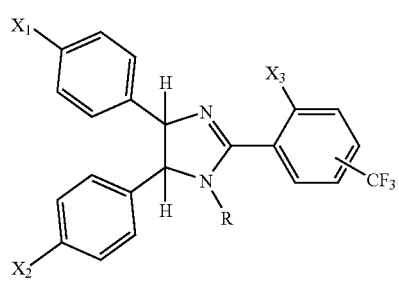

wherein
$X_1$ and $X_2$ are halogen;
$X_3$ is lower alkoxy;
R is selected from the group consisting of

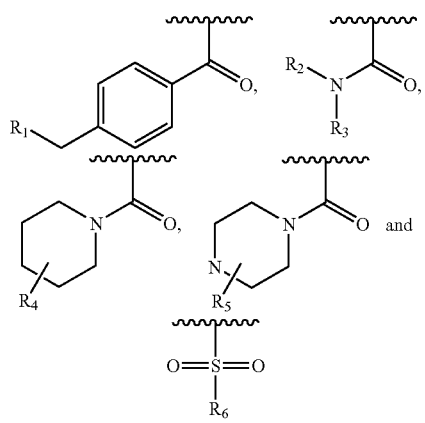

wherein
$R_1$ is selected from the group consisting of
  N-lower alkyl,
  unsubstituted heterocycle and
  heterocycle substituted by one or more substituents
    selected from the group consisting of $NH_2$, NH—C(O)- lower alkyl, C(O)-lower alkyl, C(O)-lower alkoxy, oxo, heterocycle, and lower alkyl substituted by hydroxy;

$R_2$ is selected from hydrogen, methyl and lower alkoxy;

$R_3$ is selected from the group consisting of
- heteroaryl,
- heterocycle,
- lower alkyl substituted with $R_7$,
- aryl,
- lower alkoxy, and
- lower alkyl;

$R_4$ is selected from the group consisting of one or more of
- C(O)-lower alkoxy,
- lower alkoxy,
- $CH_2$—N-lower alkyl,
- $CH_2$-heterocycle,
- $CH_2$-heterocycle substituted by oxo,
- aryl,
- NH—C(S)—N-lower alkyl,
- NH—C(S)—N-aryl,
- NH—C(O)—$R_8$,
- N-alkyl substituted by C(O)—$R_{16}$, and
- trifluoromethyl;

$R_5$ is selected from the group consisting of one or more of
- oxo,
- heteroaryl,
- aryl substituted by a substituent selected from lower alkoxy and fluoro,
- C(S)—N-lower alkyl,
- C(S)—N-aryl,
- C(O)—$CH_2$—$R_{12}$,
- C(O)—$R_{13}$,
- $SO_2$—$R_{14}$ and
- lower alkyl substituted by a substituent selected from $R_{15}$ and C(O)—$R_{16}$;

$R_6$ is selected from the group consisting of
- lower alkyl substituted by —N-lower alkyl,
- lower alkyl substituted by heterocycle,
- lower alkyl substituted by heterocycle substituted by one or two substituents
- selected from lower alkyl, lower alkyl substituted by hydroxyl lower alkyl substituted by lower alkoxy, and oxo;

$R_7$ is selected from the group consisting of
- cyano,
- hydroxy,
- lower alkoxy,
- heteroaryl,
- heterocycle,
- heterocycle substituted by oxo,
- N-lower alkyl; and
- aryl substituted by a substituent selected from the group consisting of $SO_2NH_2$, lower alkoxy and hydroxy;

$R_8$ is selected from the group consisting of
- N-lower alkyl,
- heterocycle,
- heterocycle substituted by a substituent selected from the group consisting of oxo, C(O)—$NH_2$ and C(O)—NH-lower alkyl,
- $CH_2$—$R_9$ and
- $CH_2$—$R_{10}$;

$R_9$ is selected from the group consisting of
- $NH_2$,
- N-lower alkyl,
- N-lower alkyl substituted by a substituent selected from hydroxy and lower alkoxy,
- C(O)—NH-lower alkoxy,
- C(O)—NH-benzyloxy,
- C(O)-heterocycle substituted by a substituent selected from trifluoromethyl or hydroxy and
- C(O)—NH—$R_{11}$;

$R_{10}$ is selected from a
- heterocycle, and
- heterocycle substituted by one or more groups selected from the group consisting of C(O)-lower alkyl, C(O)—$NH_2$, C(O)—N-lower alkyl, lower alkyl substituted by hydroxy, hydroxy, lower alkoxy and oxo;

$R_{11}$ is selected from
- lower alkyl, and
- lower alkyl substituted by a substituent selected from the group consisting of alkoxy, heteroaryl substituted by lower alkyl, cyano, and trifluoromethyl;

$R_{12}$ is selected from the group consisting of
- lower alkoxy,
- $NH_2$,
- N-lower alkyl,
- N-lower alkyl substituted by a substituent selected from hydroxy and lower alkoxy,
- heteroaryl, and
- heterocycle substituted by $R_{17}$;

$R_{13}$ is selected from the group consisting of
- heteroaryl,
- heteroaryl substituted by one or two substituents selected from the group consisting of lower alkyl, aryl and halogen,
- heterocycle,
- heterocycle substituted by one or more substituents selected from the group consisting of lower alkyl, aryl and halogen,
- C(O)-lower alkyl,
- C(O)—$NH_2$,
- C(O)—N-lower alkyl,
- oxo, and
- lower alkyl substituted with —OC(O)$CH_3$;

$R_{14}$ is selected from the group consisting of
- trifluoromethyl,
- lower alkyl,
- aryl substituted by lower alkyl,
- $NH_2$,
- N-lower alkyl,
- N-lower alkyl substituted by a substituent selected from lower alkoxy, cyano, amino and trifluoromethyl;
- heteroaryl,
- heteroaryl substituted by a substituent selected from the group consisting of amino, halogen, hydroxy, oxo, C(O)-lower alkoxy, lower alkyl and lower alkyl substituted by hydroxyl,
- heterocycle and
- heterocycle substituted by a substituent selected from the group consisting of halogen, hydroxy, oxo, C(O)-lower alkoxy, lower alkyl and lower alkyl substituted by hydroxyl;

$R_{15}$ is selected from the group consisting of
- lower alkoxy,
- cyano,
- trifluoromethyl, hydroxyl,
- N-lower alkyl,
- $SO_2$-lower alkyl,
- C(O)-lower alkyl,
- $SO_2$—$NH_2$,
- $SO_2$—N-lower alkyl,
- heteroaryl and
- heterocycle;

$R_{16}$ is selected from the group consisting of
- lower alkoxy,
- $NH_2$,
- N-lower alkyl, N-lower alkoxy,
N-lower alkenyl,
N-benzyloxy,
N-lower alkyl substituted by $R_{18}$,
heterocycle and
heterocycle substituted by one or two substituents selected from the group consisting of hydroxy, alkoxy, trifluoromethyl, C(O)-lower alkyl, C(O)—NH$_2$, C(O)—N-lower alkyl, lower alkyl substituted by hydroxy and oxo;

$R_{17}$ is selected from the group consisting of
C(O)-lower alkyl,
C(O)—NH$_2$,
C(O)—N-lower alkyl,
hydroxy,
oxo and
lower alkyl substituted by hydroxy; and $R_{18}$ is selected from the group consisting of
lower alkoxy,
cyano,
trifluoromethyl,
heterocycle and
hydroxyl;

or a pharmaceutically acceptable salt or ester thereof.

In preferred embodiments, the two hydrogen of the imadazoline ring are in a cis configuration to each other. The compound may be in a racemic form and may be optically active. The compound may be an isomer.

DETAILED DESCRIPTION OF THE INVENTION

The present invention provides cis-imidazolines which are small molecule inhibitors of the MDM2-p53 interaction. In cell-free and cell-based assays, compounds of the present invention are shown to inhibit the interaction of MDM2 protein with a p53-like peptide with a potency that is approximately 100 fold greater than a p53-derived peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

The present invention provides at least one compound selected from a compound selected from a compound of formula I

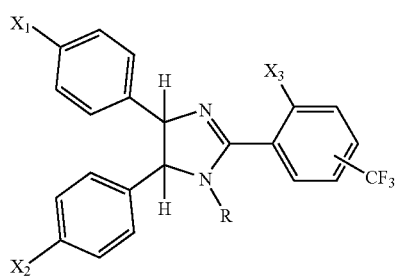

wherein
$X_1$ and $X_2$ are halogen;
$X_3$ is lower alkoxy;

R is selected from the group consisting of

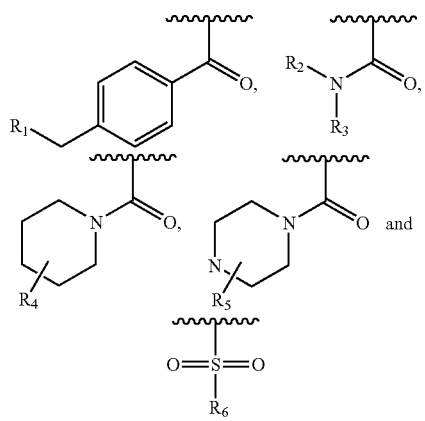

wherein
$R_1$ is selected from the group consisting of
N-lower alkyl,
unsubstituted heterocycle and
heterocycle substituted by one or more substituents selected from the group consisting of NH$_2$, NH—C(O)-lower alkyl, C(O)-lower alkyl, C(O)-lower alkoxy, oxo, heterocycle, and lower alkyl substituted by hydroxy;

$R_2$ is selected from hydrogen, methyl and lower alkoxy;

$R_3$ is selected from the group consisting of
heteroaryl,
heterocycle,
lower alkyl substituted with $R_7$;
aryl,
lower alkoxy, and
lower alkyl;

$R_4$ is selected from the group consisting of one or more of
C(O)-lower alkoxy,
lower alkoxy,
CH$_2$—N-lower alkyl,
CH$_2$-heterocycle,
CH$_2$-heterocycle substituted by oxo,
aryl,
NH—C(S)—N-lower alkyl,
NH—C(S)—N-aryl,
NH—C(O)—R$_8$;
N-alkyl substituted by C(O)R$_{16}$, and
trifluoromethyl;

$R_5$ is selected from the group consisting of one or more of
oxo,
heteroaryl,
aryl substituted by a substituent selected from lower alkoxy and fluoro,
C(S)—N-lower alkyl,
C(S)—N-aryl,
C(O)—CH$_2$—R$_{12}$,
C(O)—R$_{13}$,
SO$_2$—R$_{14}$ and
lower alkyl substituted by a substituent selected from $R_{15}$ and C(O)—R$_{16}$;

$R_6$ is selected from the group consisting of
lower alkyl substituted by —N-lower alkyl,
lower alkyl substituted by heterocycle,
lower alkyl substituted by heterocycle substituted by one or two substituents selected from lower alkyl, lower alkyl substituted by hydroxyl lower alkyl substituted by lower alkoxy, and oxo;

$R_7$ is selected from the group consisting of
cyano,
hydroxy,
lower alkoxy,
heteroaryl,
heterocycle,
heterocycle substituted by oxo,
N-lower alkyl; and
aryl substituted by a substituent selected from the group consisting of $SO_2NH_2$, lower alkoxy and hydroxy;

$R_8$ is selected from the group consisting of
N-lower alkyl,
heterocycle,
heterocycle substituted by a substituent selected from the group consisting of oxo, $C(O)$—$NH_2$ and $C(O)$—NH-lower alkyl,
$CH_2$—$R_9$ and
$CH_2$—$R_{10}$;

$R_9$ is selected from the group consisting of
$NH_2$,
N-lower alkyl,
N-lower alkyl substituted by a substituent selected from hydroxy and lower alkoxy,
$C(O)$—NH-lower alkoxy,
$C(O)$—NH-benzyloxy,
$C(O)$-heterocycle substituted by a substituent selected from trifluoromethyl or hydroxy and
$C(O)$—NH—$R_{11}$;

$R_{10}$ is selected from a
heterocycle, and
heterocycle substituted by one or more groups selected from the group consisting of $C(O)$-lower alkyl, $C(O)$—$NH_2$, $C(O)$—N-lower alkyl, lower alkyl substituted by hydroxy, hydroxy, lower alkoxy and oxo;

$R_{11}$ is selected from
lower alkyl, and
lower alkyl substituted by a substituent selected from the group consisting of alkoxy, heteroaryl substituted by lower alkyl, cyano, and trifluoromethyl;

$R_{12}$ is selected from the group consisting of
lower alkoxy,
$NH_2$,
N-lower alkyl,
N-lower alkyl substituted by a substituent selected from hydroxy and lower alkoxy,
heteroaryl, and
heterocycle substituted by $R_{17}$;

$R_{13}$ is selected from the group consisting of
heteroaryl,
heteroaryl substituted by one or two substituents selected from the group consisting of lower alkyl, aryl and halogen,
heterocycle,
heterocycle substituted by one or more substituents selected from the group consisting of lower alkyl, aryl and halogen,
$C(O)$-lower alkyl,
$C(O)$—$NH_2$,
$C(O)$—N-lower alkyl, and
oxo;
lower alkyl substituted with —$OC(O)CH_3$;

$R_{14}$ is selected from the group consisting of
trifluoromethyl,
lower alkyl,
aryl substituted by lower alkyl,
$NH_2$,
N-lower alkyl,
N-lower alkyl substituted by a substituent selected from lower alkoxy, cyano, amino and trifluoromethyl,
heteroaryl,
heteroaryl substituted by a substituent selected from the group consisting of amino, halogen, hydroxy, oxo, $C(O)$-lower alkoxy, lower alkyl and lower alkyl substituted by hydroxyl,
heterocycle and
heterocycle substituted by a substituent selected from the group consisting of halogen, hydroxy, oxo, $C(O)$-lower alkoxy, lower alkyl and lower alkyl substituted by hydroxyl;

$R_{15}$ is selected from the group consisting of
lower alkoxy,
cyano,
trifluoromethyl, hydroxyl,
N-lower alkyl,
$SO_2$-lower alkyl,
$C(O)$-lower alkyl,
$SO_2$—$NH_2$,
$SO_2$—N-lower alkyl,
heteroaryl and
heterocycle;

$R_{16}$ is selected from the group consisting of
lower alkoxy,
$NH_2$,
N-lower alkyl,
N-lower alkoxy,
N-lower alkenyl,
N-benzyloxy,
N-lower alkyl substituted by $R_{18}$,
heterocycle and
heterocycle substituted by one or two substituents selected from the group consisting of hydroxy, alkoxy, trifluoromethyl, $C(O)$-lower alkyl, $C(O)$—$NH_2$, $C(O)$—N-lower alkyl, lower alkyl substituted by hydroxy and oxo;

$R_{17}$ is selected from the group consisting of
$C(O)$-lower alkyl,
$C(O)$—$NH_2$,
$C(O)$—N-lower alkyl,
hydroxy,
oxo and
lower alkyl substituted by hydroxy; and $R_{18}$ is selected from the group consisting of
lower alkoxy,
cyano,
trifluoromethyl,
heterocycle and
hydroxyl;

or a pharmaceutically acceptable salt or ester thereof.

In preferred embodiments, the two hydrogen of the imadazoline ring are in a cis configuration to each other. The compound may be in racemic form and may be optically active. The compound may be an isomer.

In another preferred embodiment, $X_1$ and $X_2$ are both chloro; $X_3$ is ethoxy or isopropoxy.

In another preferred embodiment, the trifluoromethyl group is para to the imidazoline ring. The trifluoromethyl group is meta to the imidazoline ring.

The R group is preferred to be $C(O)$-phenyl-$CH_2$—$R_1$, $C(O)$—$NR_2R_3$, $C(O)$-piperidine substituted by $R_4$, and $C(O)$-piperazine substituted by $R_5$, $SO_2$—$R_6$.

In a further preferred embodiment, $X_1$ and $X_2$ are chloro, $X_3$ is ethoxy or isopropoxy, the trifluoromethyl group is para to the imidazoline ring, and R is C(O)-piperidine substituted by $R_4$.

In yet another preferred embodiment, $X_1$ and $X_2$ are chloro, $X_3$ is ethoxy or isopropoxy, the trifluoromethyl group is para to the imidazoline ring, and R is C(O)-piperazine substituted by $R_5$.

In yet another preferred embodiment, $X_1$ and $X_2$ are chloro, $X_3$ is ethoxy or isopropoxy, the trifluoromethyl group is meta to the imidazoline ring, and R is C(O)-piperidine substituted by $R_4$.

In yet another preferred embodiment, $X_1$ and $X_2$ are chloro, $X_3$ is ethoxy or isopropoxy, the trifluoromethyl group is meta to the imidazoline ring, and R is C(O)-piperazine substituted by $R_5$.

In a further preferred embodiment, $R_5$ is lower alkyl substituted by $R_{15}$.

In yet another preferred embodiment, piperazine is substituted by oxo and lower alkyl substituted by $R_{15}$.

In yet another preferred embodiment, $R_{15}$ is selected from the group consisting of —$SO_2$-methyl, hydroxy and lower alkoxy.

"Alkoxy" denotes —O-alkyl.

"Alkyl" denotes a straight-chained or branched saturated aliphatic hydrocarbon. "Lower alkyl" groups denote C1-C6 alkyl groups and include methyl, ethyl, propyl, isopropyl, butyl, t-butyl, 2-butyl, pentyl, hexyl, and the like. Generally, lower alkyl is preferably C1-C4 alkyl, and more preferably C1-C3 alkyl.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Cycloalkyl" means a non-aromatic, partially or completely saturated monovalent cyclic hydrocarbon radical containing 3 to 8 atoms. Examples of cycloalkyl groups include cyclopropyl, cyclobutyl, cyclopentyl and cyclohexyl.

"Effective amount" means an amount that is effective to prevent, alleviate or ameliorate symptoms of disease or prolong the survival of the subject being treated.

"Halogen" means fluorine, chlorine, bromine or iodine, preferably bromine or chlorine.

"Hetero atom" means an atom selected from N, O and S.

"Heteroaryl" means an aromatic heterocyclic ring system containing up to two rings. Preferred heteroaryl groups include, but are not limited to, thienyl, furyl, indolyl, pyrrolyl, pyridinyl, pyridine, pyrazinyl, oxazolyl, thiaxolyl, quinolinyl, pyrimidinyl, imidazole and tetrazolyl.

"Heterocycle" or "heterocyclyl" means a saturated or partially unsaturated, non-aromatic cyclic radical of 3 to 8 ring atoms in which from one to 3 ring atoms are hetero atoms selected from nitrogen, oxygen, S(O)n (where n is an integer from 0 to 2), or a combination thereof, the remaining ring atoms being C. Examples of preferred heterocycles are piperidine, piperazine, pyrrolidine, morpholine, indoline, tetrahydropyranyl, thiomorpholino, pentamethylene sulfide, and pentamethylene sulfone.

"$IC_{50}$" refers to the concentration of a particular compound required to inhibit 50% of a specific measured activity. $IC_{50}$ can be measured, inter alia, as is described subsequently.

"Lower alkyl" alone or in conjunction with another term, e.g. lower alkyl-heterocycle, denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Lower alkoxy" refers to any of the above lower alkyl groups attached to an oxygen atom. Typical lower alkoxy groups include methoxy, ethoxy, propyloxy or propoxy, butyloxy and the like.

"Oxo" means =O.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

"Therapeutically effective amount" means an amount of at least one designated compound, that significantly inhibits proliferation and/or prevents differentiation of a human tumor cell, including human tumor cell lines.

Compounds of the present invention as exemplified advantageously show IC50s from about 70 ηM to about 100 μM.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Synthesis

The compounds of formula I can be prepared according to scheme I.

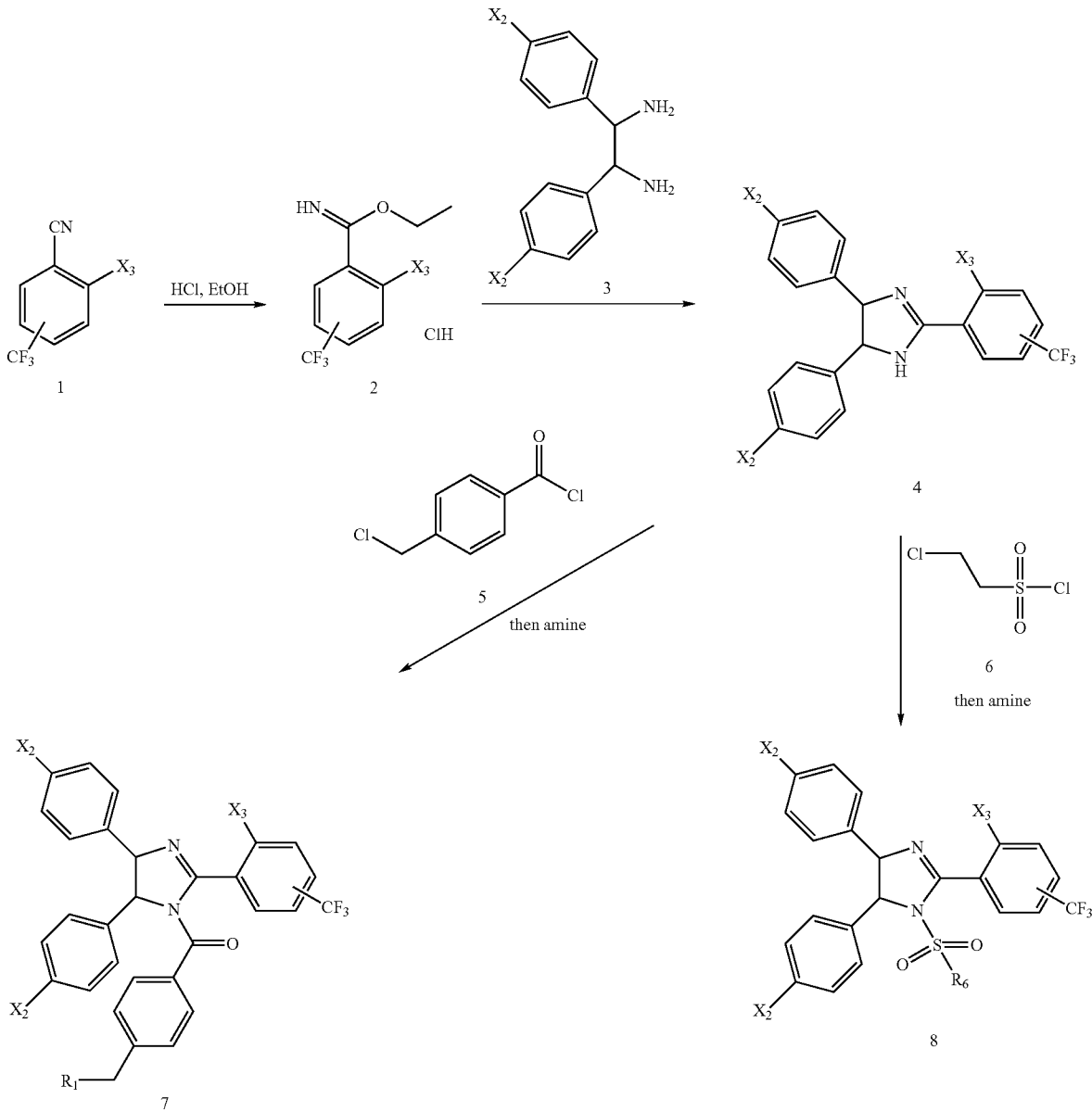

The benzonitrile 1, prepared according to the procedure provided by Harrison, C. R., et al. WO 9203421, is converted to the ethyl benzimidate 2 using HCl gas in ethanol. Condensation of the imidate 2 with the 1,2-diamine 3 is carried out in ethanol at 40-100° C. in the presence of a base such as triethylamine.

The meso-1,2-diamines of formula 3 are known compounds and prepared according to the literature procedures (see Jennerwein, M. et al. *Cancer Res. Clin. Oncol.* 1988, 114, 347-58; Vogtle, F.; Goldschmitt, E. *Chem. Ber.* 1976, 109, 1-40).

As set forth in scheme I, the compound of formula 7 can be prepared from compound 4 by the reaction with the benzoyl chloride 5 in the presence of a base such triethylamine, then with an amine in a solvent such as dimethylformamide.

As set forth in scheme I, the compound of formula 8 can be prepared from compound 4 by the reaction with the sulfonyl chloride 6 in the presence of a base such triethylamine, then with an amine in a solvent such as dimethylformamide.

The compound of formula 4 can be converted to the compound of formula 9 using phosgene in the presence of a base such as triethylamine (scheme 2). The compounds 10, 11, or 12 can then be obtained by the reaction of 9 with a suitable amine group (a known compounds or a compound prepared by known methods).

Scheme II

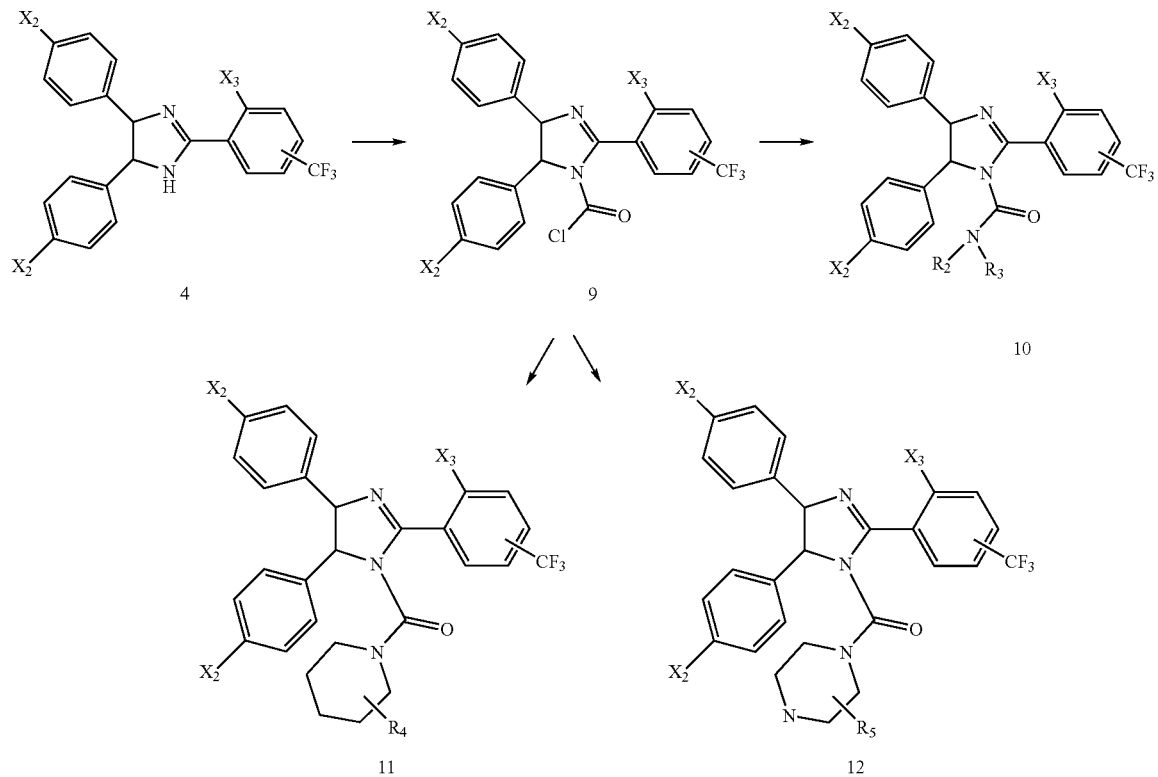

If it is desired, the $R_4$ and $R_5$ groups of in the compounds 11 and 12 can be functionalized further as illustrated in scheme 3.

Scheme III

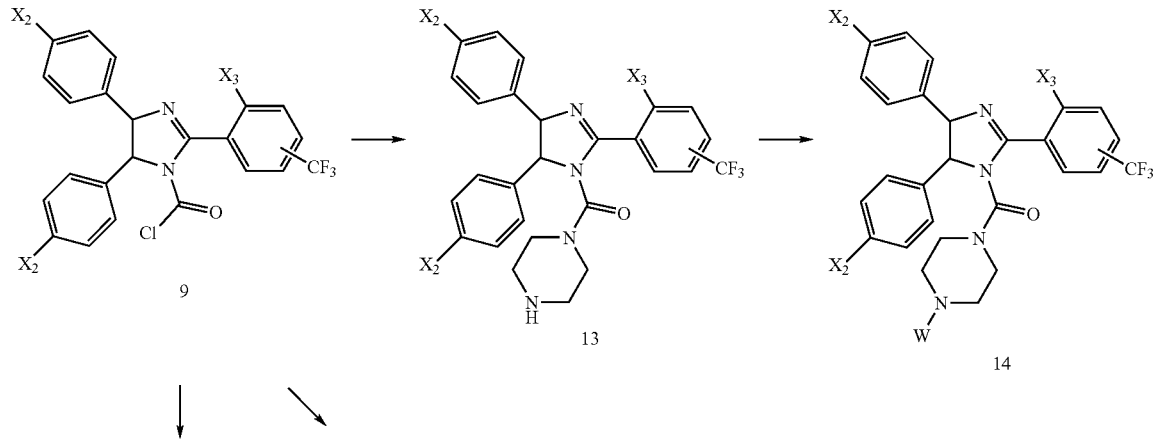

-continued

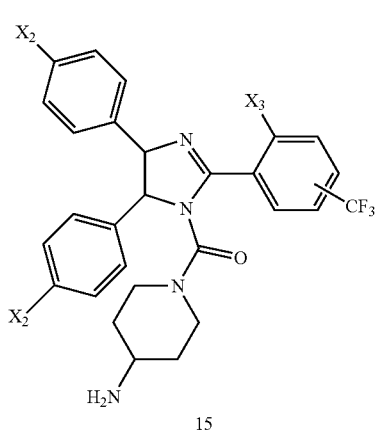

15

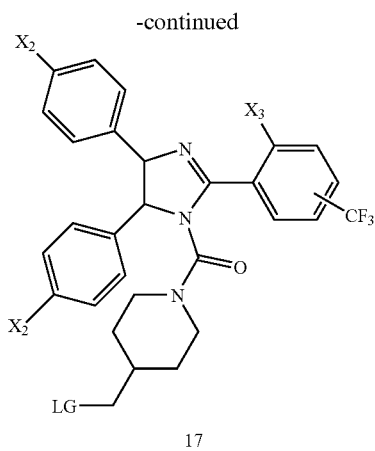

17

LG: Leaving group

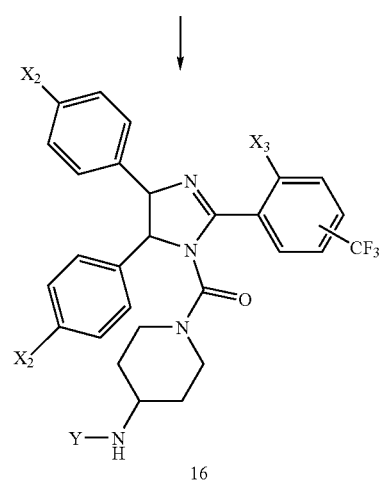

16

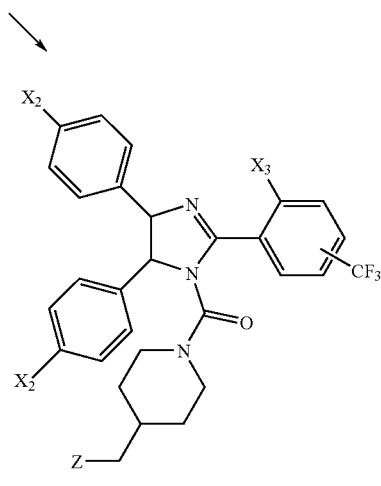

18

As set forth in scheme III, the compound of formula 9 can react with an appropriately protected piperazine to afford a compound of formula 13 after deprotection. A compound of 13 is then reacted with WX (e.g. X=halide, Ms, Ts, epoxide, alkene, or acyl, etc.) to give a compound of formula 14.

As set forth in scheme III, the compound of formula 9 can react with an appropriately protected piperidine to afford a compound of formula 15 after deprotection. A compound of 15 is then reacted with WX (e.g. X=halide, or acyl, etc.) to give a compound of formula 16.

As set forth in scheme III, a compound of formula 17 can be prepared from compound 9 by the reaction with 4-hydroxyethylpiperidine and triethylamine, followed by the conversion of the hydroxyl group to a suitable leaving group (LG) such as toluenemethylsulfonate. Compound 18 can be prepared from compound 17 by displacing the leaving group with an amine.

If it is desired to prepare a compound of formula 11 or 12 wherein the starting material is not commercially available, many synthetic methods known in the art can be employed. A representative process for synthesizing piperazin-2-one is provided in the examples. The following schemes illustrate some of these methods.

A compound of formula 21 (W can be any suitable group as defined in R5) can be prepared by alkylation of an appropriately protected compound of formula 19 with WX (X could be any suitable leaving group such as Cl, Br, I) using conventional methods (scheme IV). The amide anion is generated by a base such as sodium hydride. The reaction typically is carried out in dimethylformamide.

Scheme IV

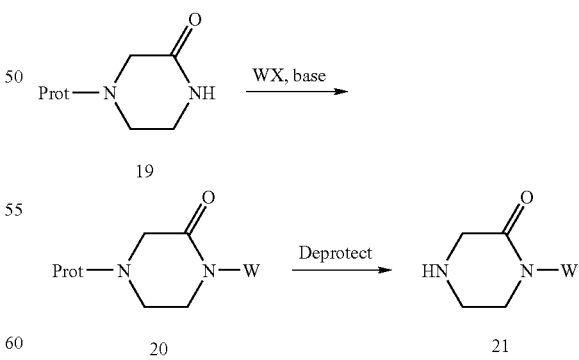

A compound of formula 24 (W can be any suitable group as defined in R5) can be prepared by reacting of an appropriately protected compound of formula 19 with WX (X could be any suitable leaving group such as Cl, Br, I), epoxide, or alkene using conventional methods (scheme V).

Scheme V

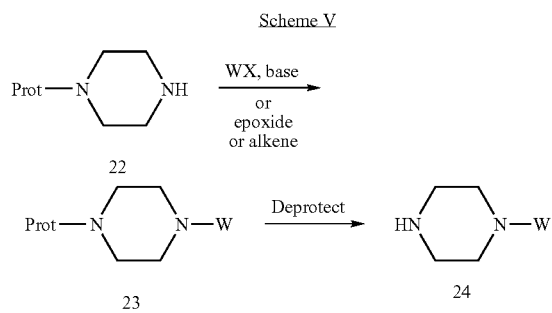

The following examples illustrate preferred methods for synthesizing the compounds of the present invention. Structural formulas follow. With regard to structural formulas, it is understood that oxygen and nitrogen atoms with available electrons have a hydrogen bound thereto, as indicated by compound name. These examples and preparations are illustrative and are not intended to be limiting. It should be understood that there may be other embodiments which fall within the spirit and scope of the invention as defined by the claims appended hereto.

The compounds synthesized in these examples are racemic. The enantiomers of the compounds of interest can be separated using chiral column chromatography (e.g. ChiralPak® AD, ChiralPak® OD, etc). One enanatiomer is shown to be more potent in our in vitro assay than the other.

EXAMPLE 1

4,5-Bis-(4-chloro-phenyl)-2-(2-ethoxy-4-trifluoromethyl-phenyl)-4,5-dihydro-1H-imidazole

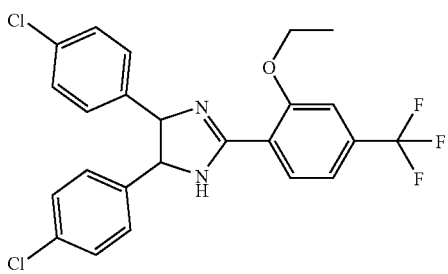

To a solution of 2-nitro-4-trifluoromethyl-benzonitrile (71.7 g, 318.5 mmol) in anhydrous ethanol (400 mL) at room temperature was added sodium ethoxide (238 mL, 637 mmol, 21% solution in ethanol) dropwise over a period of 30 min. The reaction mixture was stirred at room temperature for 1 h. Water (1 L) was added, and the mixture was stirred for 15 min. The solids were filtered off, washed with water, and dried in the vacuum oven (40° C.) overnight to give 2-ethoxy-4-trifluoromethyl-benzonitrile (64 g, 93% yield).

2-Ethoxy-4-trifluoromethyl-benzonitrile (64 g) was dissolved in 750 mL of anhydrous ethanol. The solution was cooled to 0° C. and saturated with hydrogen chloride gas. The reaction flask was then sealed with a Teflon stopper and stirred at room temperature for 11 d. The progress of the reaction was checked every few days, and the solution was saturated again with hydrogen chloride gas. Nitrogen gas was bubbled through the solution to remove excess hydrogen chloride gas. The solvent was removed and the residue was triturated in diethyl ether to afford ethyl 2-ethoxy-4-trifluoromethyl-benzimidate hydrochloride (59.5 g, 67% yield) as white solids.

A solution of meso-1,2-bis-(4-chloro-phenyl)-ethane-1,2-diamine (50.16 g, 178.4 mmol, prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40), ethyl 2-ethoxy-4-trifluoromethyl-benzimidate hydrochloride (59 g, 178.4 mmol), and triethylamine (49.7 mL, 356.8 mmol) in ethanol (700 mL) was heated at reflux for 4 h. The solvent was removed, and the residue was taken in ethyl acetate (800 mL) and saturated solution of sodium carbonate (300 mL). The layers were separated, and the product was extracted with ethyl acetate (1×200 mL). The organic layers were washed with brine (1×100 mL) and dried over anhydrous magnesium sulfate. The solids were then filtered off, and the filtrate was concentrated in vacuo. Purification of the crude residue by flash column chromatography (60 Å silica gel) eluting with 50% ethyl acetate in hexanes yielded 4,5-bis-(4-chloro-phenyl)-2-(2-ethoxy-4-trifluoromethyl-phenyl)-4,5-dihydro-1H-imidazole (64.47 g, 75% yield) as yellow solids.

EXAMPLE 2

In an analogous manner as described in example 1, there were obtained:

4,5-bis-(4-chloro-phenyl)-2-(2-isopropoxy-4-trifluoromethyl-phenyl)-4,5-dihydro-1H-imidazole

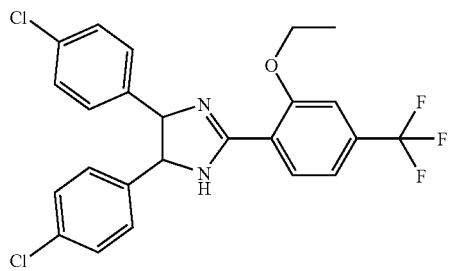

4,5-bis-(4-chloro-phenyl)-2-(2-ethoxy-5-trifluoromethyl-phenyl)-4,5-dihydro-1H-imidazole

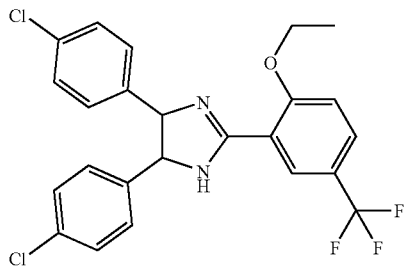

EXAMPLE 3

4,5-Bis-(4-chloro-phenyl)-2-(2-ethoxy-4-trifluoromethyl-phenyl)-4,5-dihydro-1H-imidazole-1-carbonyl chloride

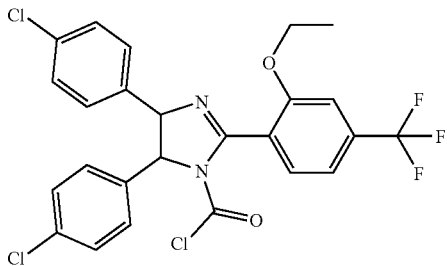

To a solution of 4,5-bis-(4-chloro-phenyl)-2-(2-ethoxy-4-trifluoromethyl-phenyl)-4,5-dihydro-1H-imidazole (46 g, 95.97 mmol, example 1) and triethylamine (66.9 mL, 479.9 mmol) in methylene chloride (2 L) cooled to 0° C. was added phosgene (124.3 mL, 239.9 mmol, ~20% solution in toluene) dropwise over a period of 30 min. The reaction mixture was stirred at room temperature for 1 h. Nitrogen gas was bubbled through the reaction mixture to remove excess phosgene. The reaction mixture was concentrated to dryness, and the residue was dried in vacuo for 1 h to give 4,5-bis-(4-chloro-phenyl)-2-(2-ethoxy-4-trifluoromethyl-phenyl)-4,5-dihydro-imidazole-1-carbonyl chloride (51 g, 98% yield) as off-white solids. The product was used without further purification.

EXAMPLE 4

In an analogous manner as described in example 3, there were obtained:

4,5-Bis-(4-chloro-phenyl)-2-(2-isopropoxy-4-trifluoromethyl-phenyl)-4,5-dihydro-imidazole-1-carbonyl chloride

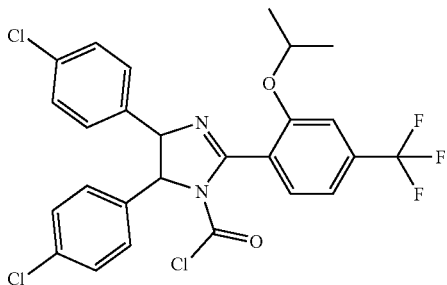

4,5-Bis-(4-chloro-phenyl)-2-(2-ethoxy-5-trifluoromethyl-phenyl)-4,5-dihydro-imidazole-1-carbonyl chloride

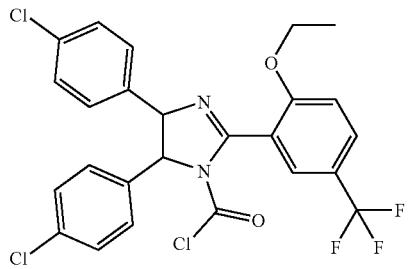

EXAMPLE 5

The following general procedure was used for the reaction of the 1-carbonyl chloride 9 (examples 3 and 4) with the commercially available amine.

A solution of the 1-carbonyl chloride 9 (1 eq., prepared according the procedure described in example 3) in methylene chloride was added to a solution of the amine (1-2 eq.) and triethylamine in methylene chloride. The reaction mixture was stirred at room temperature for 1 h. The reaction was worked up with aqueous sodium bicarbonate and extracted with methylene chloride. The organic extracts were washed with water and brine, and dried over anhydrous sodium sulfate. The solids were filtered off, and the filtrate was concentrated in vacuo. Purification of the crude residue by flash column chromatography gave the desired urea product.

EXAMPLE 6

[4,5-Bis-(4-chloro-phenyl)-2-(2-ethoxy-4-trifluoromethyl-phenyl)-4,5-dihydro-imidazol-1-yl]-[4-(propane-2-sulfonyl)-piperazin-1-yl]-methanone

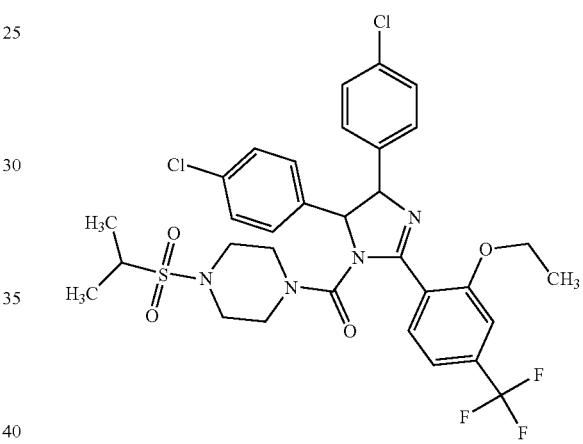

A solution of 1-BOC-piperazine (0.617 mmol) and diisopropylethylamine (0.679 mmol) in 0.5 mL of methylene chloride was added to a 4 mL vial. Propane-2-sulfonyl chloride (0.679 mmol) was added to the vial, and the reaction mixture was shaken overnight at room temperature. When the reaction was complete, it was diluted with 1.5 mL of methylene chloride and extracted with 1 mL of 1N solution of hydrogen chloride followed by 1 mL of 10% potassium carbonate solution. The organic layer was concentrated in vacuo. The residue was dissolved in 0.5 mL of tetrahydrofuran and 4M solution of hydrogen chloride in dioxane (0.5 mL). The solution was shaken overnight at room temperature then concentrated in vacuo to give 1-(propane-2-sulfonyl)-piperazine.

1-(Propane-2-sulfonyl)-piperazine (0.0286 mmol) was dissolved in 0.25 mL of methylene chloride and added to a solution of 4,5-bis-(4-chloro-phenyl)-2-(2-ethoxy-4-trifluoromethyl-phenyl)-4,5-dihydro-imidazole-1-carbonyl chloride (0.024 mmol, example 3) and diisopropylethylamine (0.072 mmol) in .25 mL of methylene chloride in a 4 mL vial. The vial was capped and shaken overnight at room temperature. The reaction mixture was diluted with 1 mL of methylene chloride and 1 mL of water. The vial was agitated and centrifuged. The organic layer was transferred to a 4 mL vial and concentrated in vacuo to give [4,5-bis-(4-chloro-phenyl)-2-(2-ethoxy-4-trifluoromethyl-phenyl)-4,5-dihydro-imidazol-1-yl]-[4-(propane-2-sulfonyl)-piperazin-1-yl]-methanone. LR-MS (M+H)$^+$=697.4.

EXAMPLE 7A

1-Benzyl-4-[45-bis-(4-chloro-phenyl)-2-(2-ethoxy-4-trifluoromethyl-phenyl)-4,5-dihydro-imidazole-1-carbonyl]-piperazin-2-one hydrochloride

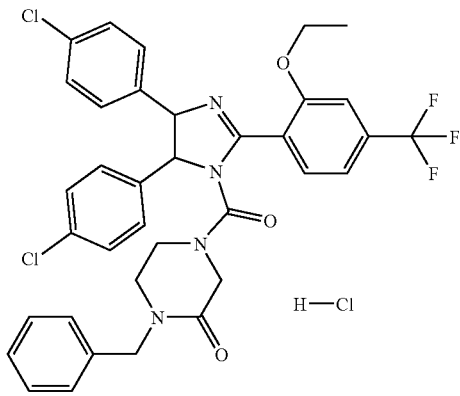

Sodium hydride (80 mg, 2.0 mmol, 60% in mineral oil) was added to a solution of 4-tert-butyloxycarbonyl-piperazin-2-one (200 mg, 1.0 mmol) in dimethylformamide (5.0 mL) at 0° C. The reaction was stirred at 0° C. for 0.5 h. To this mixture was added benzyl bromide (300 uL, 2.5 mmol) and the reaction was stirred for 2 h at room temperature. The reaction mixture was quenched with a dilute aqueous solution of sodium bicarbonate and extracted with methylene chloride. The organic extracts were washed with brine and dried over anhydrous sodium sulfate. Purification of the crude residue by chromatography over silica gel using 30% ethyl acetate in hexane gave 4-tert-butyloxycarbonyl-2-benzyl-piperazin-2-one (174 mg, 60% yield).

Hydrochloric acid (0.25 mL, 1.00 mmol, 4 M in 1,4-dioxane) was added to a solution of 4-tert-butyloxycarbonyl-2-benzyl-piperazin-2-one (174 mg, 0.60 mmol) in 1,4-dioxane (1.0 mL). The mixture was stirred overnight. The reaction was concentrated to give 2-benzyl-piperazin-2-one hydrochloride as an off-white solid (130 mg, 97% yield).

4,5-Bis-(4-chloro-phenyl)-2-(2-ethoxy-4-trifluoromethyl-phenyl)-4,5-dihydro-imidazole-1-carbonyl chloride (example 3) was reacted with 2-benzyl-piperazin-2-one hydrochloride using the procedure as described in example 5 to give 4-[4,5-bis-(4-chloro-phenyl)-2-(2-ethoxy-4-trifluoromethyl-phenyl)-4,5-dihydro-imidazole-carbonyl]-1-benzyl-piperazin-2-one. It was then dissolved in dilute hydrochloric acid (0.5 N, 1 mL) and lyophilized to give 4-[4,5-bis-(4-chloro-phenyl)-2-(2-ethoxy-4-trifluoromethyl-phenyl)-4,5-dihydro-imidazole-carbonyl]-1-benzyl-piperazin-2-one hydrochloride as an off-white powder (65 mg, 89% yield). LR-MS (APCI): 695.6 [(M+H)$^+$].

EXAMPLE 7B

[4,5-Bis-(4-chloro-phenyl)-2-(2-ethoxy-4-trifluoromethyl-phenyl)-4,5-dihydro-imidazol-1-yl]-[4-(morpholine-4-sulfonyl)-piperazin-1-yl]-methanone

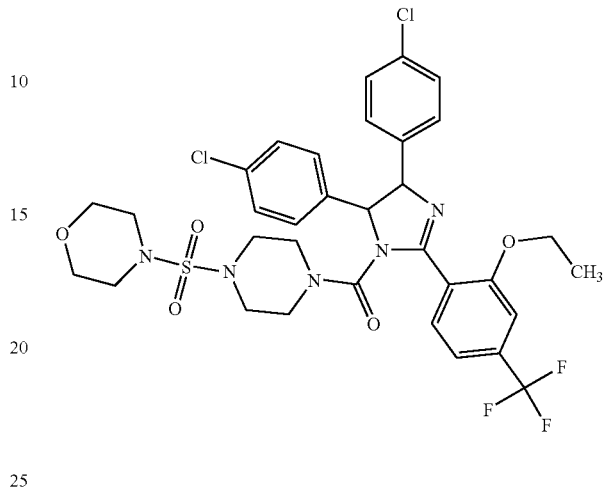

The triflate salt of the methylated sulfuryldiimidazole (3.14 g, 8.04 mmol) was dissolved in acetonitrile. 1-Boc-piperazine (1.0 g, 5.37 mmol) and diisopropylethylamine (1 eq.) were added at once. The reaction mixture was stirred at room temperature overnight. It was diluted with ethyl acetate and washed with water. The organic layers were dried, filtered, and concentrated in vacuo to give a viscous oil (2.6 g). Purification of the oil by flash chromatography gave 4-(2-methyl-imidazole-1-sulfonyl)-piperazine-1-carboxylic acid tert-butyl ester (1.4 g, 79% yield). LR-MS: 331 [(M+H)$^+$].

A solution of 4-(2-methyl-imidazole-1-sulfonyl)-piperazine-1-carboxylic acid tert-butyl ester (1.4 g, 4.24 mmol) in methylene chloride was cooled in an ice bath, and trifluoromethanesulfonic acid methyl ester (0.56 mL, 4.9 mmol) was added via a pipet. After stirring at ice temperature for 3 h, the solvent was evaporated to give 4-(2-methyl-imidazole-1-sulfonyl)-piperazine-1-carboxylic acid tert-butyl ester triflate salt as yellow solids.

A solution of the triflate salt (60 mg, 0.12 mmol), morpholine (31.7 mg, 0.36 mmol) and 63 uL of diisopropylethylamine (0.36 mmol) in 0.25 mL of acetonitrile was stirred at ambient temperature overnight. The reaction was diluted with 1 mL of methylene chloride and 0.5 mL of 1.0 M hydrochloric acid. The organic phase was filtered through a small pad of silica gel and the solvent evaporated to yield 4-(morpholine-4-sulfonyl)-piperazine-1-carboxylic acid tert-butyl ester (39 mg, 95%). LR-MS: 336 [(M+H)$^+$].

4-(Morpholine-4-sulfonyl)-piperazine-1-carboxylic acid tert-butyl ester (39 mg) was dissolved in 4 mL of dioxane, and 4 mL of 4.0 M hydrochloric acid in dioxane was added. After standing overnight at ambient temperature, the solvent was removed to give 4-(piperazine-1-sulfonyl)-morpholine hydrochloride as a white solid.

4-(Piperazine-1-sulfonyl)-morpholine hydrochloride (0.042 mmol) was suspended in methylene chloride, and 400 uL of diisopropylethylamine was added. The mixture was added to 4,5-bis-(4-chloro-phenyl)-2-(2-ethoxy-4-trifluoromethyl-phenyl)-4,5-dihydro-imidazole-1-carbonyl chloride (10 mg, 0.019 mmol, example 3), and the reaction mixture was allowed to stand overnight. It was diluted with methylene chloride and washed with water. The organic layer was evaporated, and the residue purified by flash chromatography using ethyl acetate and hexanes to give [4,5-bis-(4-chloro-phenyl)-2-(2-ethoxy-4-trifluoromethyl-phenyl)-4,5-dihydro-imidazol-1-yl]-[4-(morpholine-4-sulfonyl)-piperazin-1-yl]-methanone (9.0 mg). LR-MS: 740.2 [(M+H)$^+$].

EXAMPLE 8A

3-{4-[4,5-Bis-(4-chloro-phenyl)-2-(2-ethoxy-4-trifluoromethyl-phenyl)-4,5-dihydro-imidazole-1-carbonyl]-piperazin-1-yl}-propionitrile hydrochloride

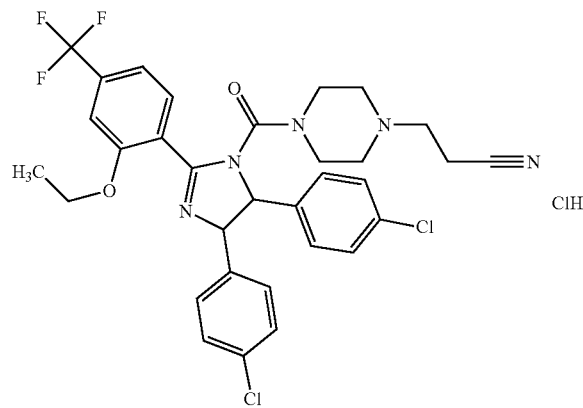

Phosgene (3.8 mL, 7.22 mmol, 1.9 M in toluene) was added dropwise to a cooled (0° C.) mixture of triethylamine (1.3 mL, 9.62 mmol) and 4,5-bis-(4-chloro-phenyl)-2-(2-ethoxy-4-trifluro-phenyl)-4,5-dihydro-1H-imidazole (1.15 g, 2.41 mmol) in methylene chloride (20 mL). The reaction mixture was stirred for 0.5 h at 0° C., and the solvent was evaporated. The residue was kept under high vacuum for 30 min and dissolved in methylene chloride (20 mL). The solution was added dropwise to a cooled (0° C.) solution of 4-tert-butyloxycarbonylpiperazine (0.90 g, 4.81 mmol) in methylene chloride (16 mL). After 1 h, the reaction was worked up with aqueous sodium bicarbonate solution and extracted with methylene chloride. The organic extracts were washed with water, brine, and dried over anhydrous sodium sulfate. Evaporation of the solvents and chromatography of the residue over silica gel using 50% ethyl acetate in hexanes gave [4,5-bis-(4-chloro-phenyl)-2-(2-ethoxy-4-trifluoromethyl-phenyl)-4,5-dihydro-imidazol-1-yl]-[4-tert-butyloxycarbonylpiperazin-1-yl]-methanone as a yellow foam (1.30 g, 78%).

Hydrochloric acid (10 mL, 40 mmol, 4 M in 1,4-dioxane) was added to a cooled (0° C.) solution of [4,5-bis-(4-chloro-phenyl)-2-(2-ethoxy-4-trifluoromethyl-phenyl)-4,5-dihydro-imidazol-1-yl]-[4-tert-butyloxycarbonylpiperazin-1-yl]-methanone in 1,4-dioxane (10 mL). The mixture was stirred at room temperature overnight. Evaporation of the solvent gave [4,5-bis-(4-chloro-phenyl)-2-(2-ethoxy-4-trifluoromethyl-phenyl)-4,5-dihydro-imidazol-1-yl]-(piperazin-1-yl)-methanone hydrochloride as an off-white solid (1.10 g, 98% yield).

2-Bromopropionitrile (10 uL, 0.120 mmol) was added to a mixture of [4,5-bis-(4-chloro-phenyl)-2-(2-ethoxy-4-trifluoromethyl-phenyl)-4,5-dihydro-imidazol-1-yl]-[piperazin-1-yl]-methanone hydrochloride and diisopropylethylamine (42 uL, 0.240 mmol) in dimethylformamide (1.0 mL). The reaction was stirred at room temperature overnight. Evaporation of the solvent and purification of the crude residue by flash chromatography over silica gel using 1-2% methanol in methylene chloride gave 3-{4-[4,5-bis-(4-chloro-phenyl)-2-(2-ethoxy-4-trifluoromethyl-phenyl)-4,5-dihydro-imidazole-1-carbonyl]-piperazin-1-yl}-propionitrile, which was dissolved in dilute hydrochloric acid (0.5 N, 1 mL) and lyophilized to give 3-{4-[4,5-bis-(4-chloro-phenyl)-2-(2-ethoxy-4-trifluoromethyl-phenyl)-4,5-dihydro-imidazole-1-carbonyl]-piperazin-1-yl}-propionitrile hydrochloride as an off-white powder (20 mg, 39% yield). LR-MS (APCI): 644.4 [(M+H)$^+$].

EXAMPLE 8B

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-methyl-acetamide

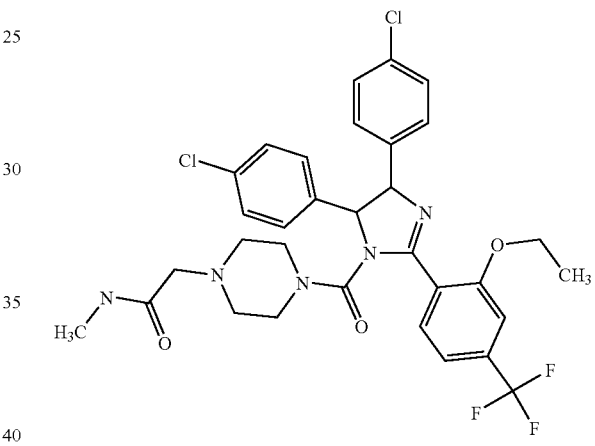

A solution of chloroacetylchloride (8.85 mmol) in 10 mL of methylene chloride was cooled to approximately −40° C. in a sealed 40 mL vial. Methylamine (18.6 mmol, 9.3 mL of a 2M in tetrahydrofuran) was added in a portion-wise fashion via a syringe through a pierceable septum to the stirring solution. The reaction was stirred for 1 h at reduced temperature. The solution was then made acidic with 1N hydrochloric acid and then diluted with 10 mL of methylene chloride. The vial was agitated and centrifuged. The organic layer was transferred to 40 mL vials and concentrated in vacuo to give 2-chloro-N,N-dimethyl-acetamide.

2-Chloro-N,N-dimethyl-acetamide (0.0194 mmol) in dimethylformamide (0.25 mL) was pipeted into a 4 mL vial containing a solution of 4,5-bis-(4-chloro-phenyl)-2-(2-ethoxy-4-trifluoromethyl-phenyl)-4,5-dihydro-1H-imidazole (0.0169 mmol, example 1) and diisopropylethylamine (0.0194 mmol) in 0.25 mL of dimethylformamide. The vial was capped and heated to 65° C. for 2 d. The reaction was diluted with 1.5 mL of methylene chloride and 0.5 mL of water. The vial was agitated and centrifuged. The organic layer was transferred to a 4 mL vial and concentrated in vacuo to give 2-{4-[4,5-bis-(4-chloro-phenyl)-2-(2-ethoxy-4-trifluoromethyl-phenyl)-4,5-dihydro-imidazole-1-carbonyl]-piperazin-1-yl}-N-methyl-acetamide. LR-MS: 663 [(M+H)$^+$].

EXAMPLE 9

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-dimethylamino-ethanone

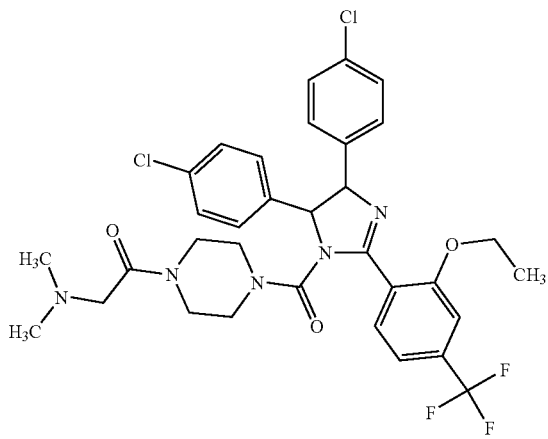

[4,5-Bis-(4-chloro-phenyl)-2-(2-ethoxy-4-trifluoromethyl-phenyl)-4,5-dihydro-imidazol-1-yl]-piperazin-1-yl-methanone (372 mg, 0.63 mmol, example 8A) and diisopropylethylamine (230 uL, 1.32 mmol) were dissolved in methylene chloride (4 mL) and cooled to ice temperature. Chloroacetyl chloride (100 uL, 1.26 mmol) in methylene chloride (1 mL) was added dropwise and this mixture was stirred for 30 min at ice temperature. The reaction was diluted with methylene chloride and washed with water. The organic layers were dried over anhydrous magnesium sulfate. The solids were filtered off, and the filtrate was concentrated. Purification of the crude material by flash chromatography using ethyl acetate and hexanes gave 1-{4-[4,5-bis-(4-chloro-phenyl)-2-(2-ethoxy-4-trifluoromethyl-phenyl)-4,5-dihydro-imidazole-1-carbonyl]-piperazin-1-yl}-2-chloro-ethanone (193 mg, 0.29 mmol).

To a solution of 1-{4-[4,5-bis-(4-chloro-phenyl)-2-(2-ethoxy-4-trifluoromethyl-phenyl)-4,5-dihydro-imidazole-1-carbonyl]-piperazin-1-yl}-2-chloro-ethanone (9.65 mg) and diisopropylethylamine (5 uL) was added dimethylamine (50 uL, 2.0M solution in tetrahydrofuran). The reaction mixture was capped and heated at 60° C. overnight. It was diluted with methylene chloride and washed with water. The organic layer was concentrated to dryness to give 1-{4-[4,5-bis-(4-chloro-phenyl)-2-(2-ethoxy-4-trifluoromethyl-phenyl)-4,5-dihydro-imidazole-1-carbonyl]-piperazin-1-yl}-2-dimethylamino-ethanone (9.17 mg, 92% yield). LR-MS: 677.3 [(M+H)$^+$].

EXAMPLE 10

4-[4,5-Bis-(4-chloro-phenyl)-2-(2-ethoxy-4-trifluoromethyl-phenyl)-4,5-dihydro-imidazole-1-carbonyl]-piperazine-1-carbothioic acid methylamide

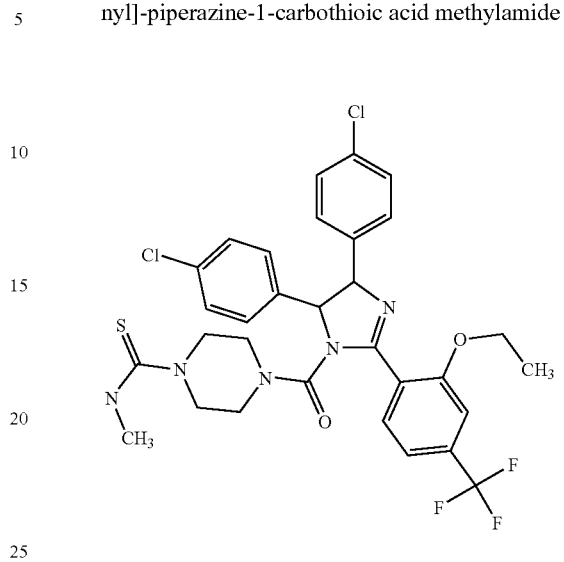

[4,5-Bis-(4-chloro-phenyl)-2-(2-ethoxy-4-trifluoromethyl-phenyl)-4,5-dihydro-imidazol-1-yl]-piperazin-1-yl-methanone (279 mg, 0.47 mmol, example 8A) was dissolved in methylene chloride (3 mL) and methylisothiocyanate (64 uL) was added. After stirring 3 h, the reaction mixture was concentrated to dryness. Purification of the crude residue by flash chromatography (silica gel) eluting with ethyl acetate and hexanes gave 4-[4,5-bis-(4-chloro-phenyl)-2-(2-ethoxy-4-trifluoromethyl-phenyl)-4,5-dihydro-imidazole-1-carbonyl]-piperazine-1-carbothioic acid methylamide (195 mg). LR-MS: 664.4 [(M+H)$^+$].

EXAMPLE 11

4-{4-[4,5-Bis-(4-chloro-phenyl)-2-(2-ethoxy-4-trifluoromethyl-phenyl)-4,5-dihydro-imidazole-1-carbonyl]-piperazine-1-carbonyl}-piperazin-2-one

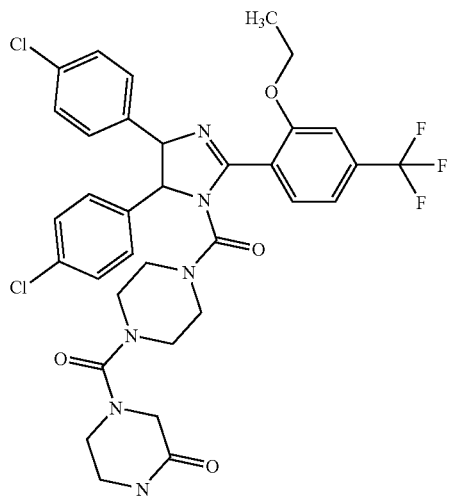

[4,5-Bis-(4-chloro-phenyl)-2-(2-ethoxy-4-trifluoromethyl-phenyl)-4,5-dihydro-imidazol-1-yl]-piperazin-1-yl-methanone (50 mg, 0.085 mmol, example 8A) was dissolved in methylene chloride (1 mL) and cooled in an ice bath. Phosgene (250 uL, 20% solution in toluene)) was added, and the mixture was stirred for 30 min. The solvent was evaporated and the residue was taken in methylene chloride. One third of this solution (0.028 mmol) was treated with 2-piperazinone (8.5 mg) and diisopropylethylamine (15 ul). The mixture was sonicated to aid in dissolving the amine and allowed to stand at ambient temperature overnight. It was diluted with methylene chloride and washed with water. The organic portion was separated and evaporated to give the crude urea. Purification of the crude urea by flash chromatography (silica gel) using ethyl acetate and hexanes gave 4-{4-[4,5-bis-(4-chloro-phenyl)-2-(2-ethoxy-4-trifluoromethyl-phenyl)-4,5-dihydro-imidazole-1-carbonyl]-piperazine-1-carbonyl}-piperazin-2-one (9.0 mg). LR-MS: 718.4 [(M+H)$^+$].

EXAMPLE 12

[4,5-Bis-(4-chloro-phenyl)-2-(2-ethoxy-4-trifluoromethyl-phenyl)-4,5-dihydro-imidazol-1-yl]-[4-(2-methanesulfonyl-ethyl)-piperazin-1-yl]-methanone hydrochloride

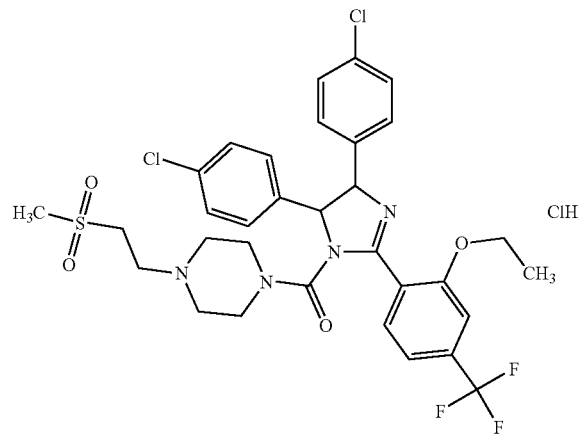

Methyl vinyl sulfone (11 uL, 0.125 mmol) was added to a mixture of [4,5-bis-(4-chloro-phenyl)-2-(2-ethoxy-4-trifluoromethyl-phenyl)-4,5-dihydro-imidazol-1-yl]-[piperazin-1-yl]-methanone (40 mg, 0.064 mmol, example 8A), and diisopropylethylamine (35 uL, 0.205 mmol) in anhydrous dimethylformamide (1.0 mL). The reaction was stirred overnight. Evaporation of the solvent and flash chromatography of the residue over silica gel using 0-5% methanol in methylene chloride gave [4,5-bis-(4-chloro-phenyl)-2-(2-ethoxy-4-trifluoromethyl-phenyl)-4,5-dihydro-imidazol-1-yl]-[4-(2-(methylsulfone)ethyl)-piperazin-1-yl]-methanone, which was dissolved in dilute hydrochloric acid (0.5 N, 1 mL) and lyophilized to give [4,5-bis-(4-chloro-phenyl)-2-(2-ethoxy-4-trifluoromethyl-phenyl)-4,5-dihydro-imidazol-1-yl]-[4-(2-(methylsulfone)ethyl)-piperazin-1-yl]-methanone hydrochloride as an off-white powder (28 mg, 80%). LR-MS (APCI): 697.7 [(M+H)$^+$].

EXAMPLE 13A

4-{1-[4,5-Bis-(4-chloro-phenyl)-2-(2-ethoxy-4-trifluoromethyl-phenyl)-4,5-dihydro-imidazole-1-carbonyl]-piperidin-4-ylmethyl}-piperazin-2-one hydrochloride

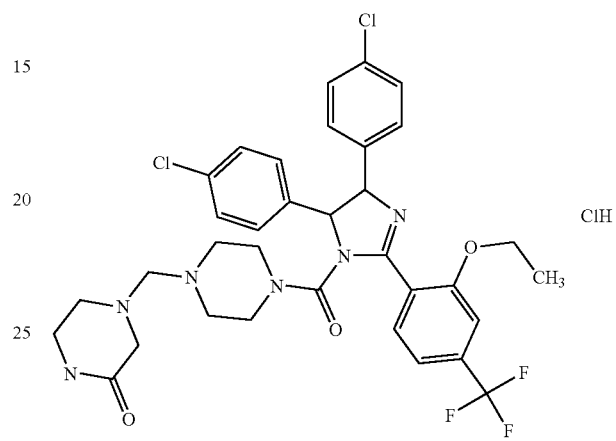

Phosgene (1.8 mL, 3.6 mmol, 1.9 M in toluene) was added dropwise to a cooled (0° C.) solution of triethylamine (0.57 mL, 4.0 mmol) and 4,5-bis-(4-chloro-phenyl)-2-(2-ethoxy-4-trifluro-phenyl)-4,5-dihydro-1H-imidazole (550 mg, 1.2 mmol, example 1) in methylene chloride (5.0 mL). The reaction mixture was stirred for 0.5 h at 0° C. The solvent was removed under reduced pressure. The residue was kept under high vacuum for 30 min and dissolved in methylene chloride (5.0 mL). Triethylamine (0.170, 1.2 mmol) and 4-(hydroxymethyl)piperidine (0.50 g, 4.4 mmol) were added. After 1 h, the reaction was worked up with aqueous sodium bicarbonate and extracted with methylene chloride. The organic extracts were washed with brine and dried over anhydrous sodium sulfate. Evaporation of the solvents and flash chromatography of the residue over silica gel using 1-4% methanol in methylene chloride gave [4,5-bis-(4-chloro-phenyl)-2-(2-ethoxy-4-trifluoromethyl-phenyl)-4,5-dihydro-imidazol-1-yl]-[4-hydroxymethyl-piperidin-1-yl]-methanone (560 mg, 79%).

To a cooled (0° C.) solution of [4,5-bis-(4-chloro-phenyl)-2-(2-ethoxy-4-trifluoromethyl-phenyl)-4,5-dihydro-imidazol-1-yl]-[4-hydroxy methyl-piperidin-1-yl]-methanone (60 mg, 0.096 mmol) in methylene chloride (2 mL) was added carbon tetrabromide (70 mg, 0.210 mmol) followed by triphenyl phosphine (55 mg, 0.21 mmol). The reaction mixture was stirred at ambient temperature for 2.5 h. The reaction was diluted with water and extracted with methylene chloride. The organic extracts were washed with water, brine, and dried over anhydrous sodium sulfate. Evaporation of the solvents and chromatography of the residue over silica gel using 1-5% methanol in methylene chloride gave [4,5-bis-(4-chloro-phenyl)-2-(2-ethoxy-4-trifluoromethyl-phenyl)-4,5-dihydro-imidazol-1-yl]-[4-bromomethyl-piperidin-1-yl]-methanone (50 mg, 76%).

Piperazine-2-one (21 mg, 0.21 mmol) was added to a solution [4,5-bis-(4-chloro-phenyl)-2-(2-ethoxy-4-trifluoromethyl-phenyl)-4,5-dihydro-imidazol-1-yl]-[4-bromomethyl-piperidin-1-yl]-methanone (48 mg, 0.07 mmol) in anhydrous dimethylformamide (2.0 mL). The mixture was stirred overnight at 70° C. The reaction mixture was cooled to ambient temperature and partitioned between methylene chloride and a saturated aqueous solution of ammonium chloride. The aqueous phase was extracted with methylene chloride and the combined organic extracts were washed with brine, and dried over anhydrous sodium sulfate. Evaporation of the solvents and chromatography of the residue over silica gel using 1-5% methanol in methylene chloride gave [4,5-bis-(4-chloro-phenyl)-2-(2-ethoxy-4-trifluoromethyl-phenyl)-4,5-dihydro-imidazol-1-yl]-[4-(piperazin-2-one-4-yl-methyl)-piperidin-1-yl]-methanone, which was dissolved in dilute hydrochloric acid (0.5 N, 1 mL) and lyophilized to give [4,5-bis-(4-chloro-phenyl)-2-(2-ethoxy-4-trifluoromethyl-phenyl)-4,5-dihydro-imidazol-1-yl]-[4-(piperazin-2-one-4-yl-methyl)-piperidin-1-yl]-methanone hydrochloride as an off-white powder (23 mg, 45%). LR-MS (APCI): 702.4 [(M+H)$^+$].

EXAMPLE 13B

[4,5-Bis-(4-chloro-phenyl)-2-(2-ethoxy-4-trifluoromethyl-phenyl)-4,5-dihydro-imidazol-1-yl]-[4-(3,3,3-trifluoro-2-hydroxy-propyl)-piperazin-1-yl]-methanone hydrochloride

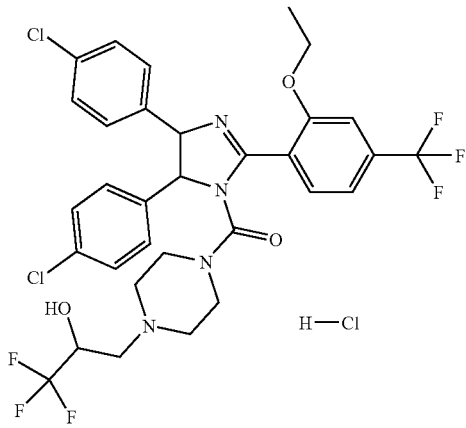

1,1,1-trifluoro-2,3-epoxypropane (9 uL, 0.10 mmol) was added to a mixture of [4,5-bis-(4-chloro-phenyl)-2-(2-ethoxy-4-trifluoromethyl-phenyl)-4,5-dihydro-imidazol-1-yl]-[piperazin-1-yl]-methanone (30 mg, 0.048 mmol) and triethylamine (20 uL, 0.144 mmol) in anhydrous methanol (1.0 mL). The reaction was stirred overnight. Evaporation of the solvent and chromatography of the residue over silica gel using 0-5% methanol in methylene chloride gave [4,5-bis-(4-chloro-phenyl)-2-(2-ethoxy-4-trifluoromethyl-phenyl)-4,5-dihydro-imidazol-1-yl]-[4-(2-hydroxy-2-trifluoromethyl-ethyl)-piperazin-1-yl]-methanone, which was dissolved in dilute hydrochloric acid (0.5 N, 1 mL) and lyophilized to give [4,5-bis-(4-chloro-phenyl)-2-(2-ethoxy-4-trifluoromethyl-phenyl)-4,5-dihydro-imidazol-1-yl]-[4-(2-hydroxy-2-trifluoromethylethyl)-piperazin-1-yl]-methanone hydrochloride as an off-white powder (38 mg, 84%). LR-MS (APCI): 703.5 [(M+H)$^+$].

EXAMPLE 14

[4,5-Bis-(4-chloro-phenyl)-2-(2-ethoxy-5-trifluoromethyl-phenyl)-4,5-dihydro-imidazol-1-yl]-{4-[4-(2-hydroxy-ethyl)-piperazin-1-ylmethyl]-phenyl}-methanone hydrochloride

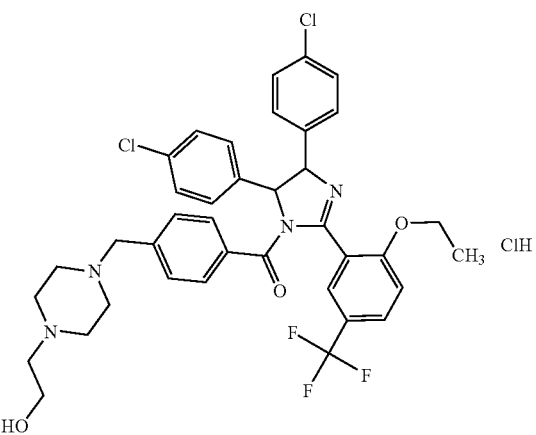

4-Chloromethylbenzoyl chloride (140 mg, 0.74 mmol) was added to a cooled solution of triethylamine (0.20 mL, 1.44 mmol) and 4,5-bis-(4-chloro-phenyl)-2-(2-ethoxy-5-trifluoromethyl-phenyl)-4,5-dihydro-1H-imidazole (300 mg, 0.61 mmol). The reaction mixture was stirred at room temperature for 2 h. The reaction was diluted with methylene chloride and washed with water and brine, and dried over anhydrous sodium sulfate. The solvents were removed under reduced pressure and flash chromatography of the residue over silica gel using 10-25% ethyl acetate in hexanes gave [4,5-bis-(4-chloro-phenyl)-2-(2-ethoxy-5-trifluoromethyl-phenyl)-4,5-dihydro-imidazol-1-yl]-(4-chloromethyl-phenyl)-methanone (330 mg, 84%).

4-(2-Hydroxyethyl)-piperazine (10 uL, 0.08 mmol) was added to a solution of [4,5-bis-(4-chloro-phenyl)-2-(2-ethoxy-5-trifluoromethyl-phenyl)-4,5-dihydro-imidazol-1-yl]-(4-chloromethyl-phenyl)-methanone (20 mg, 0.03 mmol) and diisopropylethylamine (7 uL, 0.04 mmol) in anhydrous dimethylformamide (1.0 mL). The mixture was stirred overnight at 80° C. Evaporation of the solvent and chromatography of the residue over silica gel using 1-5% methanol in methylene chloride gave [4,5-bis-(4-chloro-phenyl)-2-(2-ethoxy-5-trifluoromethyl-phenyl)-4,5-dihydro-imidazol-1-yl]-[4-{(4-(2-hydroxyethyl)piperazine-1-yl)methyl}phenyl]methanone, which was dissolved in dilute hydrochloric acid (0.5 N, 1 mL) and lyophilized to give [4,5-bis-(4-chloro-phenyl)-2-(2-ethoxy-5-trifluoromethyl-phenyl)-4,5-dihydro-imidazol-1-yl]-[4-{(4-(2-hydroxyethyl)piperazine-1-yl)methyl}phenyl]methanone hydrochloride as a off-white powder (21 mg, 98%). LR-MS (APCI): 726.1 [(M+H)$^+$].

EXAMPLE 15

4-{2-[4,5-Bis-(4-chloro-phenyl)-2-(2-ethoxy-4-trifluoromethyl-phenyl)-4,5-dihydro-imidazole-1-sulfonyl]-ethyl}-morpholine hydrochloride

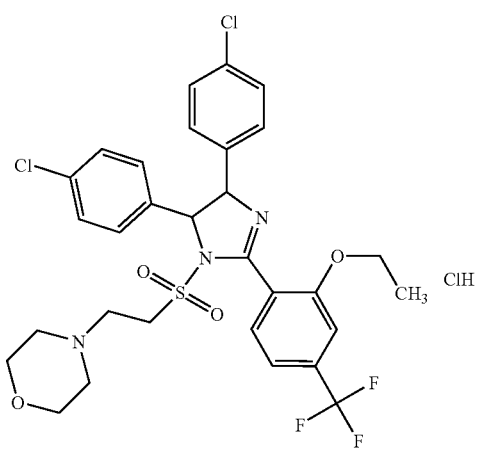

2-Chloroethylsulfonyl chloride (0.26 mL, 2.5 mmol) was added to a cooled (0° C.) solution of triethylamine (0.24 mL, 1.67 mmol) and 4,5-bis-(4-chloro-phenyl)-2-(2-ethoxy-4-trifluoromethyl-phenyl)-4,5-dihydro-1H-imidazole (400 mg, 0834 mmol, example 1) in methylene chloride (20 mL). The reaction mixture was stirred at room temperature for 3 h and quenched with saturated aqueous ammonium chloride. The aqueous phase was extracted with methylene chloride. The organic extracts were washed with water, brine, and dried over anhydrous sodium sulfate. The solvents were removed under reduced pressure and purification of the crude residue by flash chromatography over silica gel using 10-50% ethyl acetate in hexanes gave [4,5-bis-(4-chloro-phenyl)-2-(2-ethoxy-4-trifluoromethyl-phenyl)-4,5-dihydro-imidazol-1-yl]-[vinyl]sulfone (220 mg, 46%).

Morpholine (19 uL, 0.22 mmol) was added to a solution of [4,5-bis-(4-chloro-phenyl)-2-(2-ethoxy-4-trifluoromethyl-phenyl)-4,5-dihydro-imidazol-1-yl]-[vinyl]sulfone (40 mg, 0.07 mmol) in benzene (2.0 mL). The mixture was stirred overnight at 50° C. Evaporation of the solvents and chromatography of the residue over silica gel using 50-80% ethyl acetate in hexanes gave [4,5-bis-(4-chloro-phenyl)-2-(2-ethoxy-4-trifluoromethyl-phenyl)-4,5-dihydro-imidazol-1-yl]-[2-(morpholine-1-yl)ethyl]sulfone, which was dissolved in dilute hydrochloric acid (0.5 N, 1 mL) and lyophilized to give 4-{2-[4,5-bis-(4-chloro-phenyl)-2-(2-ethoxy-4-trifluoromethyl-phenyl)-4,5-dihydro-imidazole-1-sulfonyl]-ethyl}-morpholine hydrochloride as an off-white powder (25 mg). LR-MS: 656.2 [(M+H)$^+$].

EXAMPLE 16

1-[4,5-Bis-(4-chloro-phenyl)-2-(2-ethoxy-4-trifluoromethyl-phenyl)-4,5-dihydro-imidazole-1-carbonyl]-piperidine-4-carboxylic acid methyl ester was prepared in an analogous manner as described in example 5. LR-MS: 648.3 [(M+H)$^+$].

EXAMPLE 17

4,5-Bis-(4-chloro-phenyl)-2-(2-ethoxy-4-trifluoromethyl-phenyl)-4,5-dihydro-imidazole-1-carboxylic acid cyanomethyl-methyl-amide was prepared in an analogous manner as described in example 5. LR-MS: 575.2 [(M+H)$^+$].

EXAMPLE 18

[4,5-Bis-(4-chloro-phenyl)-2-(2-ethoxy-4-trifluoromethyl-phenyl)-4,5-dihydro-imidazol-1-yl]-(1,4-dioxa-8-azaspiro[4.5]dec-8-yl)-methanone was prepared in an analogous manner as described in example 5. LR-MS: 648.3 [(M+H)$^+$].

EXAMPLE 19

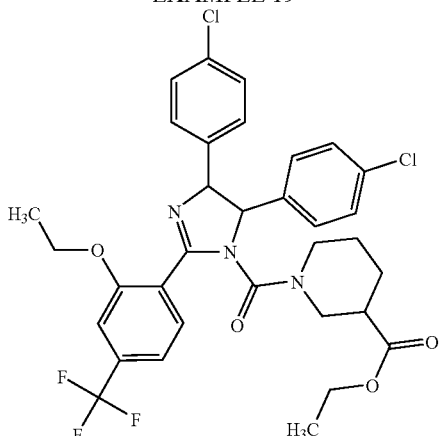

1-[4,5-Bis-(4-chloro-phenyl)-2-(2-ethoxy-4-trifluoromethyl-phenyl)-4,5-dihydro-imidazole-1-carbonyl]-piperidine-3-carboxylic acid ethyl ester was prepared in an analogous manner as described in example 5. LR-MS: 662.3 [(M+H)$^+$].

EXAMPLE 20

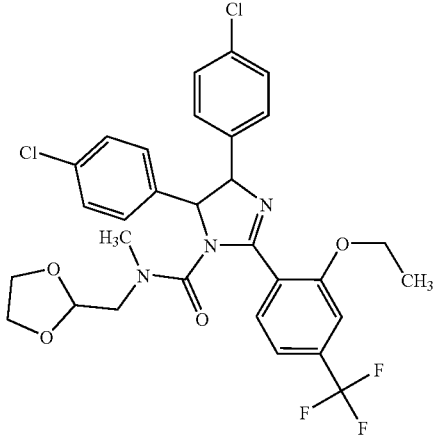

4,5-Bis-(4-chloro-phenyl)-2-(2-ethoxy-4-trifluoromethyl-phenyl)-4,5-dihydro-imidazole-1-carboxylic acid [1,3]dioxolan-2-ylmethyl-methyl-amide was prepared in an analogous manner as described in example 5. LR-MS: 622.2 [(M+H)$^+$].

EXAMPLE 21

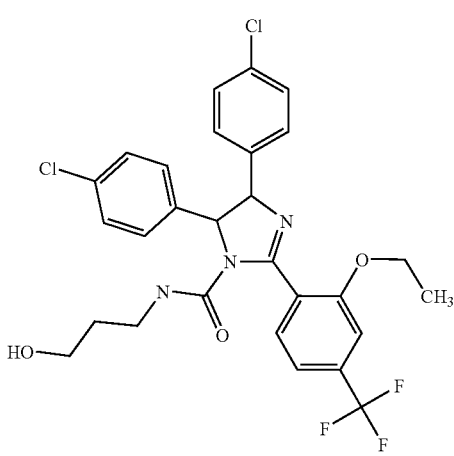

4,5-Bis-(4-chloro-phenyl)-2-(2-ethoxy-4-trifluoromethyl-phenyl)-4,5-dihydro-imidazole-1-carboxylic acid (3-hydroxy-propyl)-amide was prepared in an analogous manner as described in example 5. LR-MS: 580.2 [(M+H)$^+$].

EXAMPLE 22

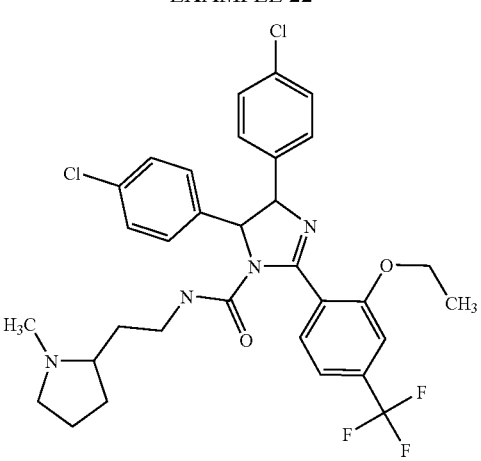

4,5-Bis-(4-chloro-phenyl)-2-(2-ethoxy-4-trifluoromethyl-phenyl)-4,5-dihydro-imidazole-1-carboxylic acid [2-(1-methyl-pyrrolidin-2-yl)-ethyl]-amide was prepared in an analogous manner as described in example 5. LR-MS: 633.3 [(M+H)$^+$].

EXAMPLE 23

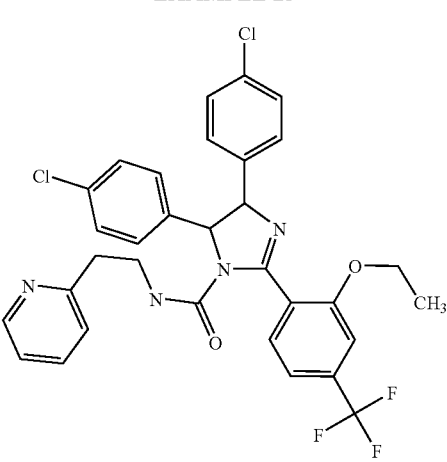

4,5-Bis-(4-chloro-phenyl)-2-(2-ethoxy-4-trifluoromethyl-phenyl)-4,5-dihydro-imidazole-1-carboxylic acid (2-pyridin-2-yl-ethyl)-amide was prepared in an analogous manner as described in example 5. LR-MS: 627.2 [(M+H)$^+$].

EXAMPLE 24

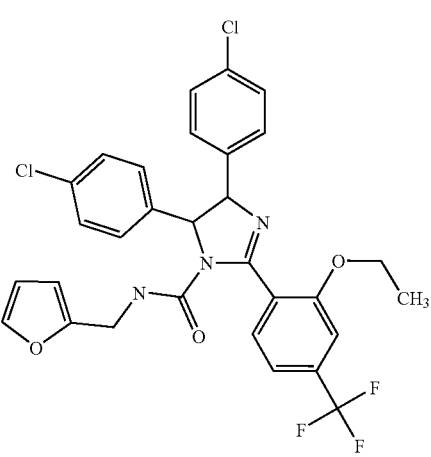

4,5-Bis-(4-chloro-phenyl)-2-(2-ethoxy-4-trifluoromethyl-phenyl)-4,5-dihydro-imidazole-1-carboxylic acid (furan-2-ylmethyl)-amide was prepared in an analogous manner as described in example 5. LR-MS: 602.2 [(M+H)$^+$].

EXAMPLE 25

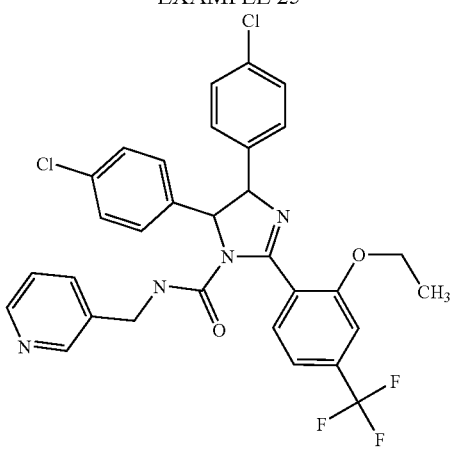

4,5-Bis-(4-chloro-phenyl)-2-(2-ethoxy-4-trifluoromethyl-phenyl)-4,5-dihydro-imidazole-1-carboxylic acid (pyridin-3-ylmethyl)-amide was prepared in an analogous manner as described in example 5. LR-MS: 613.2 [(M+H)+].

EXAMPLE 26

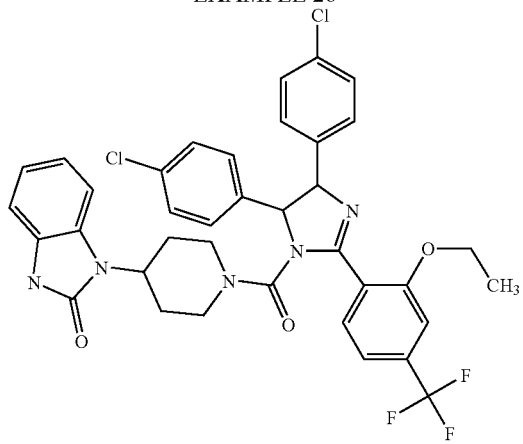

1-{1-[4,5-Bis-(4-chloro-phenyl)-2-(2-ethoxy-4-trifluoromethyl-phenyl)-4,5-dihydro-imidazole-1-carbonyl]-piperidin-4-yl}-1,3-dihydro-benzoimidazol-2-one was prepared in an analogous manner as described in example 5. LR-MS: 722.3 [(M+H)+].

EXAMPLE 27

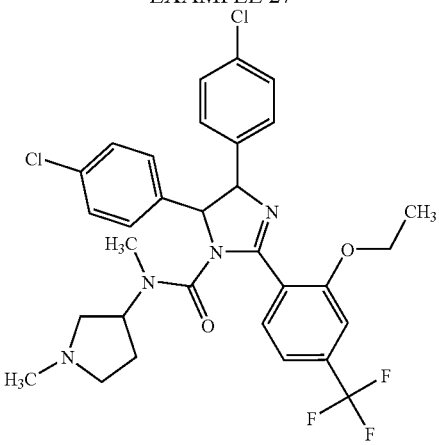

4,5-Bis-(4-chloro-phenyl)-2-(2-ethoxy-4-trifluoromethyl-phenyl)-4,5-dihydro-imidazole-1-carboxylic acid methyl-(1-methyl-pyrrolidin-3-yl)-amide was prepared in an analogous manner as described in example 5. LR-MS: 619.3 [(M+H)+].

EXAMPLE 28

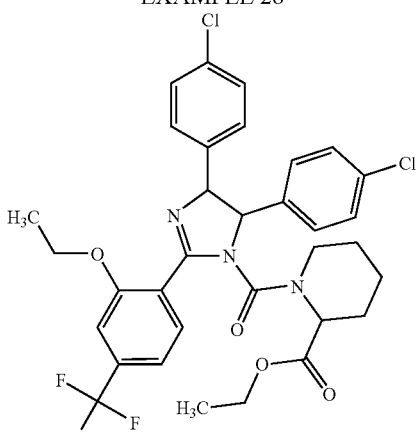

1-[4,5-Bis-(4-chloro-phenyl)-2-(2-ethoxy-4-trifluoromethyl-phenyl)-4,5-dihydro-imidazole-1-carbonyl]-piperidine-2-carboxylic acid ethyl ester was prepared in an analogous manner as described in example 5. LR-MS: 662.3 [(M+H)+].

EXAMPLE 29

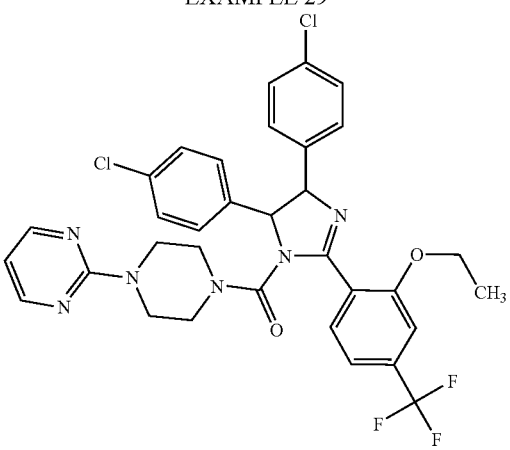

[4,5-Bis-(4-chloro-phenyl)-2-(2-ethoxy-4-trifluoromethyl-phenyl)-4,5-dihydro-imidazol-1-yl]-(4-pyrimidin-2-yl-piperazin-1-yl)-methanone was prepared in an analogous manner as described in example 5. LR-MS: 669.3 [(M+H)+].

EXAMPLE 30

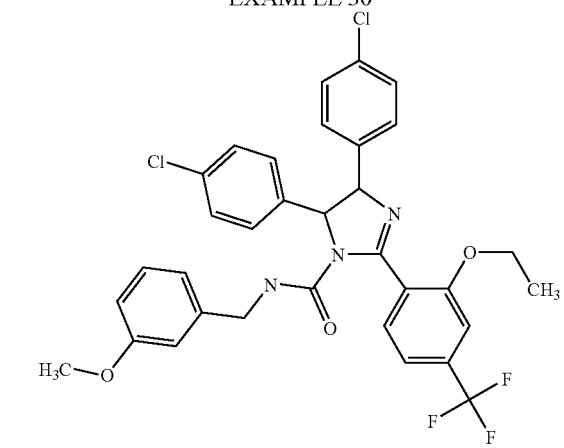

4,5-Bis-(4-chloro-phenyl)-2-(2-ethoxy-4-trifluoromethyl-phenyl)-4,5-dihydro-imidazole-1-carboxylic acid 3-methoxy-benzylamide was prepared in an analogous manner as described in example 5. LR-MS: 642.2 [(M+H)+].

EXAMPLE 31

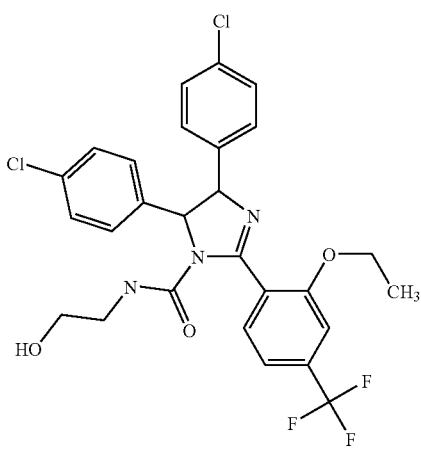

4,5-Bis-(4-chloro-phenyl)-2-(2-ethoxy-4-trifluoromethyl-phenyl)-4,5-dihydro-imidazole-1-carboxylic acid (2-hydroxy-ethyl)-amide was prepared in an analogous manner as described in example 5. LR-MS: 566.2 [(M+H)$^+$].

EXAMPLE 32

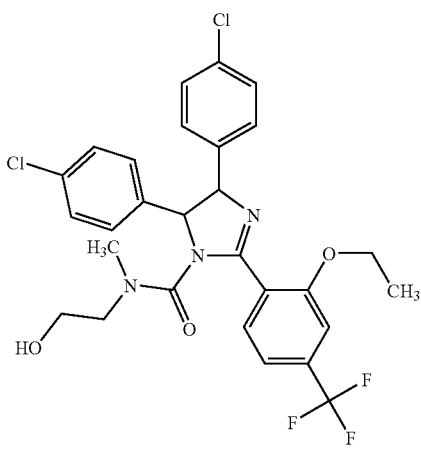

4,5-Bis-(4-chloro-phenyl)-2-(2-ethoxy-4-trifluoromethyl-phenyl)-4,5-dihydro-imidazole-1-carboxylic acid (2-hydroxy-ethyl)-methyl-amide was prepared in an analogous manner as described in example 5. LR-MS: 580.2 [(M+H)$^+$].

EXAMPLE 33

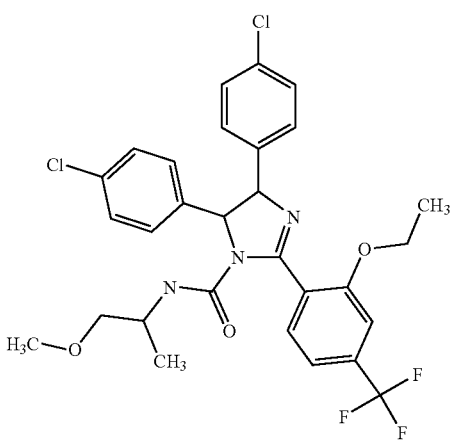

4,5-Bis-(4-chloro-phenyl)-2-(2-ethoxy-4-trifluoromethyl-phenyl)-4,5-dihydro-imidazole-1-carboxylic acid (2-methoxy-1-methyl-ethyl)-amide was prepared in an analogous manner as described in example 5. LR-MS: 594.2 [(M+H)$^+$].

EXAMPLE 34

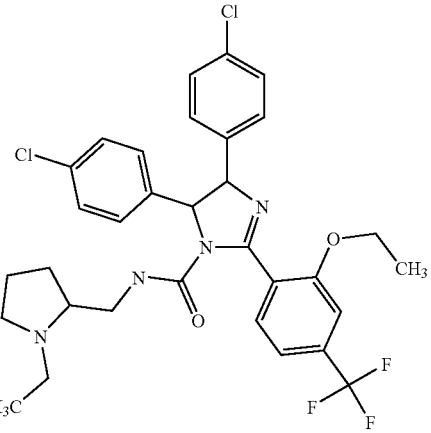

4,5-Bis-(4-chloro-phenyl)-2-(2-ethoxy-4-trifluoromethyl-phenyl)-4,5-dihydro-imidazole-1-carboxylic acid (1-ethyl-pyrrolidin-2-ylmethyl)-amide was prepared in an analogous manner as described in example 5. LR-MS: 633.3 [(M+H)$^+$].

EXAMPLE 35

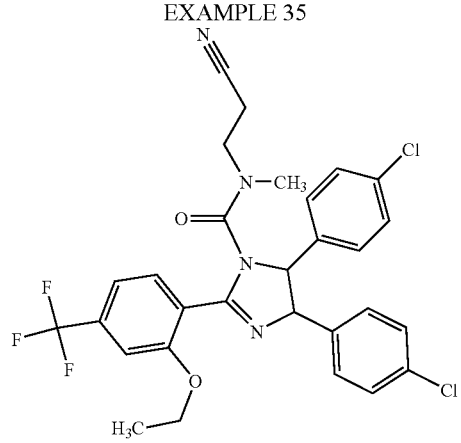

4,5-Bis-(4-chloro-phenyl)-2-(2-ethoxy-4-trifluoromethyl-phenyl)-4,5-dihydro-imidazole-1-carboxylic acid (2-cyano-ethyl)-methyl-amide was prepared in an analogous manner as described in example 5. LR-MS: 589.2 [(M+H)$^+$].

EXAMPLE 36

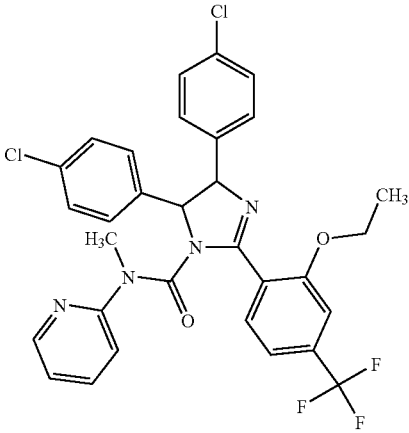

4,5-Bis-(4-chloro-phenyl)-2-(2-ethoxy-4-trifluoromethyl-phenyl)-4,5-dihydro-imidazole-1-carboxylic acid methyl-pyridin-2-yl-amide was prepared in an analogous manner as described in example 5. LR-MS: 613.47 [(M+H)$^+$].

EXAMPLE 37

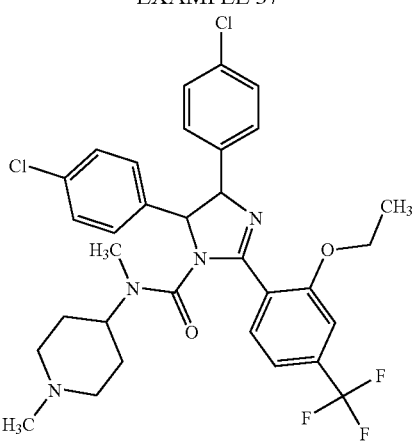

4,5-Bis-(4-chloro-phenyl)-2-(2-ethoxy-4-trifluoromethyl-phenyl)-4,5-dihydro-imidazole-1-carboxylic acid methyl-(1-methyl-piperidin-4-yl)-amide was prepared in an analogous manner as described in example 5. LR-MS: 633.3 [(M+H)$^+$].

EXAMPLE 38

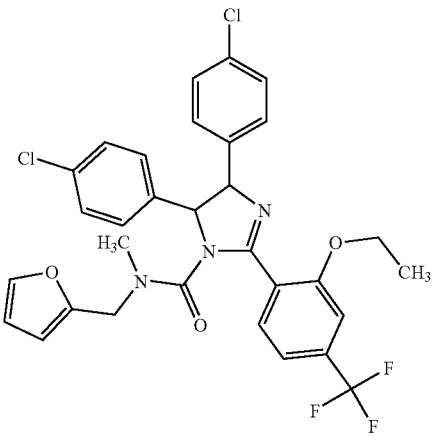

4,5-Bis-(4-chloro-phenyl)-2-(2-ethoxy-4-trifluoromethyl-phenyl)-4,5-dihydro-imidazole-1-carboxylic acid furan-2-ylmethyl-methyl-amide was prepared in an analogous manner as described in example 5. LR-MS: 616.3 [(M+H)$^+$].

EXAMPLE 39

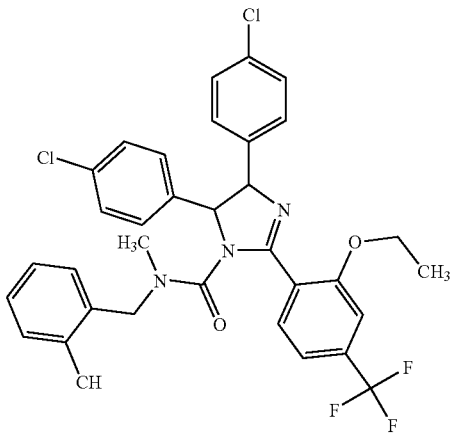

4,5-Bis-(4-chloro-phenyl)-2-(2-ethoxy-4-trifluoromethyl-phenyl)-4,5-dihydro-imidazole-1-carboxylic acid (2-hydroxy-benzyl)-methyl-amide was prepared in an analogous manner as described in example 5. LR-MS: 642.3 [(M+H)$^+$].

EXAMPLE 40

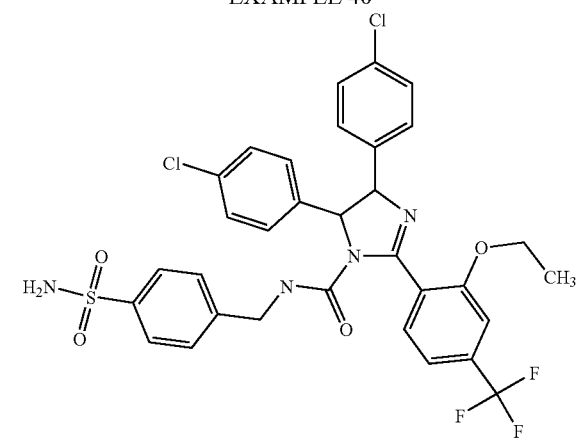

4,5-Bis-(4-chloro-phenyl)-2-(2-ethoxy-4-trifluoromethyl-phenyl)-4,5-dihydro-imidazole-1-carboxylic acid 4-sulfamoyl-benzylamide was prepared in an analogous manner as described in example 5. LR-MS: 691.2 [(M+H)$^+$].

EXAMPLE 41

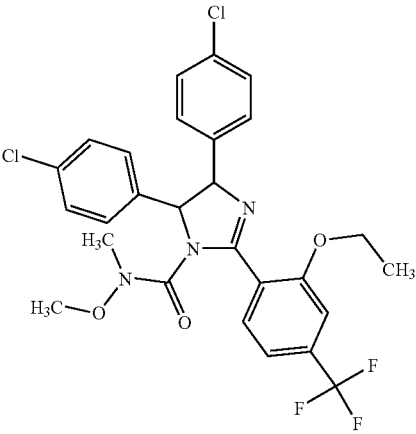

4,5-Bis-(4-chloro-phenyl)-2-(2-ethoxy-4-trifluoromethyl-phenyl)-4,5-dihydro-imidazole-1-carboxylic acid methoxy-methyl-amide was prepared in an analogous manner as described in example 5. LR-MS: 566.2 [(M+H)$^+$].

EXAMPLE 42

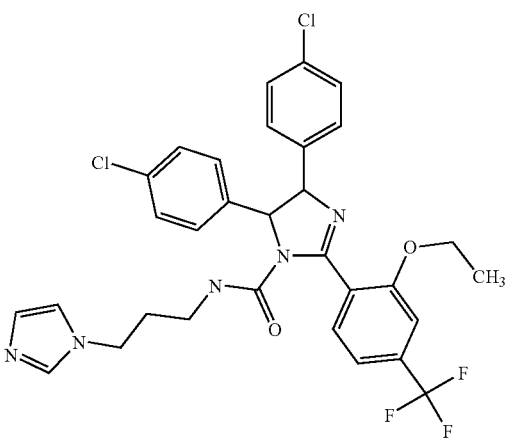

4,5-Bis-(4-chloro-phenyl)-2-(2-ethoxy-4-trifluoromethyl-phenyl)-4,5-dihydro-imidazole-1-carboxylic acid (3-imidazol-1-yl-propyl)-amide was prepared in an analogous manner as described in example 5. LR-MS: 630.3 [(M+H)$^+$].

EXAMPLE 43

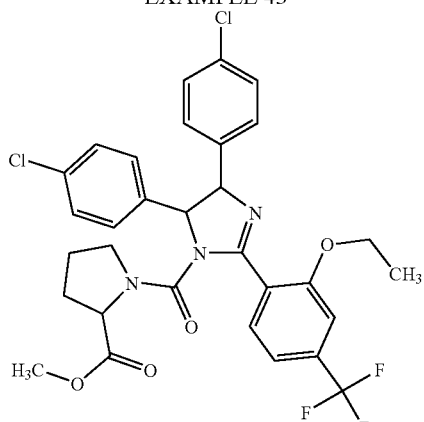

1-[4,5-Bis-(4-chloro-phenyl)-2-(2-ethoxy-4-trifluoromethyl-phenyl)-4,5-dihydro-imidazole-1-carbonyl]-pyrrolidine-2-carboxylic acid methyl ester was prepared in an analogous manner as described in example 5. LR-MS: 634.2 [(M+H)$^+$].

EXAMPLE 44

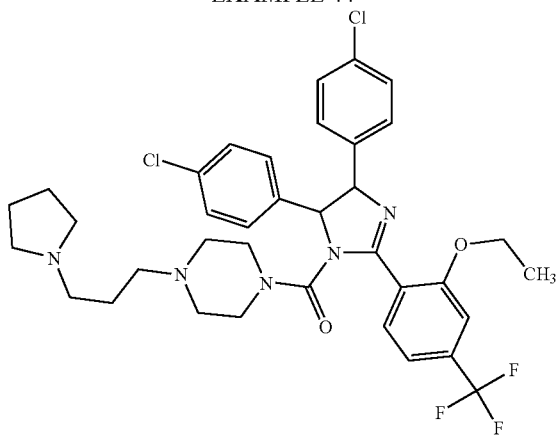

[4,5-Bis-(4-chloro-phenyl)-2-(2-ethoxy-4-trifluoromethyl-phenyl)-4,5-dihydro-imidazol-1-yl]-[4-(3-pyrrolidin-1-yl-propyl)-piperazin-1-yl]-methanone was prepared in an analogous manner as described in example 5. LR-MS: 702.5 [(M+H)$^+$].

EXAMPLE 45

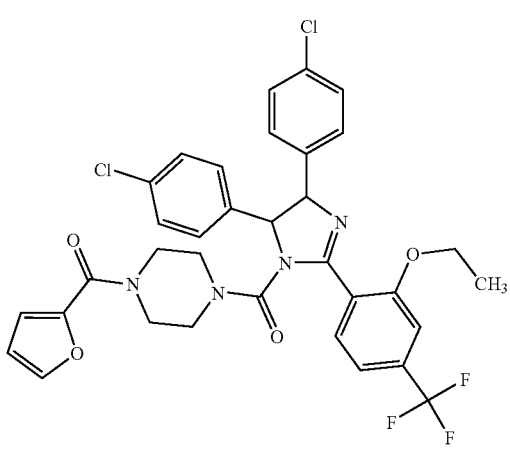

[4,5-Bis-(4-chloro-phenyl)-2-(2-ethoxy-4-trifluoromethyl-phenyl)-4,5-dihydro-imidazol-1-yl]-[4-(furan-2-carbonyl)-piperazin-1-yl]-methanone was prepared in an analogous manner as described in example 5. LR-MS: 684.5 (M$^+$).

EXAMPLE 46

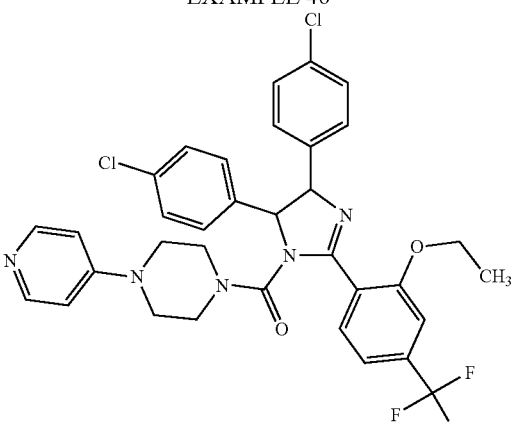

[4,5-Bis-(4-chloro-phenyl)-2-(2-ethoxy-4-trifluoromethyl-phenyl)-4,5-dihydro-imidazol-1-yl]-(4-pyridin-4-yl-piperazin-1-yl)-methanone was prepared in an analogous manner as described in example 5. LR-MS: 667.8 [(M+H)$^+$].

EXAMPLE 47

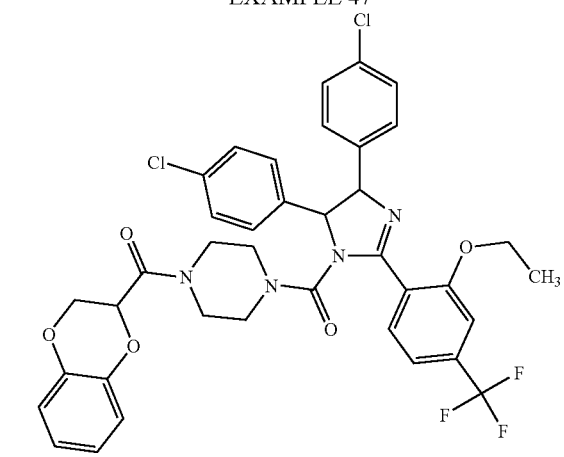

[4,5-Bis-(4-chloro-phenyl)-2-(2-ethoxy-4-trifluoromethyl-phenyl)-4,5-dihydro-imidazol-1-yl]-[4-(2,3-dihydro-benzo[1,4]dioxine-2-carbonyl)-piperazin-1-yl]-methanone was prepared in an analogous manner as described in example 5. LR-MS: 752.9 [(M+H)$^+$].

EXAMPLE 48

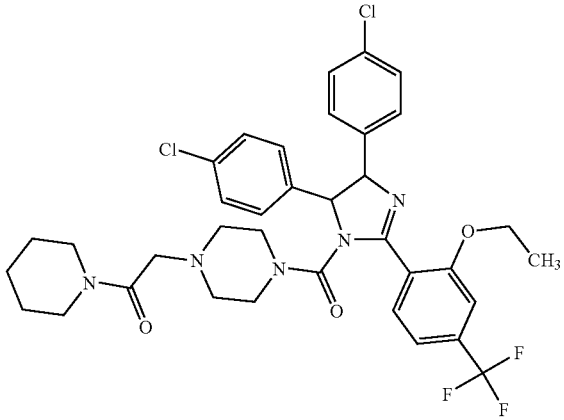

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-piperidin-1-yl-ethanone was prepared in an analogous manner as described in example 5. LR-MS: 715.9 [(M+H)$^+$].

EXAMPLE 49

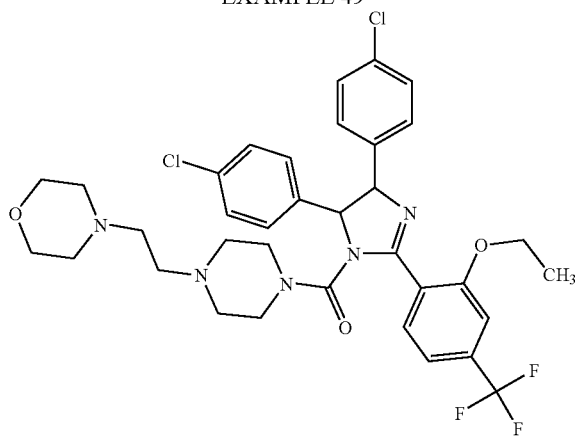

[4,5-Bis-(4-chloro-phenyl)-2-(2-ethoxy-4-trifluoromethyl-phenyl)-4,5-dihydro-imidazol-1-yl]-[4-(2-morpholin-4-yl-ethyl)-piperazin-1-yl]-methanone was prepared in an analogous manner as described in example 5. LR-MS: 704 [(M+H)+].

EXAMPLE 50

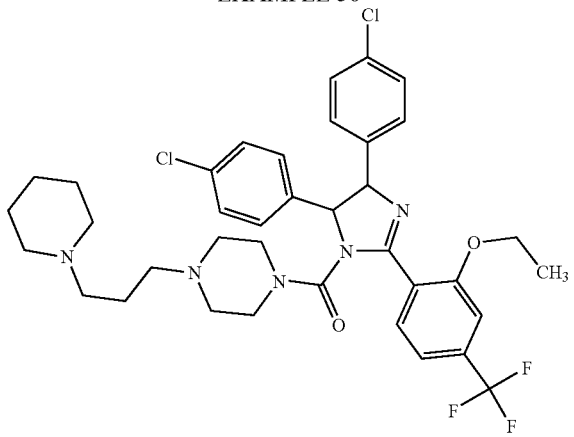

[4,5-Bis-(4-chloro-phenyl)-2-(2-ethoxy-4-trifluoromethyl-phenyl)-4,5-dihydro-imidazol-1-yl]-[4-(3-piperidin-1-yl-propyl)-piperazin-1-yl]-methanone was prepared in an analogous manner as described in example 5. LR-MS: 716 [(M+H)+].

EXAMPLE 51

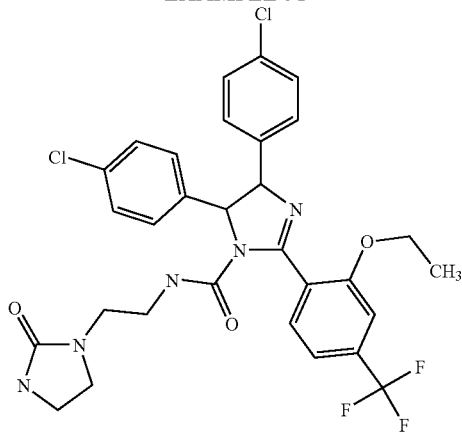

4,5-Bis-(4-chloro-phenyl)-2-(2-ethoxy-4-trifluoromethyl-phenyl)-4,5-dihydro-imidazole-1-carboxylic acid [2-(2-oxo-imidazolidin-1-yl)-ethyl]-amide was prepared in an analogous manner as described in example 5. LR-MS: 633.9 [(M+H)+].

EXAMPLE 52

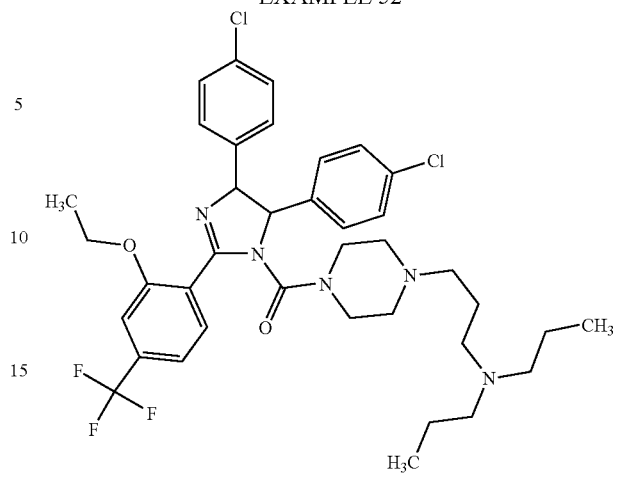

[4,5-Bis-(4-chloro-phenyl)-2-(2-ethoxy-4-trifluoromethyl-phenyl)-4,5-dihydro-imidazol-1-yl]-[4-(3-dipropylamino-propyl)-piperazin-1-yl]-methanone was prepared in an analogous manner as described in example 5. LR-MS: 732 [(M+H)+].

EXAMPLE 53

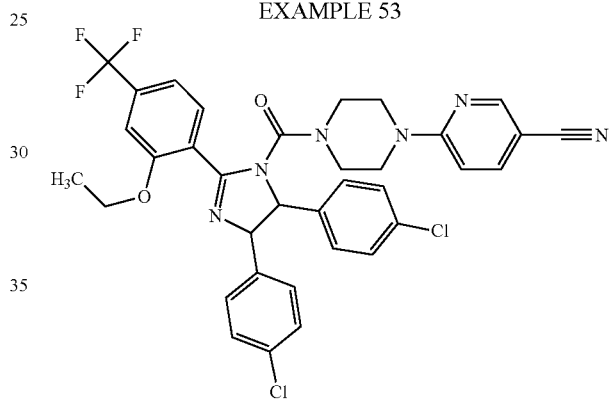

6-{4-[4,5-Bis-(4-chloro-phenyl)-2-(2-ethoxy-4-trifluoromethyl-phenyl)-4,5-dihydro-imidazole-1-carbonyl]-piperazin-1-yl}-nicotinonitrile was prepared in an analogous manner as described in example 5. LR-MS: 692.9 [(M+H)+].

EXAMPLE 54

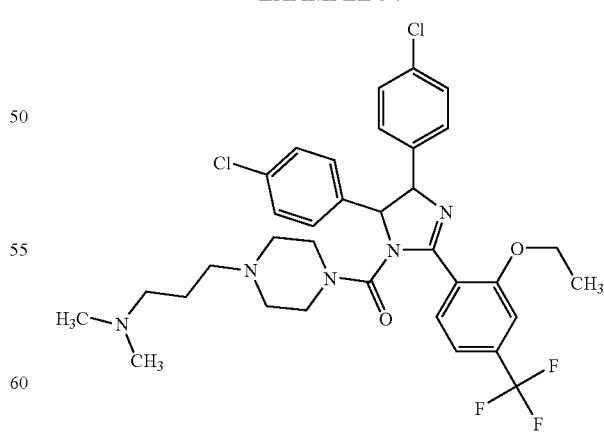

[4,5-Bis-(4-chloro-phenyl)-2-(2-ethoxy-4-trifluoromethyl-phenyl)-4,5-dihydro-imidazol-1-yl]-[4-(3-dimethylamino-propyl)-piperazin-1-yl]-methanone was prepared in an analogous manner as described in example 5. LR-MS: 675.9 [(M+H)+].

EXAMPLE 55

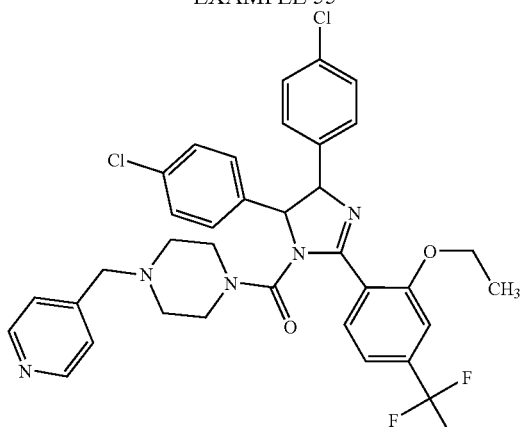

[4,5-Bis-(4-chloro-phenyl)-2-(2-ethoxy-4-trifluoromethyl-phenyl)-4,5-dihydro-imidazol-1-yl]-(4-pyridin-4-ylmethyl-piperazin-1-yl)-methanone was prepared in an analogous manner as described in example 5. LR-MS: 682.4 [(M+H)$^+$].

EXAMPLE 56

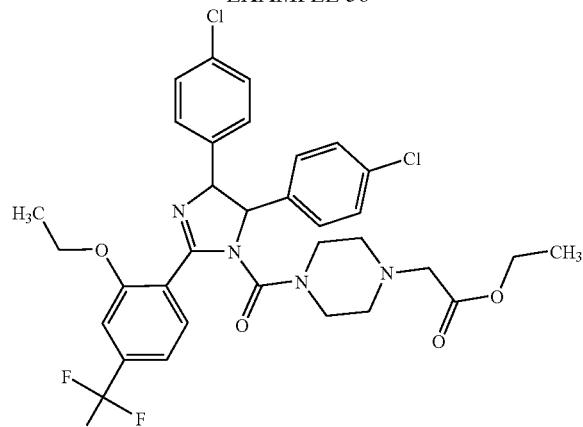

{4-[4,5-Bis-(4-chloro-phenyl)-2-(2-ethoxy-4-trifluoromethyl-phenyl)-4,5-dihydro-imidazole-1-carbonyl]-piperazin-1-yl}-acetic acid ethyl ester was prepared in an analogous manner as described in example 5. LR-MS: 676.9 [(M+H)$^+$].

EXAMPLE 57

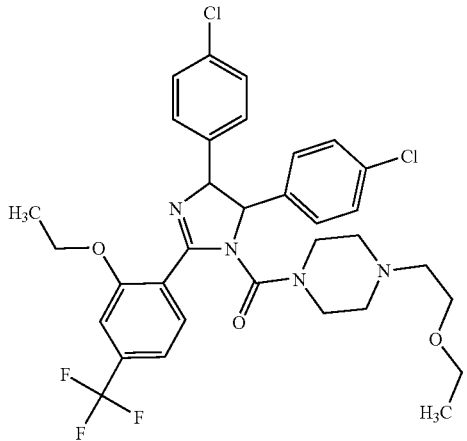

[4,5-Bis-(4-chloro-phenyl)-2-(2-ethoxy-4-trifluoromethyl-phenyl)-4,5-dihydro-imidazol-1-yl]-[4-(2-ethoxyethyl)-piperazin-1-yl]-methanone was prepared in an analogous manner as described in example 5. LR-MS: 662.9 [(M+H)$^+$].

EXAMPLE 58

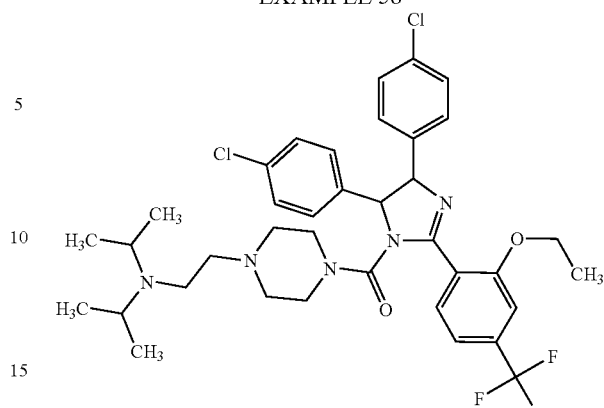

[4,5-Bis-(4-chloro-phenyl)-2-(2-ethoxy-4-trifluoromethyl-phenyl)-4,5-dihydro-imidazol-1-yl]-[4-(2-diisopropylamino-ethyl)-piperazin-1-yl]-methanone was prepared in an analogous manner as described in example 5. LR-MS: 718 [(M+H)$^+$].

EXAMPLE 59

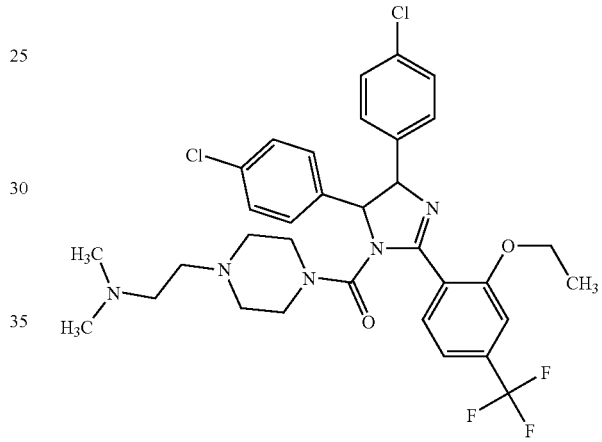

[4,5-Bis-(4-chloro-phenyl)-2-(2-ethoxy-4-trifluoromethyl-phenyl)-4,5-dihydro-imidazol-1-yl]-[4-(2-dimethylamino-ethyl)-piperazin-1-yl]-methanone was prepared in an analogous manner as described in example 5. LR-MS: 661.9 [(M+H)$^+$].

EXAMPLE 60

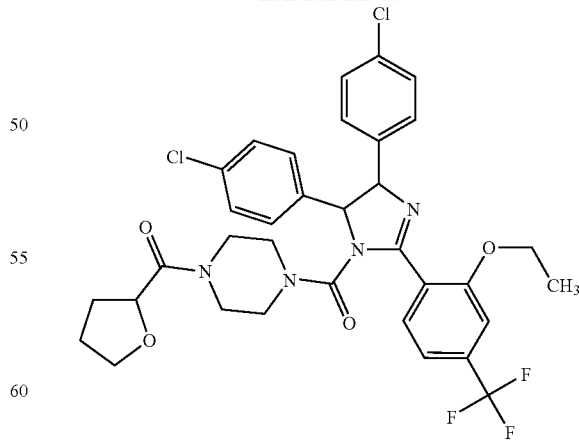

[4,5-Bis-(4-chloro-phenyl)-2-(2-ethoxy-4-trifluoromethyl-phenyl)-4,5-dihydro-imidazol-1-yl]-[4-(tetrahydro-furan-2-carbonyl)-piperazin-1-yl]-methanone was prepared in an analogous manner as described in example 5. LR-MS: 688.9 [(M+H)$^+$].

EXAMPLE 61

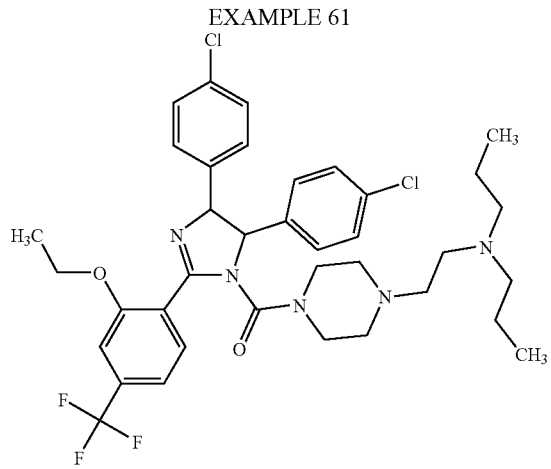

[4,5-Bis-(4-chloro-phenyl)-2-(2-ethoxy-4-trifluoromethyl-phenyl)-4,5-dihydro-imidazol-1-yl]-[4-(2-dipropylamino-ethyl)-piperazin-1-yl]-methanone was prepared in an analogous manner as described in example 5. LR-MS: 718 [(M+H)+].

EXAMPLE 62

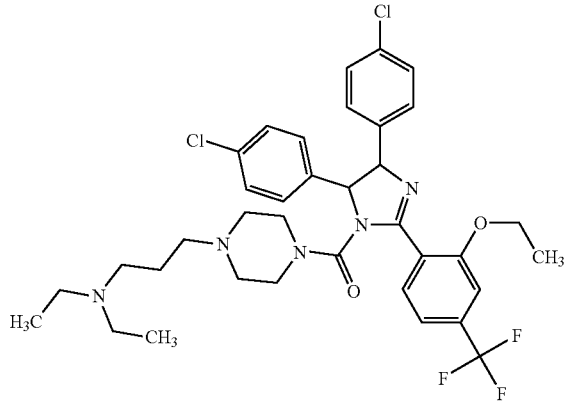

[4,5-Bis-(4-chloro-phenyl)-2-(2-ethoxy-4-trifluoromethyl-phenyl)-4,5-dihydro-imidazol-1-yl]-[4-(3-diethylamino-propyl)-piperazin-1-yl]-methanone was prepared in an analogous manner as described in example 5. LR-MS: 704 [(M+H)+].

EXAMPLE 63

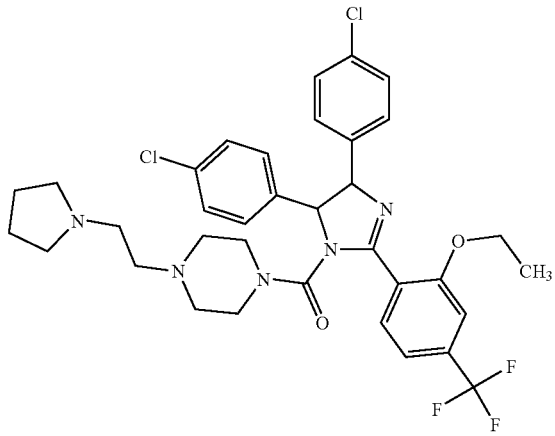

[4,5-Bis-(4-chloro-phenyl)-2-(2-ethoxy-4-trifluoromethyl-phenyl)-4,5-dihydro-imidazol-1-yl]-[4-(2-pyrrolidin-1-yl-ethyl)-piperazin-1-yl]-methanone was prepared in an analogous manner as described in example 5. LR-MS: 688 [(M+H)+].

EXAMPLE 64

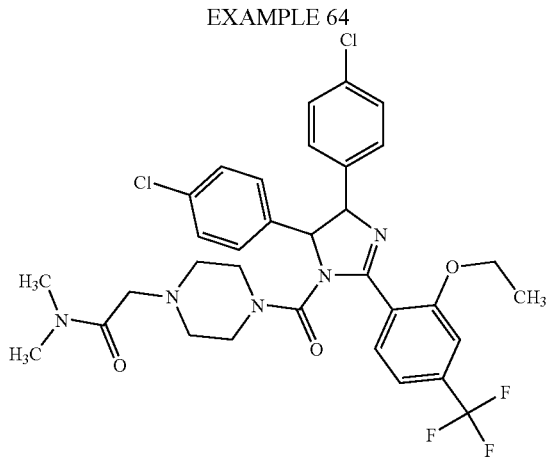

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N,N-dimethyl-acetamide was prepared in an analogous manner as described in example 5. LR-MS: 676.3 [(M+H)+].

EXAMPLE 65

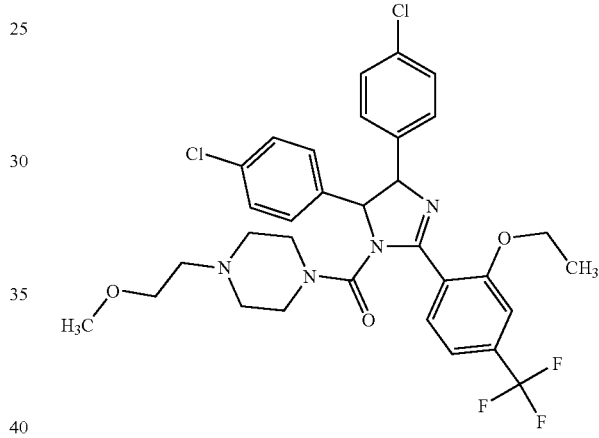

[4,5-Bis-(4-chloro-phenyl)-2-(2-ethoxy-4-trifluoromethyl-phenyl)-4,5-dihydro-imidazol-1-yl]-[4-(2-methoxy-ethyl)-piperazin-1-yl]-methanone was prepared in an analogous manner as described in example 5. LR-MS: 648.9 [(M+H)+].

EXAMPLE 66

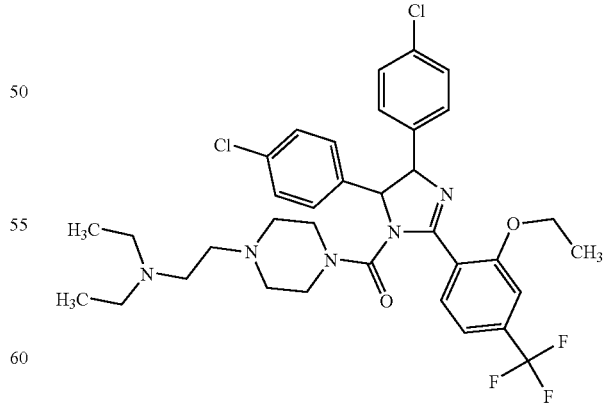

[4,5-Bis-(4-chloro-phenyl)-2-(2-ethoxy-4-trifluoromethyl-phenyl)-4,5-dihydro-imidazol-1-yl]-[4-(2-diethylamino-ethyl)-piperazin-1-yl]-methanone was prepared in an analogous manner as described in example 5. LR-MS: 690 [(M+H)+].

EXAMPLE 67

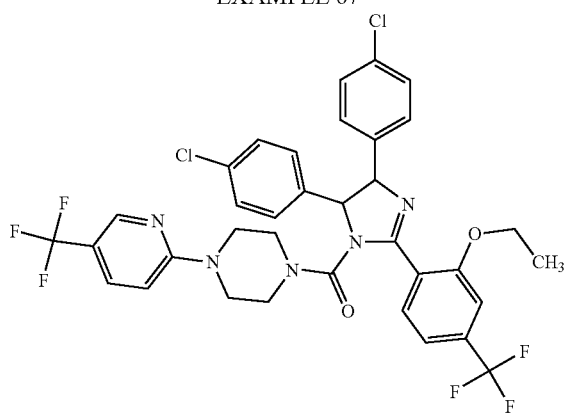

[4,5-Bis-(4-chloro-phenyl)-2-(2-ethoxy-4-trifluoromethyl-phenyl)-4,5-dihydro-imidazol-1-yl]-[4-(5-trifluoromethyl-pyridin-2-yl)-piperazin-1-yl]-methanone was prepared in an analogous manner as described in example 5. LR-MS: 735.9 [(M+H)$^+$].

EXAMPLE 68

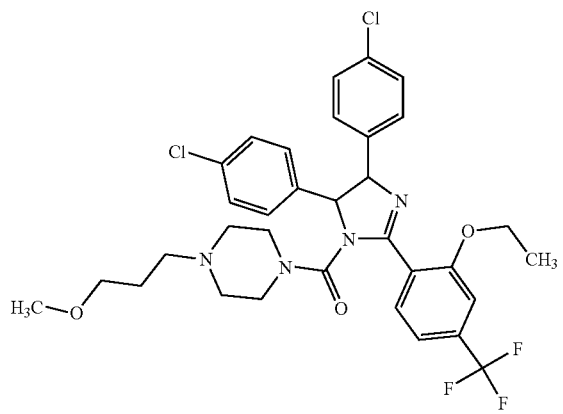

[4,5-Bis-(4-chloro-phenyl)-2-(2-ethoxy-4-trifluoromethyl-phenyl)-4,5-dihydro-imidazol-1-yl]-[4-(3-methoxypropyl)-piperazin-1-yl]-methanone was prepared in an analogous manner as described in example 5. LR-MS: 662.9 [(M+H)$^+$].

EXAMPLE 69

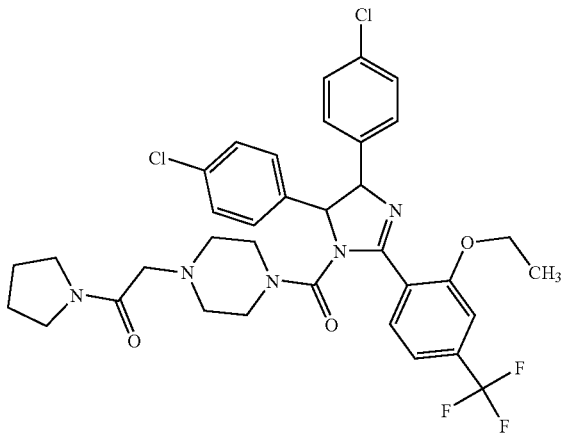

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-pyrrolidin-1-yl-ethanone was prepared in an analogous manner as described in example 5. LR-MS: 701.9 [(M+H)$^+$].

EXAMPLE 70

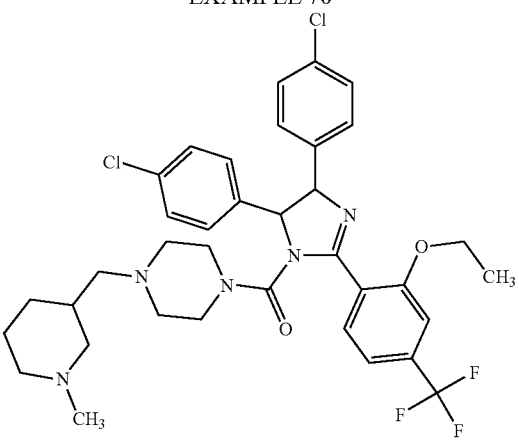

[4,5-Bis-(4-chloro-phenyl)-2-(2-ethoxy-4-trifluoromethyl-phenyl)-4,5-dihydro-imidazol-1-yl]-[4-(1-methyl-piperidin-3-ylmethyl)-piperazin-1-yl]-methanone was prepared in an analogous manner as described in example 5. LR-MS: 702 [(M+H)$^+$].

EXAMPLE 71

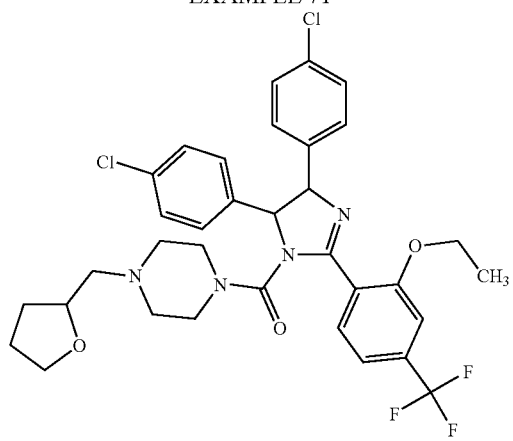

[4,5-Bis-(4-chloro-phenyl)-2-(2-ethoxy-4-trifluoromethyl-phenyl)-4,5-dihydro-imidazol-1-yl]-[4-(tetrahydro-furan-2-ylmethyl)-piperazin-1-yl]-methanone was prepared in an analogous manner as described in example 5. LR-MS: 675 [(M+H)$^+$].

EXAMPLE 72

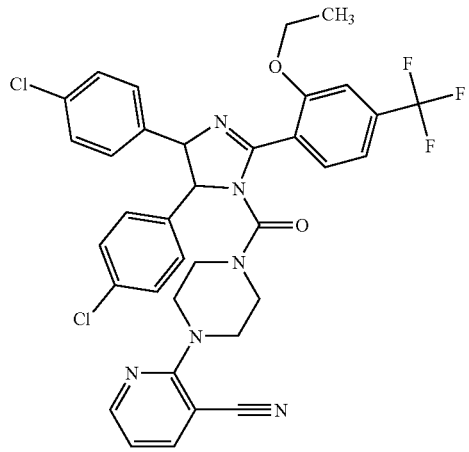

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-nicotinonitrile was prepared in an analogous manner as described in example 5. LR-MS: 692.9 [(M+H)$^+$].

EXAMPLE 73

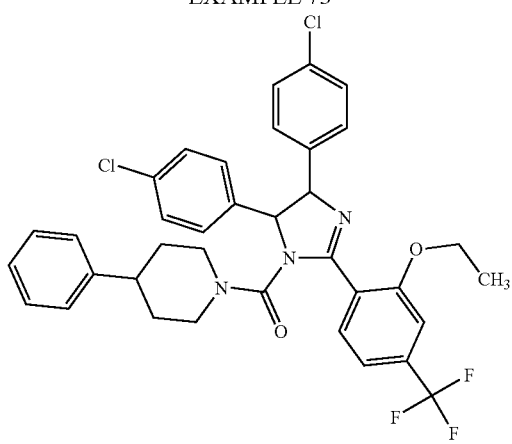

[4,5-Bis-(4-chloro-phenyl)-2-(2-ethoxy-4-trifluoromethyl-phenyl)-4,5-dihydro-imidazol-1-yl]-(4-phenyl-piperidin-1-yl)-methanone was prepared in an analogous manner as described in example 5. LR-MS: 665.9 [(M+H)+].

EXAMPLE 74

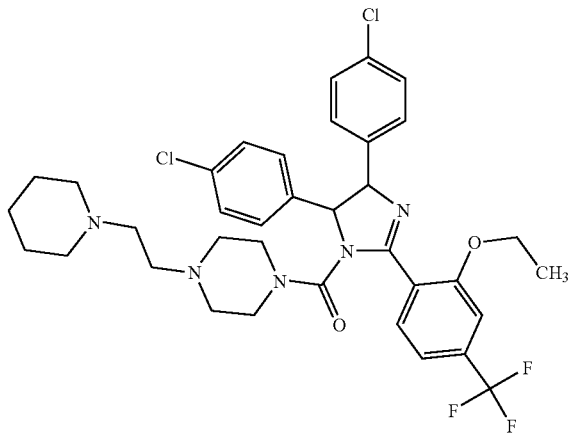

[4,5-Bis-(4-chloro-phenyl)-2-(2-ethoxy-4-trifluoromethyl-phenyl)-4,5-dihydro-imidazol-1-yl]-[4-(2-piperidin-1-yl-ethyl)-piperazin-1-yl]-methanone was prepared in an analogous manner as described in example 5. LR-MS: 702.5 [(M+H)+].

EXAMPLE 75

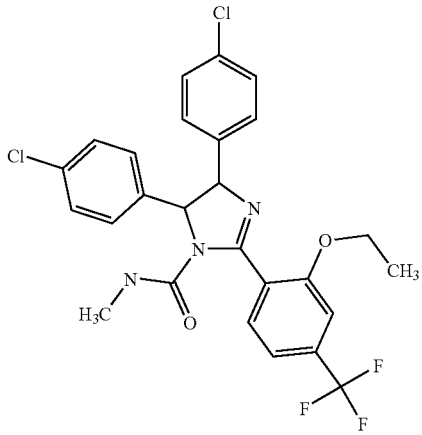

4,5-Bis-(4-chloro-phenyl)-2-(2-ethoxy-4-trifluoromethyl-phenyl)-4,5-dihydro-imidazole-1-carboxylic acid methylamide was prepared in an analogous manner as described in example 5. LR-MS: 535.8 [(M+H)+].

EXAMPLE 76

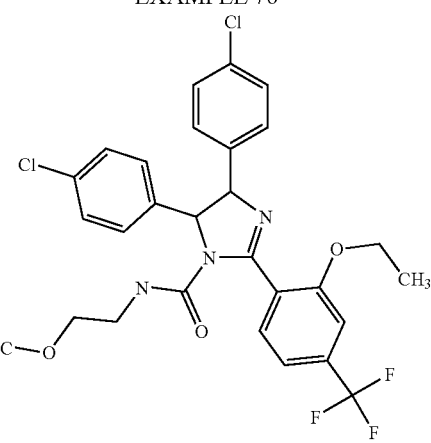

4,5-Bis-(4-chloro-phenyl)-2-(2-ethoxy-4-trifluoromethyl-phenyl)-4,5-dihydro-imidazole-1-carboxylic acid (2-methoxy-ethyl)-amide was prepared in an analogous manner as described in example 5. LR-MS: 579.9 [(M+H)+].

EXAMPLE 77

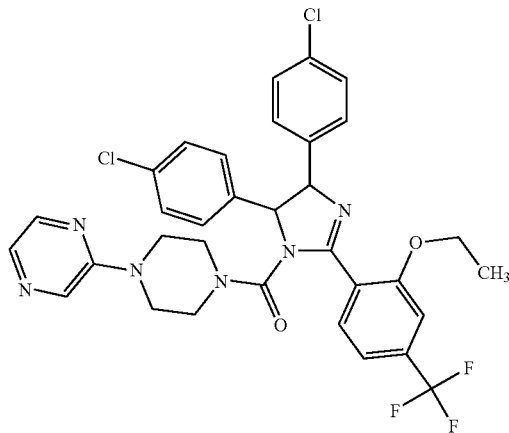

[4,5-Bis-(4-chloro-phenyl)-2-(2-ethoxy-4-trifluoromethyl-phenyl)-4,5-dihydro-imidazol-1-yl]-(2,3,5,6-tetrahydro-[1,2']bipyrazinyl-4-yl)-methanone as prepared in an analogous manner as described in example 5. LR-MS: 669.4 [(M+H)+].

EXAMPLE 78

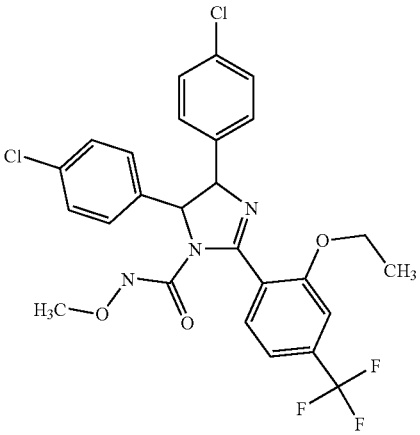

4,5-Bis-(4-chloro-phenyl)-2-(2-ethoxy-4-trifluoromethyl-phenyl)-4,5-dihydro-imidazole-1-carboxylic acid methoxy-amide was prepared in an analogous manner as described in example 5. LR-MS: 551.8 [(M+H)+].

EXAMPLE 79

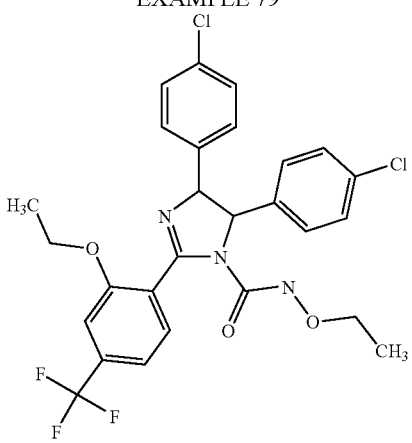

4,5-Bis-(4-chloro-phenyl)-2-(2-ethoxy-4-trifluoromethyl-phenyl)-4,5-dihydro-imidazole-1-carboxylic acid ethoxy-amide was prepared in an analogous manner as described in example 5. LR-MS: 565.9 [(M+H)+].

EXAMPLE 80

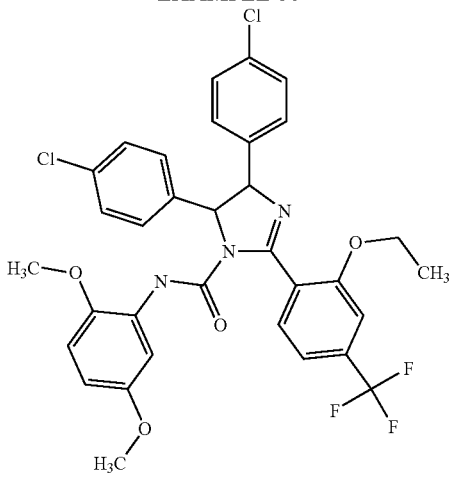

4,5-Bis-(4-chloro-phenyl)-2-(2-ethoxy-4-trifluoromethyl-phenyl)-4,5-dihydro-imidazole-1-carboxylic acid (2,5-dimethoxy-phenyl)-amide was prepared in an analogous manner as described in example 5. LR-MS: 657.9 [(M+H)+].

EXAMPLE 81

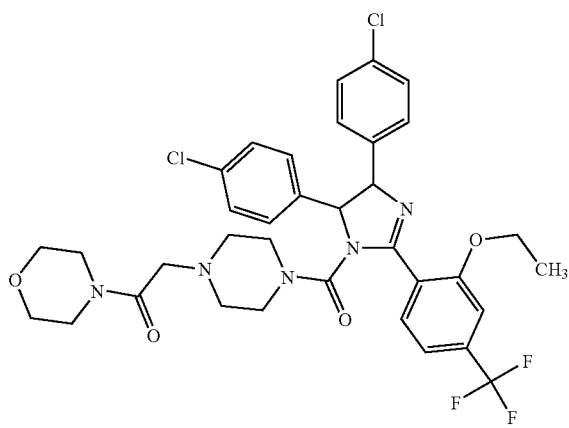

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-morpholin-4-yl-ethanone was prepared in an analogous manner as described in example 5. LR-MS: 718.4 [(M+H)+].

EXAMPLE 82

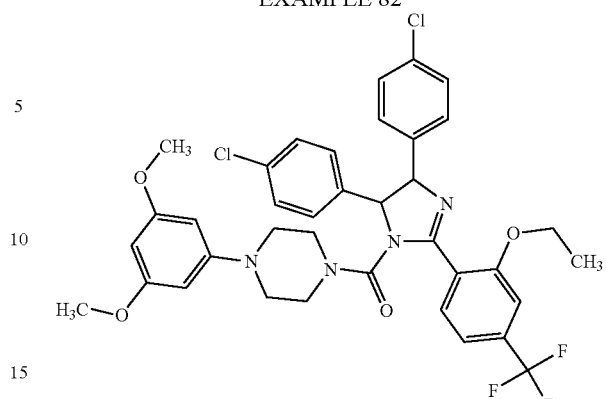

[4,5-Bis-(4-chloro-phenyl)-2-(2-ethoxy-4-trifluoromethyl-phenyl)-4,5-dihydro-imidazol-1'-yl]-[4-(3,5-dimethoxy-phenyl)-piperazin-1-yl]-methanone was prepared in an analogous manner as described in example 5. LR-MS: 727 [(M+H)+].

EXAMPLE 83

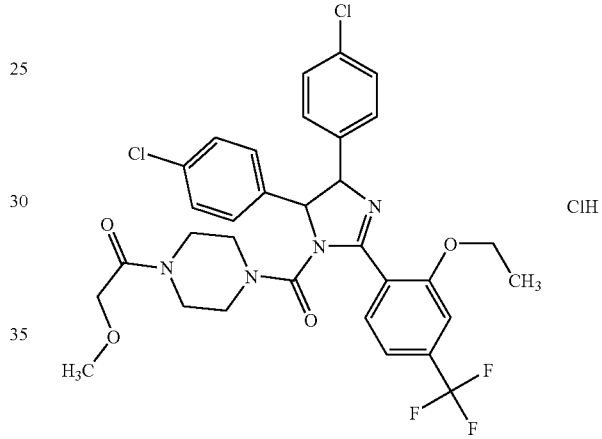

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-methoxy-ethanone hydrochloride was prepared in an analogous manner as described in example 5. LR-MS: 663.4 [(M+H)+].

EXAMPLE 84

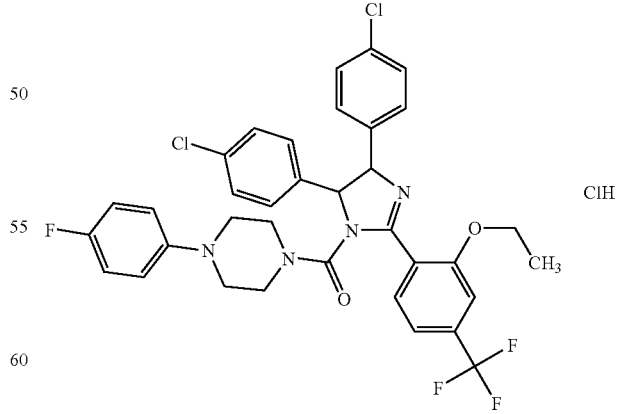

[4,5-Bis-(4-chloro-phenyl)-2-(2-ethoxy-4-trifluoromethyl-phenyl)-4,5-dihydro-imidazol-1-yl]-[4-(4-fluoro-phenyl)-piperazin-1-yl]-methanone hydrochloride was prepared in an analogous manner as described in example 5. LR-MS: 685.3 [(M+H)+].

EXAMPLE 85

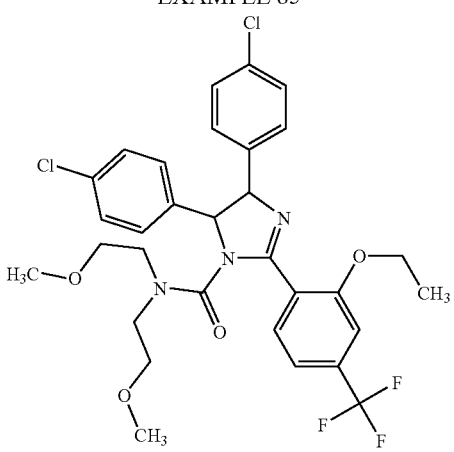

4,5-Bis-(4-chloro-phenyl)-2-(2-ethoxy-4-trifluoromethyl-phenyl)-4,5-dihydro-imidazole-1-carboxylic acid bis-(2-methoxy-ethyl)-amide was prepared in an analogous manner as described in example 5. LR-MS: 638.3 [(M+H)$^+$].

EXAMPLE 86

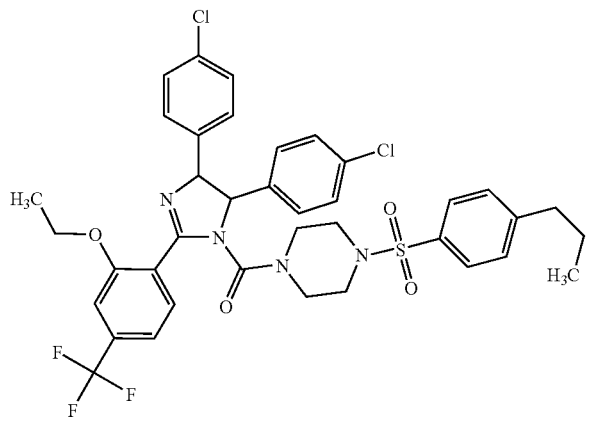

4,5-Bis-(4-chloro-phenyl)-2-(2-ethoxy-4-trifluoromethyl-phenyl)-4,5-dihydro-imidazol-1-yl]-[4-(4-propyl-benzene-sulfonyl)-piperazin-1-yl]-methanone was prepared in an analogous manner as described in example 6. LR-MS: 773.5 [(M+H)$^+$].

EXAMPLE 87

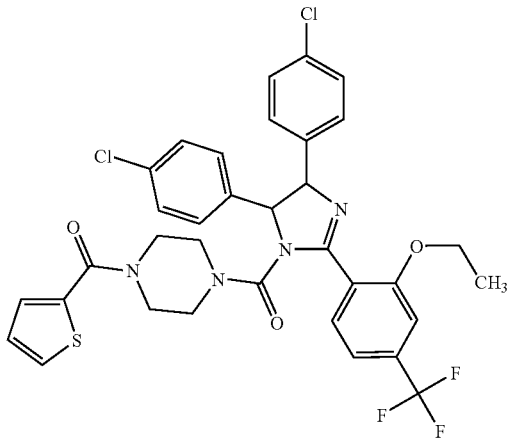

[4,5-Bis-(4-chloro-phenyl)-2-(2-ethoxy-4-trifluoromethyl-phenyl-4,5-dihydro-imidazol-1-yl]-[4-(thiophene-2-carbonyl)-piperazin-1-yl]-methanone was prepared in an analogous manner as described in example 6. LR-MS: 701.4 [(M+H)$^+$].

EXAMPLE 88

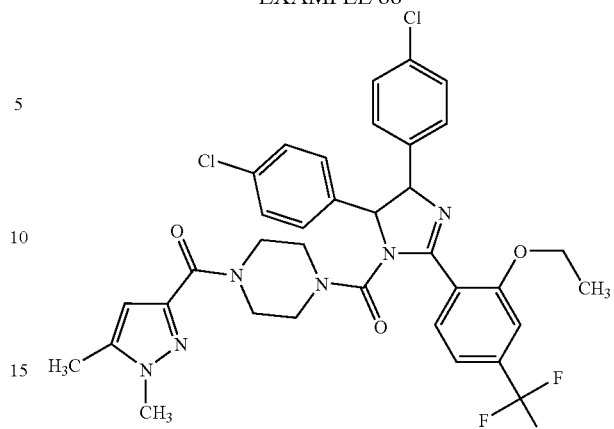

[4,5-Bis-(4-chloro-phenyl)-2-(2-ethoxy-4-trifluorom-ethyl-phenyl)-4,5-dihydro-imidazol-1-yl]-[4-(1,5-dimethyl-1H-pyrazole-3-carbonyl)-piperazin-1-yl]-methanone was prepared in an analogous manner as described in example 6. LR-MS: 713.4 [(M+H)$^+$].

EXAMPLE 89

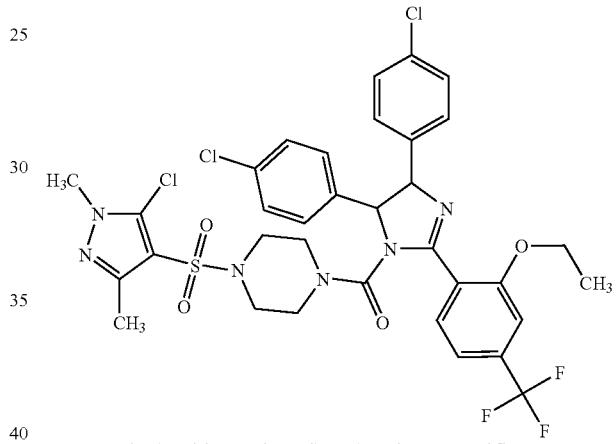

[4,5-Bis-(4-chloro-phenyl)-2-(2-ethoxy-4-trifluorom-ethyl-phenyl)-4,5-dihydro-imidazol-1-yl]-[4-(5-chloro-1,3-dimethyl-1H-pyrazole-4-sulfonyl)-piperazin-1-yl]-metha-none was prepared in an analogous manner as described in example 6. LR-MS: 783.50 [(M+H)$^+$].

EXAMPLE 90

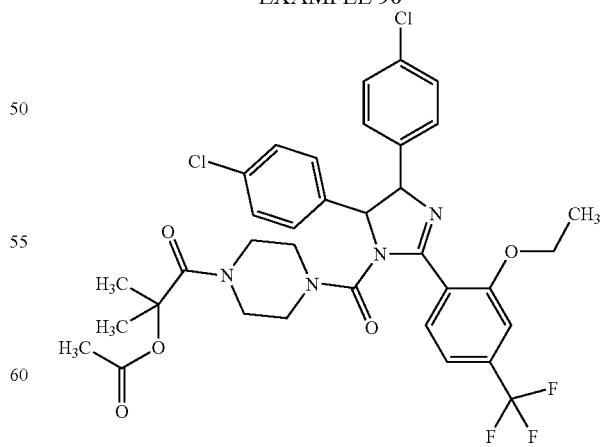

Acetic acid 2-{4-[4,5-bis-(4-chloro-phenyl)-2-(2-ethoxy-4-trifluoromethyl-phenyl)-4,5-dihydro-imidazole-1-carbo-nyl]-piperazin-1-yl}-1,1-dimethyl-2-oxo-ethyl ester was prepared in an analogous manner as described in example 6. LR-MS: 719.5 [(M+H)$^+$].

EXAMPLE 91

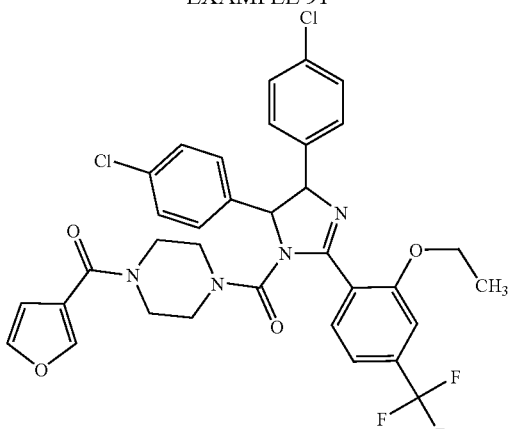

[4,5-Bis-(4-chloro-phenyl)-2-(2-ethoxy-4-trifluoromethyl-phenyl)-4,5-dihydro-imidazol-1-yl]-[4-(furan-3-carbonyl)-piperazin-1-yl]-methanone was prepared in an analogous manner as described in example 6. LR-MS: 685.4 [(M+H)$^+$].

EXAMPLE 92

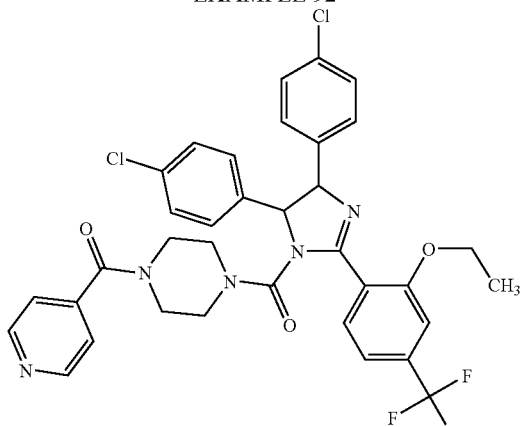

[4,5-Bis-(4-chloro-phenyl)-2-(2-ethoxy-4-trifluoromethyl-phenyl)-4,5-dihydro-imidazol-1-yl]-[4-(pyridine-4-carbonyl)-piperazin-1-yl]-methanone was prepared in an analogous manner as described in example 6. LR-MS: 696.4 [(M+H)$^+$].

EXAMPLE 93

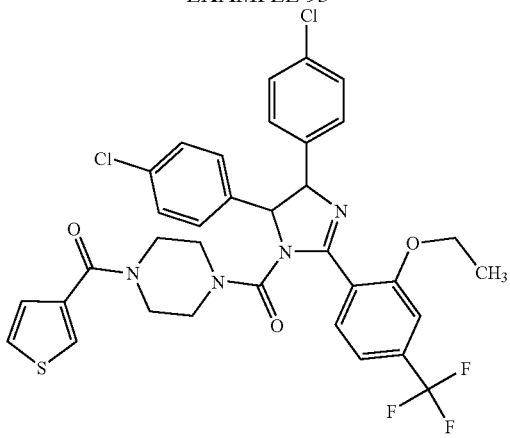

[4,5-Bis-(4-chloro-phenyl)-2-(2-ethoxy-4-trifluoromethyl-phenyl)-4,5-dihydro-imidazol-1-yl]-[4-(thiophene-3-carbonyl)-piperazin-1-yl]-methanone was prepared in an analogous manner as described in example 6. LR-MS: 701.4 [(M+H)$^+$].

EXAMPLE 94

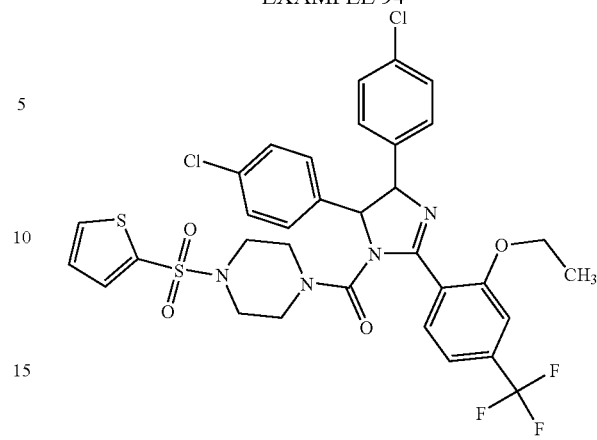

[4,5-Bis-(4-chloro-phenyl)-2-(2-ethoxy-4-trifluoromethyl-phenyl)-4,5-dihydro-imidazol-1-yl]-[4-(thiophene-2-sulfonyl)-piperazin-1-yl]-methanone was prepared in an analogous manner as described in example 6. LR-MS: 737.4 [(M+H)$^+$].

EXAMPLE 95

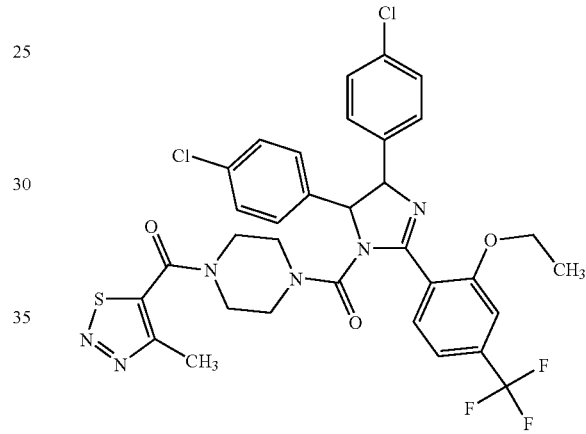

[4,5-Bis-(4-chloro-phenyl)-2-(2-ethoxy-4-trifluoromethyl-phenyl)-4,5-dihydro-imidazol-1-yl]-[4-(4-methyl-[1,2,3]thiadiazole-5-carbonyl)-piperazin-1-yl]-methanone was prepared in an analogous manner as described in example 6. LR-MS: 717.4 [(M+H)$^+$].

EXAMPLE 96

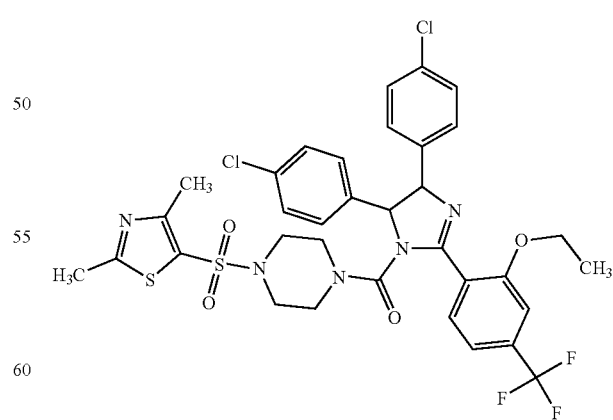

[4,5-Bis-(4-chloro-phenyl)-2-(2-ethoxy-4-trifluoromethyl-phenyl)-4,5-dihydro-imidazol-1-yl]-[4-(2,4-dimethyl-thiazole-5-sulfonyl)-piperazin-1-yl]-methanone was prepared in an analogous manner as described in example 6. LR-MS: 766.4 [(M+H)$^+$].

EXAMPLE 97

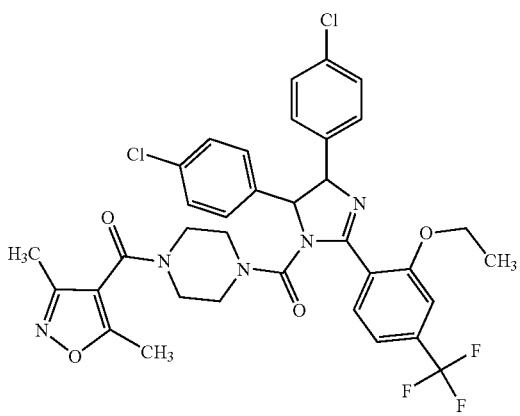

[4,5-Bis-(4-chloro-phenyl)-2-(2-ethoxy-4-trifluoromethyl-phenyl)-4,5-dihydro-imidazol-1-yl]-[4-(3,5-dimethyl-isoxazole-4-carbonyl)-piperazin-1-yl]-methanone was prepared in an analogous manner as described in example 6. LR-MS: 714.5 [(M+H)+].

EXAMPLE 98

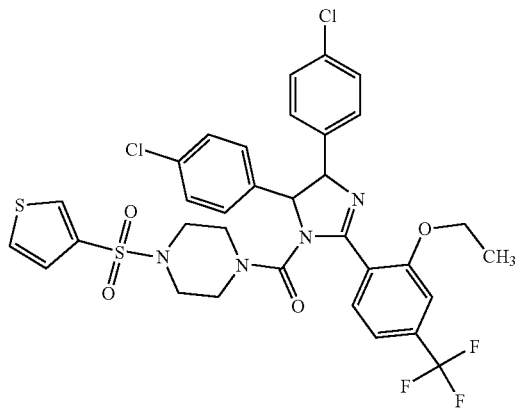

[4,5-Bis-(4-chloro-phenyl)-2-(2-ethoxy-4-trifluoromethyl-phenyl)-4,5-dihydro-imidazol-1-yl]-[4-(thiophene-3-sulfonyl)-piperazin-1-yl]-methanone was prepared in an analogous manner as described in example 6. LR-MS: 737.3 [(M+H)+].

EXAMPLE 99

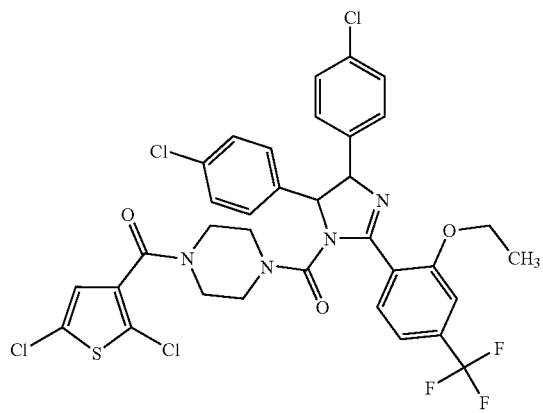

[4,5-Bis-(4-chloro-phenyl)-2-(2-ethoxy-4-trifluoromethyl-phenyl)-4,5-dihydro-imidazol-1-yl]-[4-(2,5-dichloro-thiophene-3-carbonyl)-piperazin-1-yl]-methanone was prepared in an analogous manner as described in example 6. LR-MS: 769.3 (M+).

EXAMPLE 100

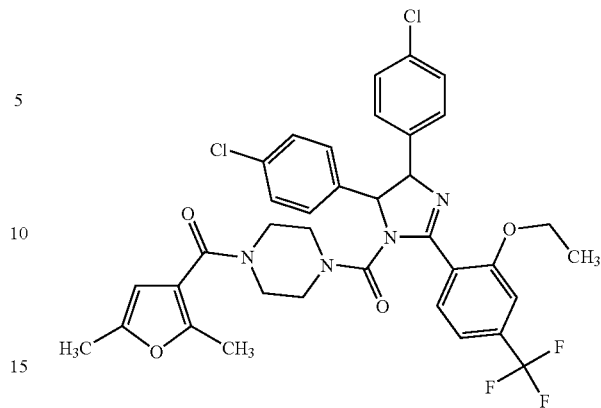

[4,5-Bis-(4-chloro-phenyl)-2-(2-ethoxy-4-trifluoromethyl-phenyl)-4,5-dihydro-imidazol-1-yl]-[4-(2,5-dimethyl-furan-3-carbonyl)-piperazin-1-yl]-methanone was prepared in an analogous manner as described in example 6. LR-MS: 713.5 [(M+H)+].

EXAMPLE 101

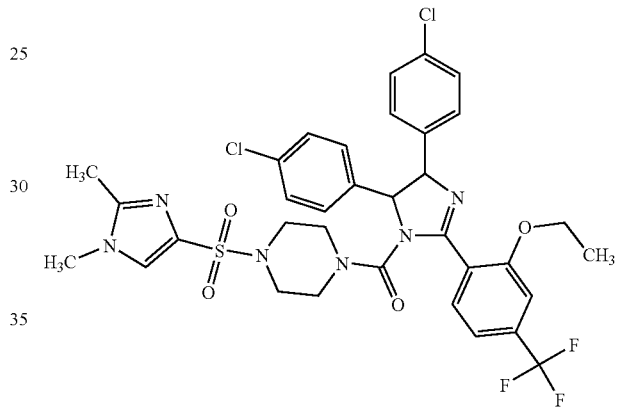

[4,5-Bis-(4-chloro-phenyl)-2-(2-ethoxy-4-trifluoromethyl-phenyl)-4,5-dihydro-imidazol-1-yl]-[4-(1,2-dimethyl-1H-imidazole-4-sulfonyl)-piperazin-1-yl]-methanone was prepared in an analogous manner as described in example 6. LR-MS: 749.4 [(M+H)+].

EXAMPLE 102

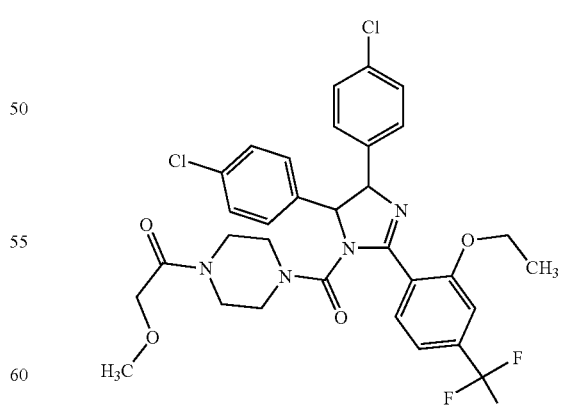

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-methoxy-ethanone was prepared in an analogous manner as described in example 6. LR-MS: 663.4 [(M+H)+].

EXAMPLE 103

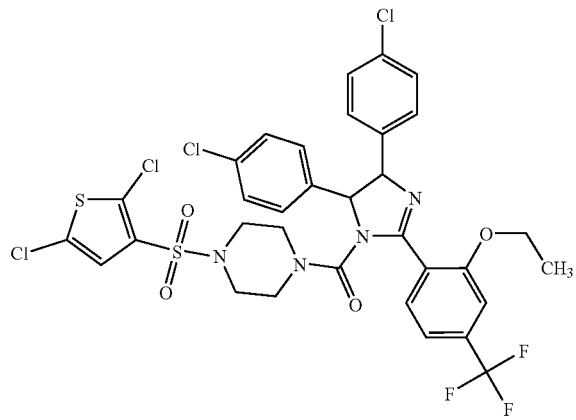

[4,5-Bis-(4-chloro-phenyl)-2-(2-ethoxy-4-trifluoromethyl-phenyl)-4,5-dihydro-imidazol-1-yl]-[4-(2,5-dichloro-thiophene-3-sulfonyl)-piperazin-1-yl]-methanone was prepared in an analogous manner as described in example 6. LR-MS: 805.3 (M+).

EXAMPLE 104

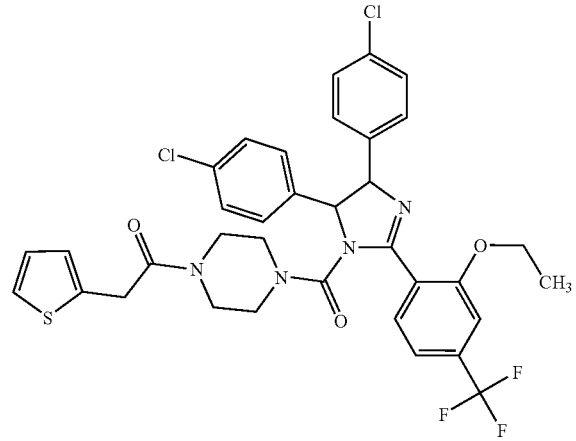

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-thiophen-2-yl-ethanone was prepared in an analogous manner as described in example 6. LR-MS: 715.4 [(M+H)+].

EXAMPLE 105

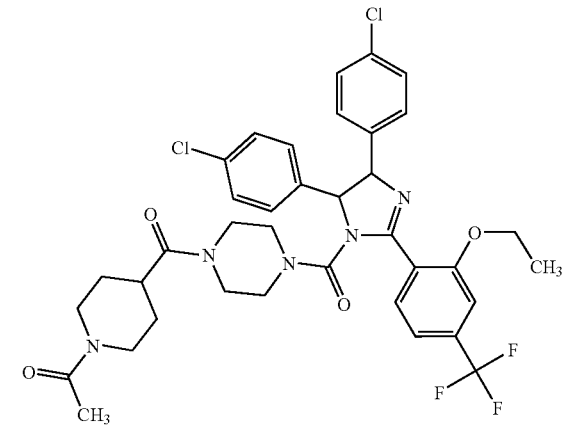

1-(4-{4-[4,5-Bis-(4-chloro-phenyl)-2-(2-ethoxy-4-trifluoromethyl-phenyl)-4,5-dihydro-imidazole-1-carbonyl]-piperazine-1-carbonyl}-piperidin-1-yl)-ethanone was prepared in an analogous manner as described in example 6. LR-MS: 744.5 [(M+H)+].

EXAMPLE 106

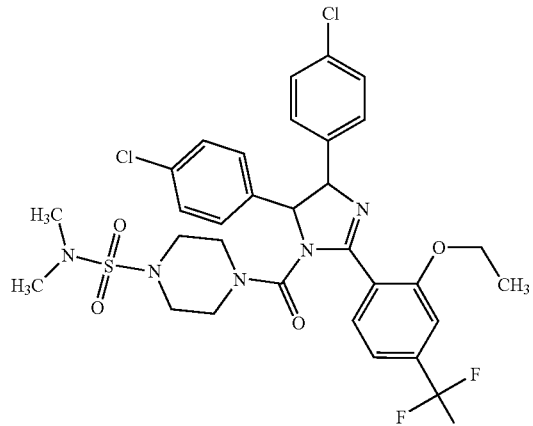

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid dimethylamide was prepared in an analogous manner as described in example 6. LR-MS: 698.4 [(M+H)+].

EXAMPLE 107

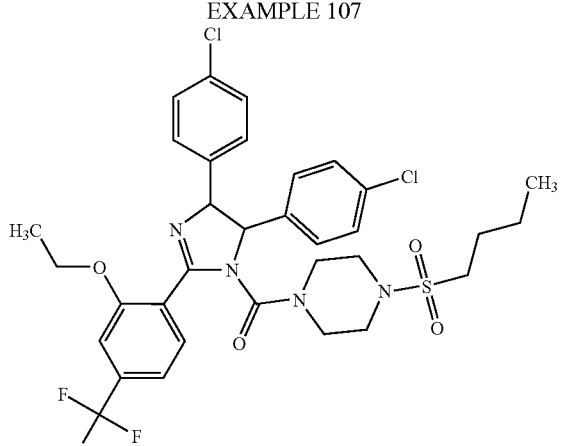

[4,5-Bis-(4-chloro-phenyl)-2-(2-ethoxy-4-trifluoromethyl-phenyl)-4,5-dihydro-imidazol-1-yl]-[4-(butane-1-sulfonyl)-piperazin-1-yl]-methanone was prepared in an analogous manner as described in example 6. LR-MS: 711.4 [(M+H)+].

EXAMPLE 108

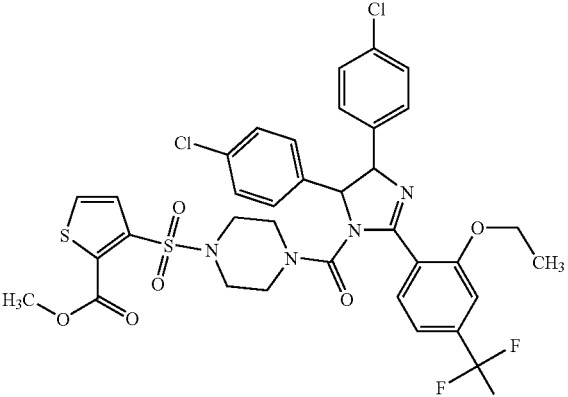

3-{4-[4,5-Bis-(4-chloro-phenyl)-2-(2-ethoxy-4-trifluoromethyl-phenyl)-4,5-dihydro-imidazole-1-carbonyl]-piperazine-1-sulfonyl}-thiophene-2-carboxylic acid methyl ester was prepared in an analogous manner as described in example 6. LR-MS: 795.4 [(M+H)+].

EXAMPLE 109

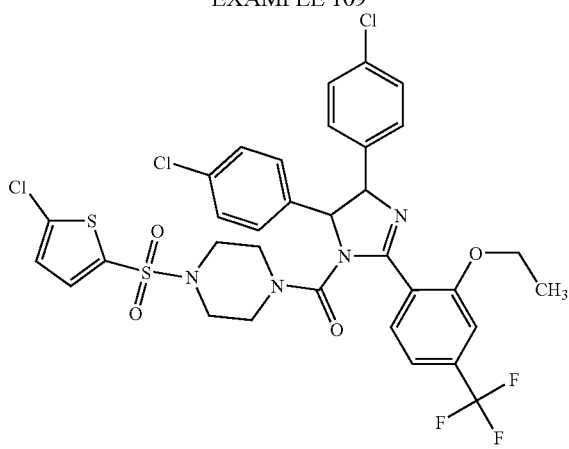

[4,5-Bis-(4-chloro-phenyl)-2-(2-ethoxy-4-trifluoromethyl-phenyl)-4,5-dihydro-imidazol-1-yl]-[4-(5-chloro-thiophene-2-sulfonyl)-piperazin-1-yl]-methanone was prepared in an analogous manner as described in example 6. LR-MS: 771.3 [(M+H)$^+$].

EXAMPLE 110

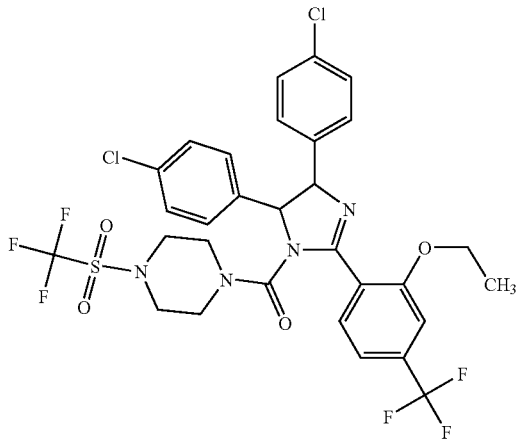

[4,5-Bis-(4-chloro-phenyl)-2-(2-ethoxy-4-trifluoromethyl-phenyl)-4,5-dihydro-imidazol-1-yl]-(4-trifluoromethanesulfonyl-piperazin-1-yl)-methanone was prepared in an analogous manner as described in example 6. LR-MS: 723.4 [(M+H)$^+$].

EXAMPLE 111

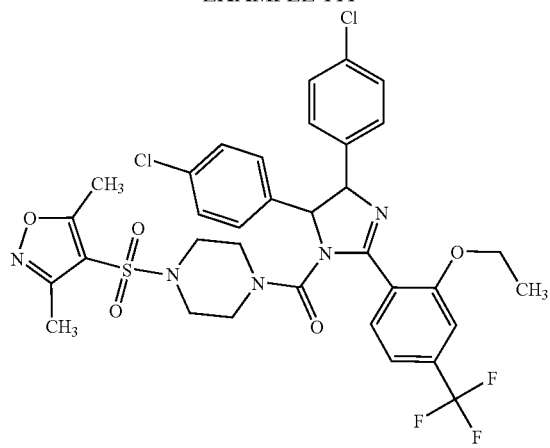

[4,5-Bis-(4-chloro-phenyl)-2-(2-ethoxy-4-trifluoromethyl-phenyl)-4,5-dihydro-imidazol-1-yl]-[4-(3,5-dimethyl-isoxazole-4-sulfonyl)-piperazin-1-yl]-methanone was prepared in an analogous manner as described in example 6. LR-MS: 750.4 [(M+H)$^+$].

EXAMPLE 112

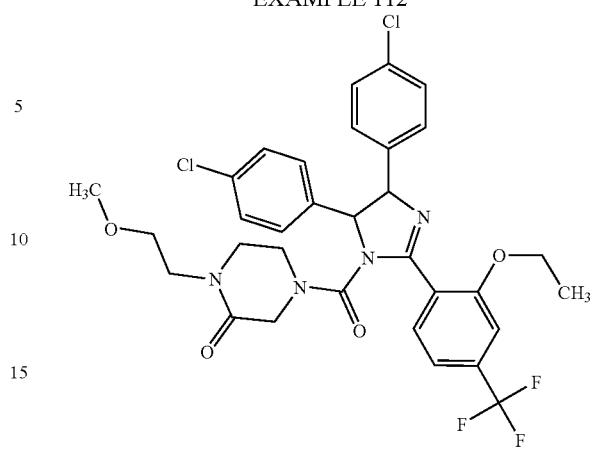

4-[4,5-Bis-(4-chloro-phenyl)-2-(2-ethoxy-4-trifluoromethyl-phenyl)-4,5-dihydro-imidazole-1-carbonyl]-1-(2-methoxy-ethyl)-piperazin-2-one was prepared in an analogous manner as described in example 7A LR-MS: 663.2 [(M+H)$^+$].

EXAMPLE 113

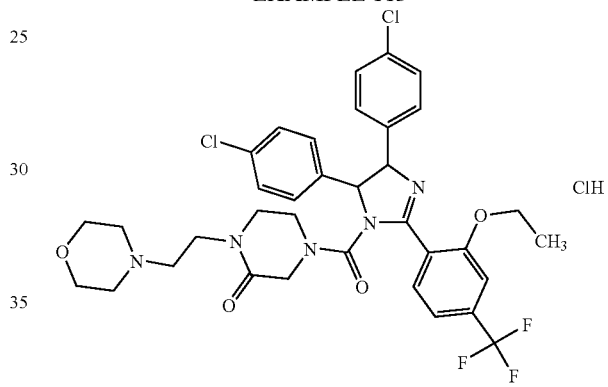

4-[4,5-Bis-(4-chloro-phenyl)-2-(2-ethoxy-4-trifluoromethyl-phenyl)-4,5-dihydro-imidazole-1-carbonyl]-1-(2-morpholin-4-yl-ethyl)-piperazin-2-one hydrochloride was prepared in an analogous manner as described in example 7B. LR-MS: 718.4 [(M+H)$^+$].

EXAMPLE 114

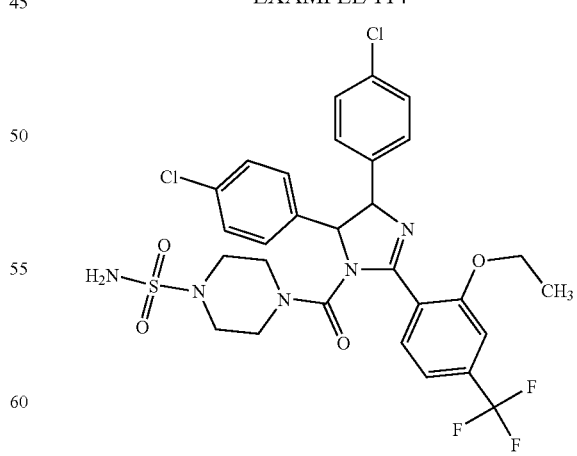

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid amide was prepared in an analogous manner as described in example 7B. LR-MS: 670.3 [(M+H)$^+$].

EXAMPLE 115

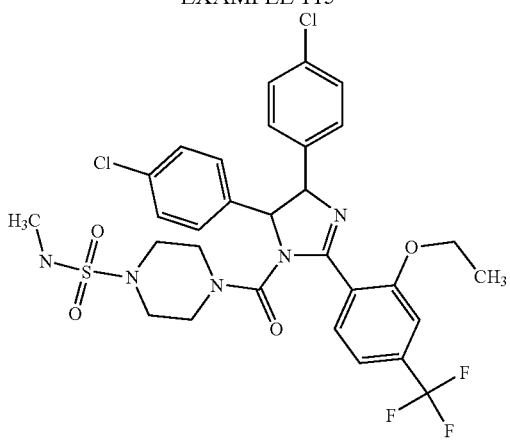

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid methylamide was prepared in an analogous manner as described in example 7B. LR-MS: 684.2 [(M+H)$^+$].

EXAMPLE 116

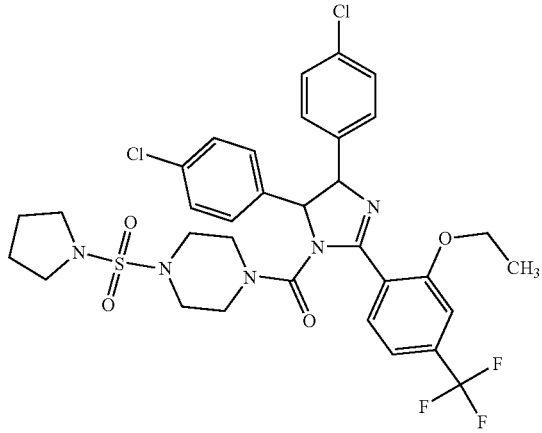

[4,5-Bis-(4-chloro-phenyl)-2-(2-ethoxy-4-trifluoromethyl-phenyl)-4,5-dihydro-imidazol-1-yl]-[4-(pyrrolidine-1-sulfonyl)-piperazin-1-yl]-methanone was prepared in an analogous manner as described in example 7B. LR-MS: 724.3 [(M+H)$^+$].

EXAMPLE 117

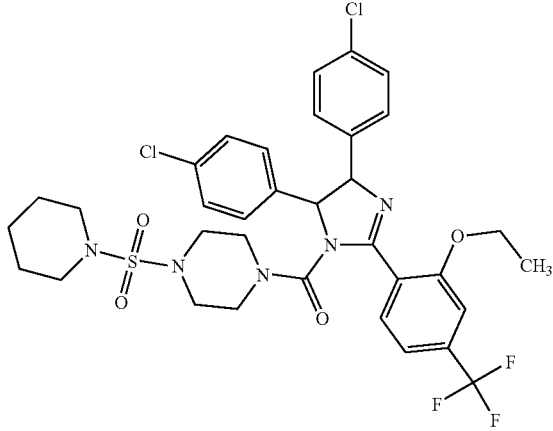

[4,5-Bis-(4-chloro-phenyl)-2-(2-ethoxy-4-trifluoromethyl-phenyl)-4,5-dihydro-imidazol-1-yl]-[4-(piperidine-1-sulfonyl)-piperazin-1-yl]-methanone was prepared in an analogous manner as described in example 7B. LR-MS: 738.3 [(M+H)$^+$].

EXAMPLE 118

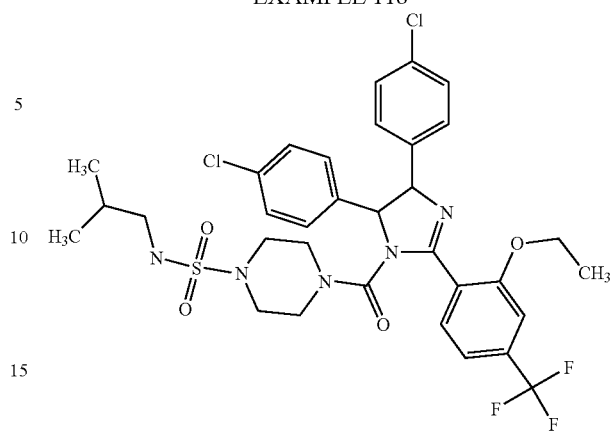

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid isobutyl-amide was prepared in an analogous manner as described in example 7B. LR-MS: 726.3 [(M+H)$^+$].

EXAMPLE 119

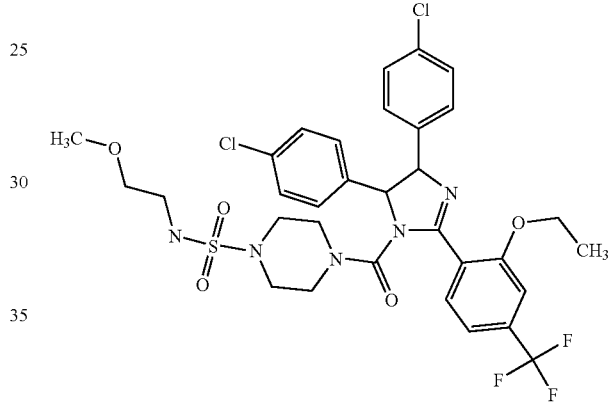

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid (2-methoxy-ethyl)-amide was prepared in an analogous manner as described in example 7B. LR-MS: 728.2 [(M+H)$^+$].

EXAMPLE 120

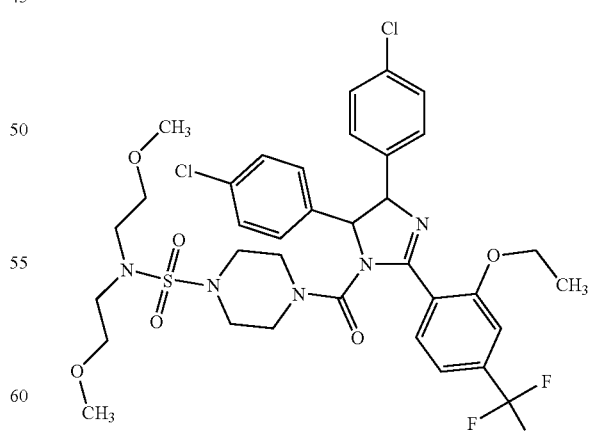

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid bis-(2-methoxy-ethyl)-amide was prepared in an analogous manner as described in example 7B. LR-MS: 786.3 [(M+H)$^+$].

EXAMPLE 121

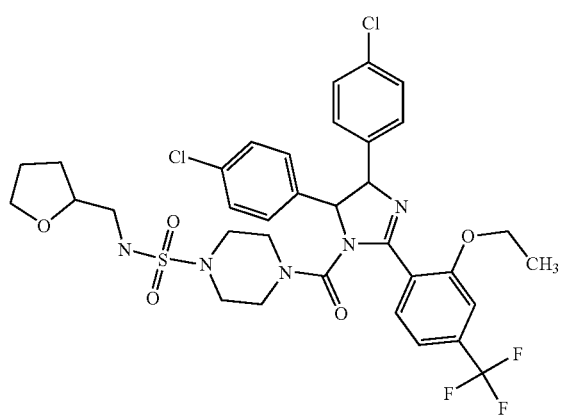

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid (tetrahydro-furan-2-ylmethyl)-amide was prepared in an analogous manner as described in example 7B. LR-MS: 754.3 [(M+H)$^+$].

EXAMPLE 122

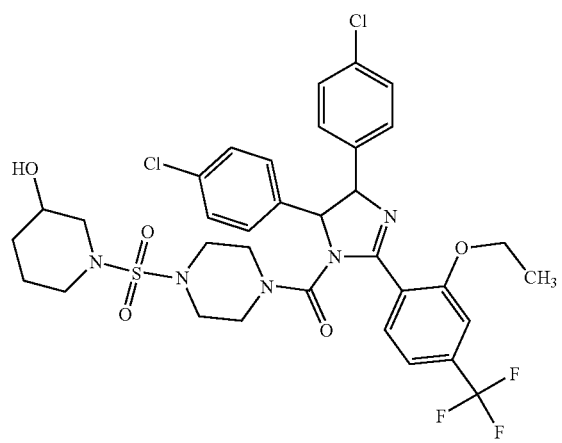

[4,5-Bis-(4-chloro-phenyl)-2-(2-ethoxy-4-trifluoromethyl-phenyl)-4,5-dihydro-imidazol-1-yl]-[4-(3-hydroxy-piperidine-1-sulfonyl)-piperazin-1-yl]-methanone was prepared in an analogous manner as described in example 7B. LR-MS: 754.3 [(M+H)$^+$].

EXAMPLE 123

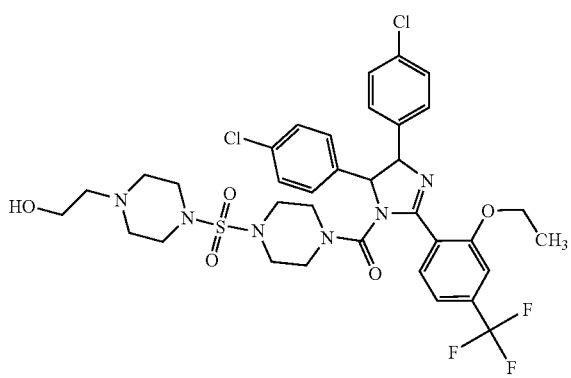

[4,5-Bis-(4-chloro-phenyl)-2-(2-ethoxy-4-trifluoromethyl-phenyl)-4,5-dihydro-imidazol-1-yl]-{4-[4-(2-hydroxy-ethyl)-piperazine-1-sulfonyl]-piperazin-1-yl}-methanone was prepared in an analogous manner as described in example 7B. LR-MS: 783.3 [(M+H)$^+$].

EXAMPLE 124

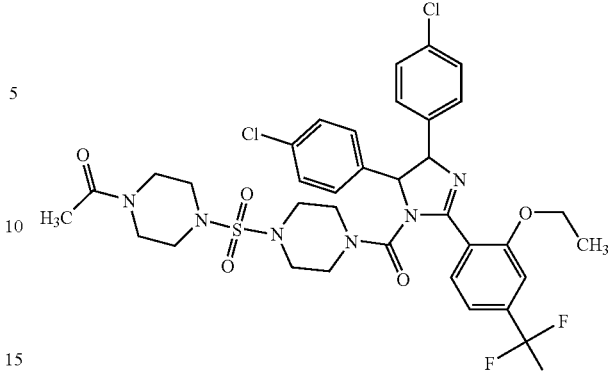

1-(4-{4-[4,5-Bis-(4-chloro-phenyl)-2-(2-ethoxy-4-trifluoromethyl-phenyl)-4,5-dihydro-imidazole-1-carbonyl]-piperazine-1-sulfonyl}-piperazin-1-yl)-ethanone was prepared in an analogous manner as described in example 7B. LR-MS: 781.3 [(M+H)$^+$].

EXAMPLE 125

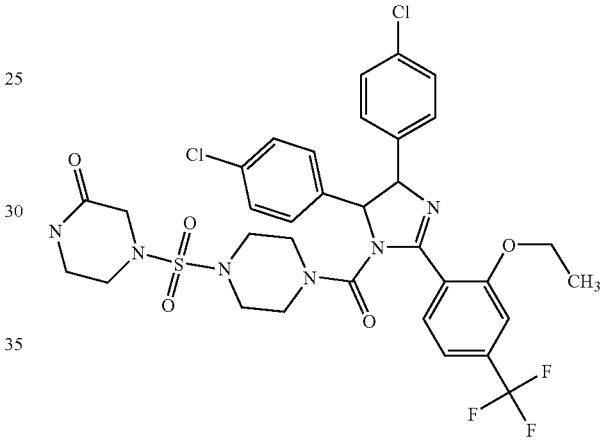

4-{4-[4,5-Bis-(4-chloro-phenyl)-2-(2-ethoxy-4-trifluoromethyl-phenyl)-4,5-dihydro-imidazole-1-carbonyl]-piperazine-1-sulfonyl}-piperazin-2-one was prepared in an analogous manner as described in example 7B. LR-MS: 753.2 [(M+H)$^+$].

EXAMPLE 126

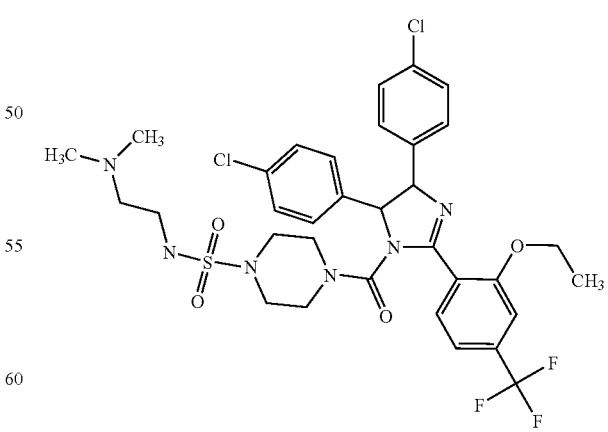

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid (2-dimethylamino-ethyl)-amide was prepared in an analogous manner as described in example 7B. LR-MS: 741.2 [(M+H)$^+$].

EXAMPLE 127

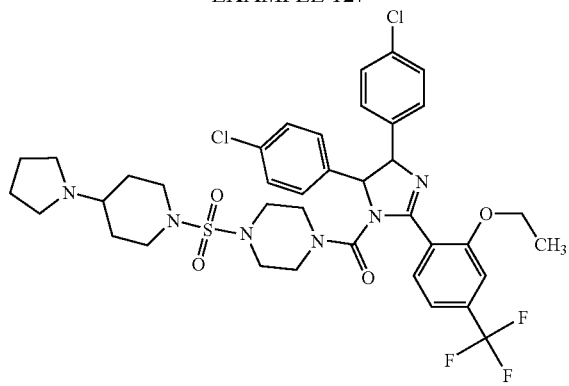

[4,5-Bis-(4-chloro-phenyl)-2-(2-ethoxy-4-trifluorom-ethyl-phenyl)-4,5-dihydro-imidazol-1-yl]-[4-(4-pyrrolidin-1-yl-piperidine-1-sulfonyl)-piperazin-1-yl]-methanone was prepared in an analogous manner as described in example 7B. LR-MS: 807.3 [(M+H)$^+$].

EXAMPLE 128

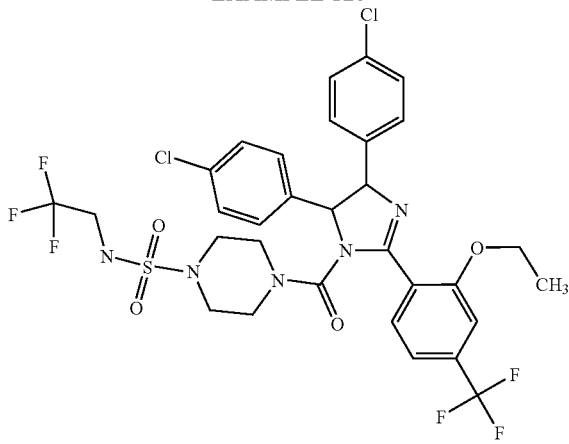

4-[4,5-Bis-(4-chloro-phenyl)-2-(2-ethoxy-4-trifluorom-ethyl-phenyl)-4,5-dihydro-imidazole-1-carbonyl]-piperazine-1-sulfonic acid (2,2,2-trifluoro-ethyl)-amide was prepared in an analogous manner as described in example 7B. LR-MS: 752.2 [(M+H)$^+$].

EXAMPLE 129

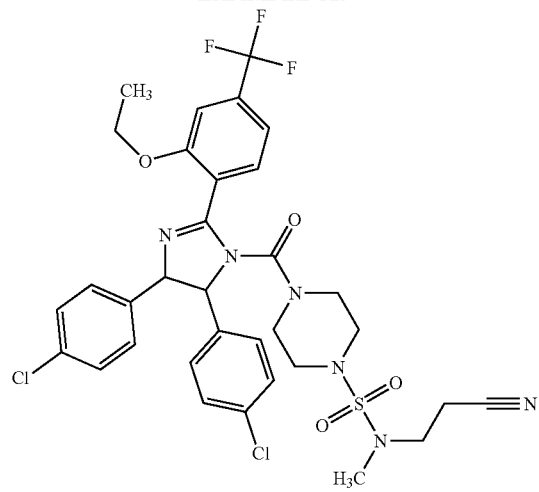

4-[4,5-Bis-(4-chloro-phenyl)-2-(2-ethoxy-4-trifluorom-ethyl-phenyl)-4,5-dihydro-imidazole-1-carbonyl]-piperazine-1-sulfonic acid (2-cyano-ethyl)-methyl-amide was prepared in an analogous manner as described in example 7B. LR-MS: 737.3 [(M+H)$^+$].

EXAMPLE 130

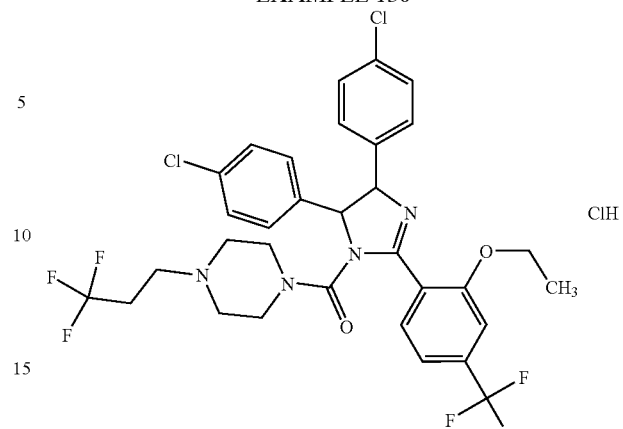

[4,5-Bis-(4-chloro-phenyl)-2-(2-ethoxy-4-trifluorom-ethyl-phenyl)-4,5-dihydro-imidazol-1-yl]-[4-(3,3,3-trifluoro-propyl)-piperazin-1-yl]-methanone hydrochloride was prepared in an analogous manner as described in example 8A. LR-MS: 687.5 [(M+H)$^+$].

EXAMPLE 131

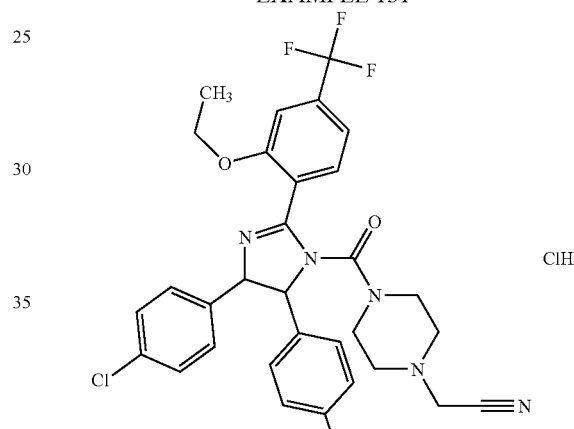

{4-[4,5-Bis-(4-chloro-phenyl)-2-(2-ethoxy-4-trifluorom-ethyl-phenyl)-4,5-dihydro-imidazole-1-carbonyl]-piperazin-1-yl}-acetonitrile hydrochloride was prepared in an analogous manner as described in example 8A. LR-MS: 630.2 [(M+H)$^+$].

EXAMPLE 132

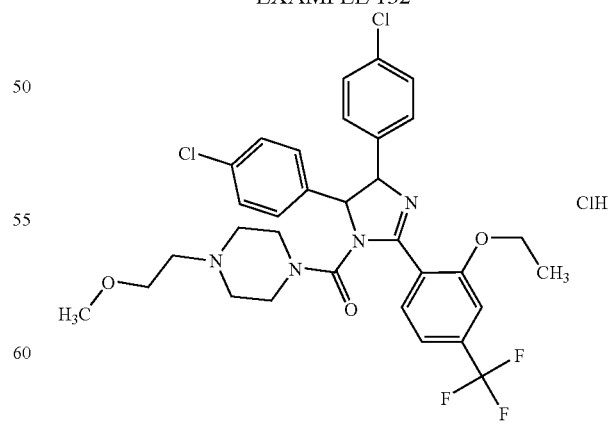

[4,5-Bis-(4-chloro-phenyl)-2-(2-ethoxy-4-trifluorom-ethyl-phenyl)-4,5-dihydro-imidazol-1-yl]-[4-(2-methoxy-ethyl)-piperazin-1-yl]-methanone hydrochloride was prepared in an analogous manner as described in example 8A. LR-MS: 649.5 [(M+H)$^+$].

EXAMPLE 133

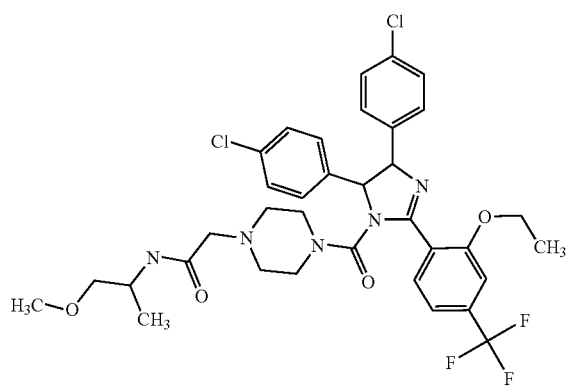

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(2-methoxy-1-methyl-ethyl)-acetamide was prepared in an analogous manner as described in example 8B. LR-MS: 720.5 [(M+H)$^+$].

EXAMPLE 134

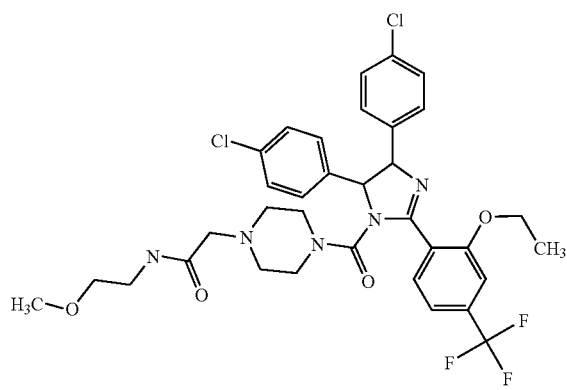

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(2-methoxy-ethyl)-acetamide was prepared in an analogous manner as described in example 8B. LR-MS: 706.4 [(M+H)$^+$].

EXAMPLE 135

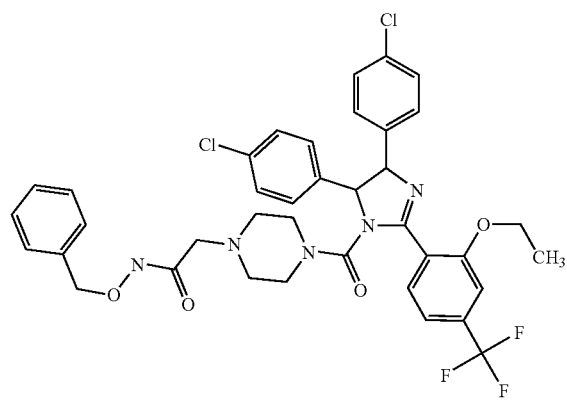

N-Benzyloxy-2-{4-[4,5-bis-(4-chloro-phenyl)-2-(2-ethoxy-4-trifluoromethyl-phenyl)-4,5-dihydro-imidazole-1-carbonyl]-piperazin-1-yl}-acetamide was prepared in an analogous manner as described in example 8B. LR-MS: 754.5 [(M+H)$^+$].

EXAMPLE 136

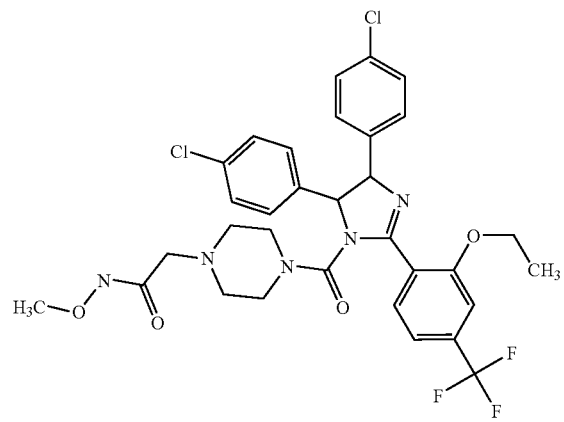

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-methoxy-acetamide was prepared in an analogous manner as described in example 8B. LR-MS: 678.4 [(M+H)$^+$].

EXAMPLE 137

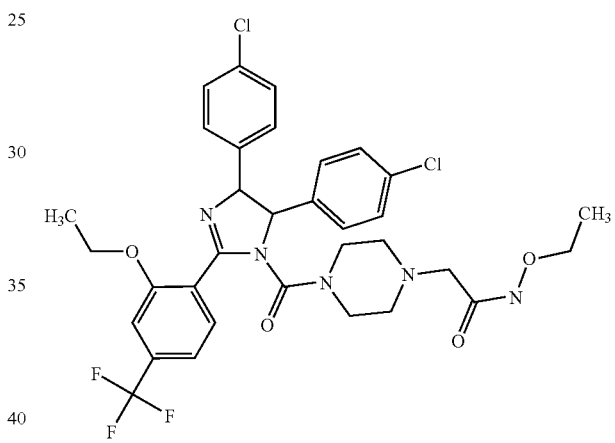

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-ethoxy-acetamide was prepared in an analogous manner as described in example 8B. LR-MS: 692.4 [(M+H)$^+$].

EXAMPLE 138

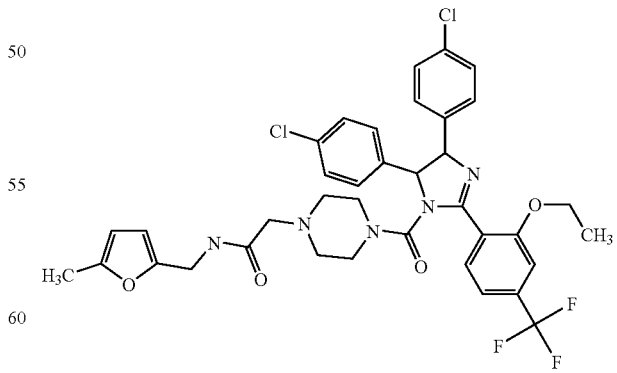

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(5-methyl-furan-2-ylmethyl)-acetamide was prepared in an analogous manner as described in example 8B. LR-MS: 742.5 [(M+H)$^+$].

EXAMPLE 139

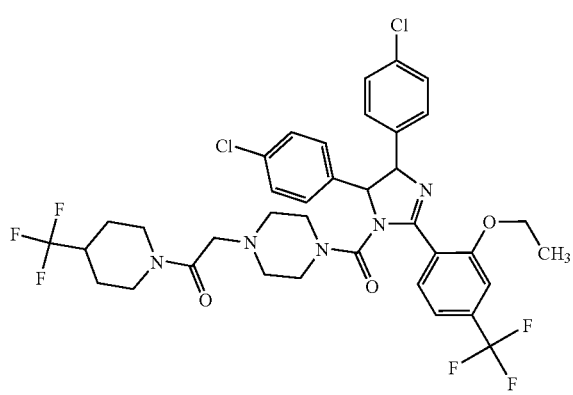

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-(4-trifluoromethyl-piperidin-1-yl)-ethanone was prepared in an analogous manner as described in example 8B. LR-MS: 784.5 [(M+H)$^+$].

EXAMPLE 140

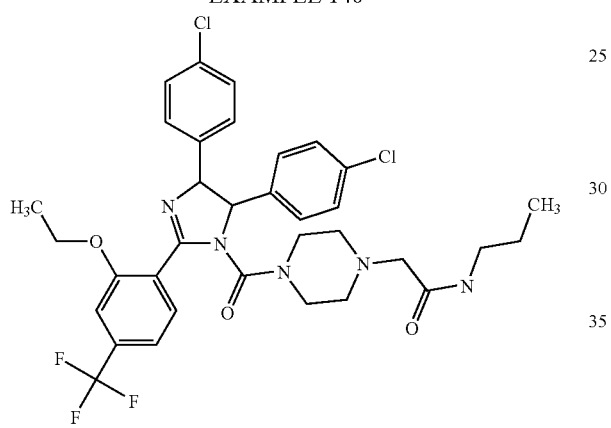

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-propyl-acetamide was prepared in an analogous manner as described in example 8B. LR-MS: 690.5 [(M+H)$^+$].

EXAMPLE 141

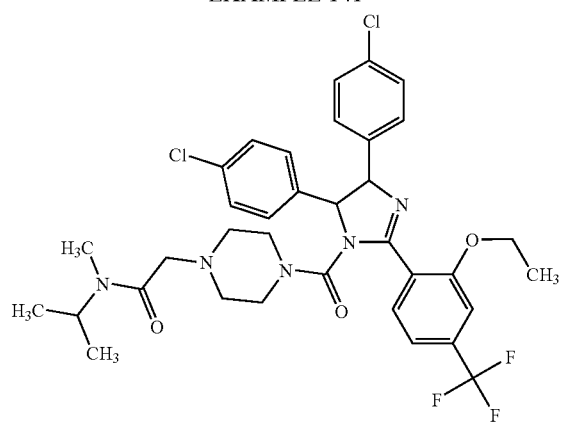

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-isopropyl-N-methyl-acetamide was prepared in an analogous manner as described in example 8B. LR-MS: 704.5 [(M+H)$^+$].

EXAMPLE 142

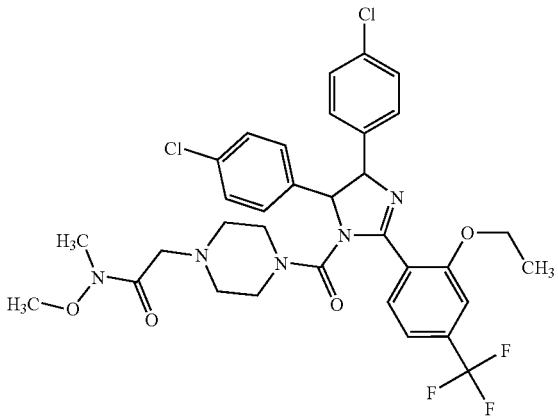

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-methoxy-N-methyl-acetamide was prepared in an analogous manner as described in example 8B. LR-MS: 692.5 [(M+H)$^+$].

EXAMPLE 143

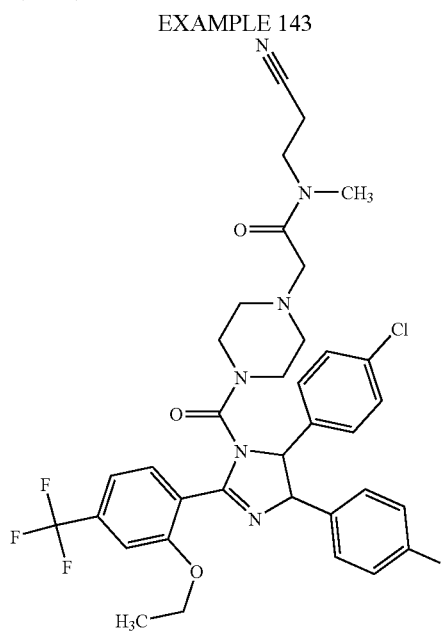

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(2-cyano-ethyl)-N-methyl-acetamide was prepared in an analogous manner as described in example 8B. LR-MS: 715.5 [(M+H)$^+$].

EXAMPLE 144

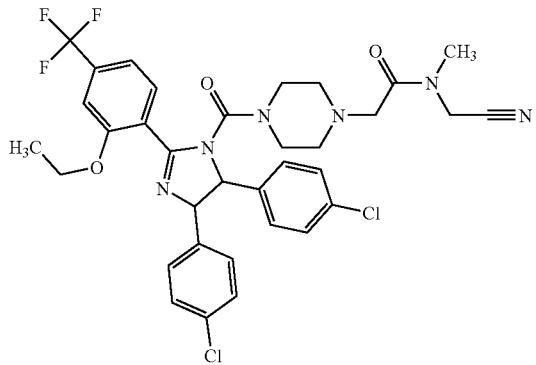

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-cyanomethyl-N-methyl-acetamide was prepared in an analogous manner as described in example 8B. LR-MS: 701.5 [(M+H)⁺].

EXAMPLE 145

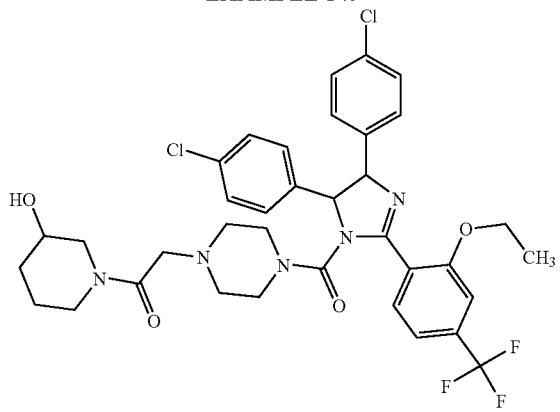

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-(3-hydroxy-piperidin-1-yl)-ethanone was prepared in an analogous manner as described in example 8B. LR-MS: 732.5 [(M+H)⁺].

EXAMPLE 146

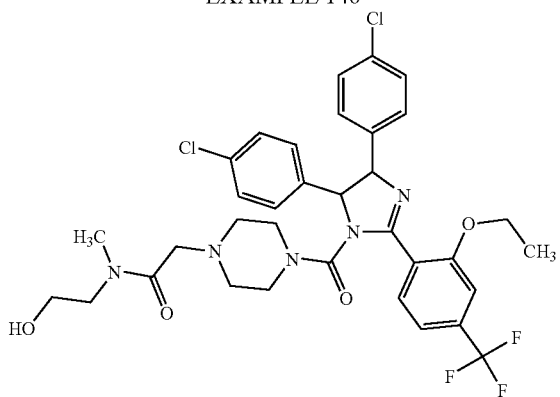

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(2-hydroxy-ethyl)-N-methyl-acetamide was prepared in an analogous manner as described in example 8B. LR-MS: 706.5 [(M+H)⁺].

EXAMPLE 147

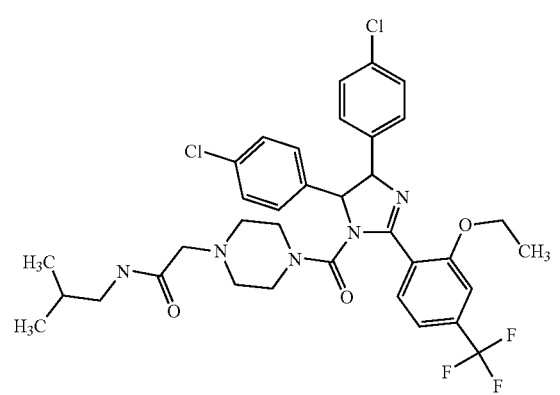

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-isobutyl-acetamide was prepared in an analogous manner as described in example 8B. LR-MS: 704.5 [(M+H)⁺].

EXAMPLE 148

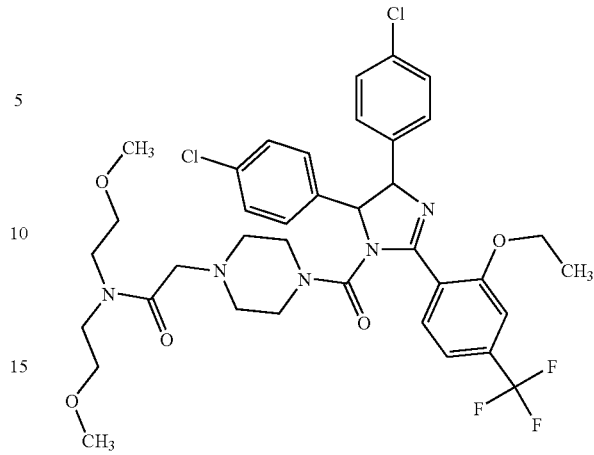

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N,N-bis-(2-methoxy-ethyl)-acetamide was prepared in an analogous manner as described in example 8B. LR-MS: 764.5 [(M+H)⁺].

EXAMPLE 149

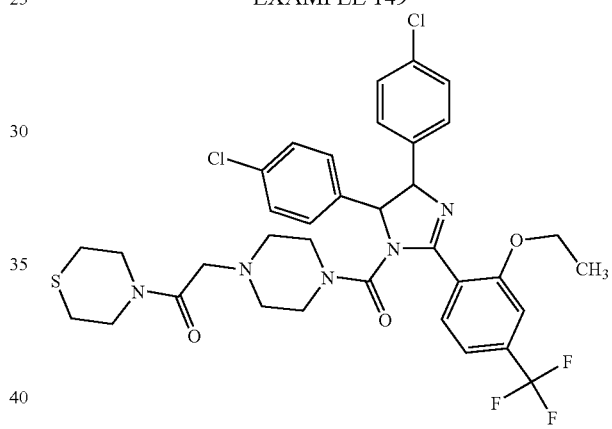

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-thiomorpholin-4-yl-ethanone was prepared in an analogous manner as described in example 8B. LR-MS: 734.5 [(M+H)⁺].

EXAMPLE 150

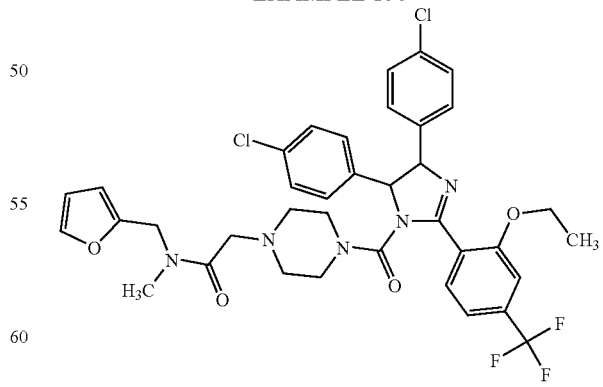

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-furan-2-ylmethyl-N-methyl-acetamide was prepared in an analogous manner as described in example 8B. LR-MS: 742.5 [(M+H)⁺].

EXAMPLE 151

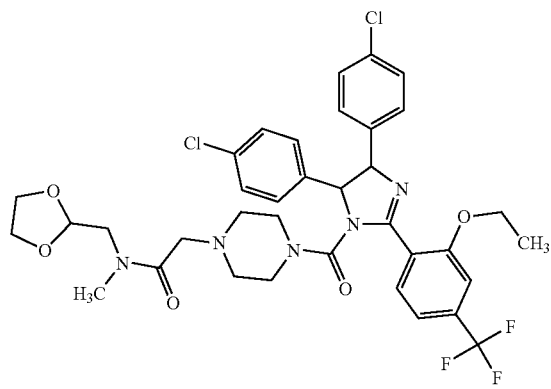

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-[1,3]dioxolan-2-ylmethyl-N-methyl-acetamide was prepared in an analogous manner as described in example 8B. LR-MS: 748.4 [(M+H)$^+$].

EXAMPLE 152

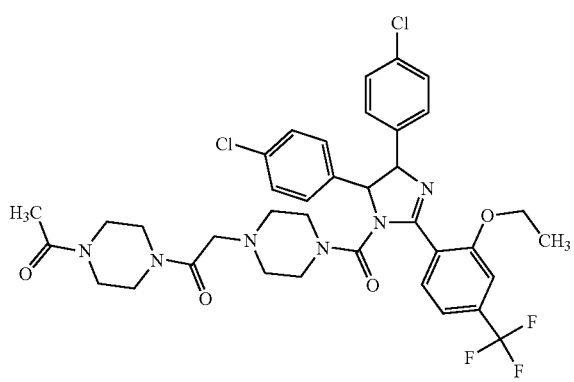

1-(4-Acetyl-piperazin-1-yl)-2-{4-[4,5-bis-(4-chloro-phenyl)-2-(2-ethoxy-4-trifluoromethyl-phenyl)-4,5-dihydro-imidazole-1-carbonyl]-piperazin-1-yl}-ethanone was prepared in an analogous manner as described in example 8B. LR-MS: 759.5 [(M+H)$^+$].

EXAMPLE 153

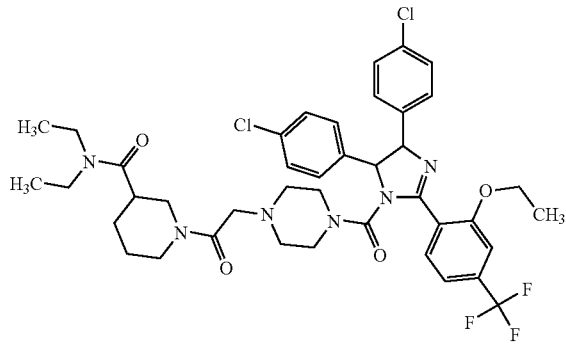

1-({4-[4,5-Bis-(4-chloro-phenyl)-2-(2-ethoxy-4-trifluoromethyl-phenyl)-4,5-dihydro-imidazole-1-carbonyl]-piperazin-1-yl}-acetyl)-piperidine-3-carboxylic acid diethylamide was prepared in an analogous manner as described in example 8B. LR-MS: 815.6 [(M+H)$^+$].

EXAMPLE 154

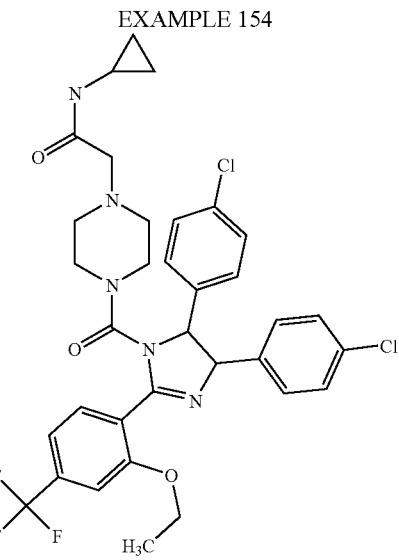

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-cyclopropyl-acetamide was prepared in an analogous manner as described in example 8B. LR-MS: 688.4 [(M+H)$^+$].

EXAMPLE 155

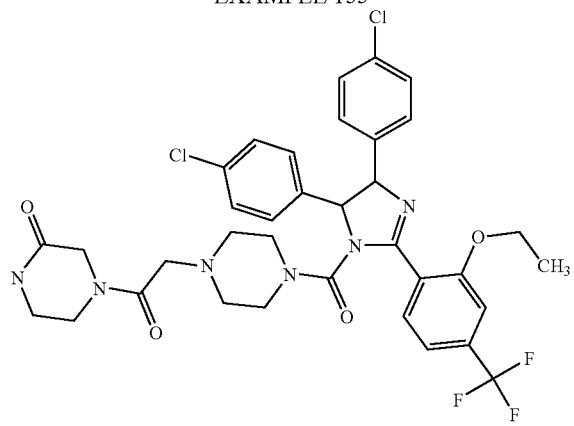

4-({4-[4,5-Bis-(4-chloro-phenyl)-2-(2-ethoxy-4-trifluoromethyl-phenyl)-4,5-dihydro-imidazole-1-carbonyl]-piperazin-1-yl}-acetyl)-piperazin-2-one was prepared in an analogous manner as described in example 8B. LR-MS: 731.5 [(M+H)$^+$].

EXAMPLE 156

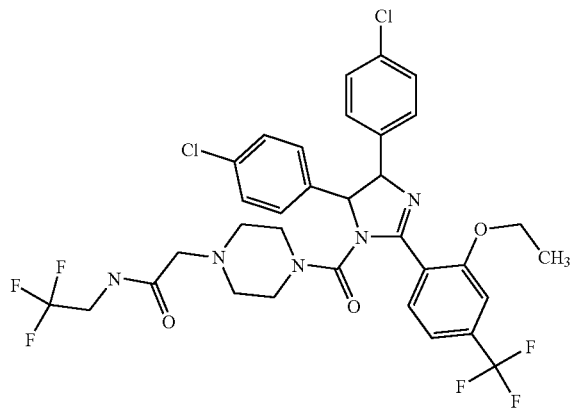

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(2,2,2-trifluoro-ethyl)-acetamide was prepared in an analogous manner as described in example 8B. LR-MS: 730.5 [(M+H)⁺].

EXAMPLE 157

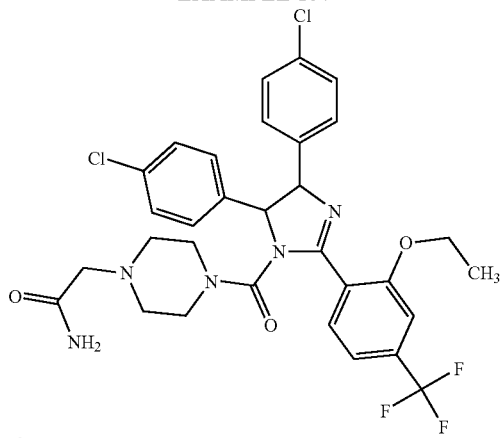

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-acetamide was prepared in an analogous manner as described in example 8B. LR-MS: 648.4 [(M+H)⁺].

EXAMPLE 158

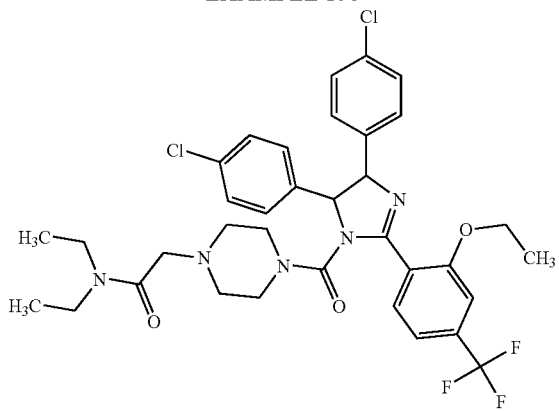

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N,N-diethyl-acetamide was prepared in an analogous manner as described in example 8B. LR-MS: 704.5 [(M+H)⁺].

EXAMPLE 159

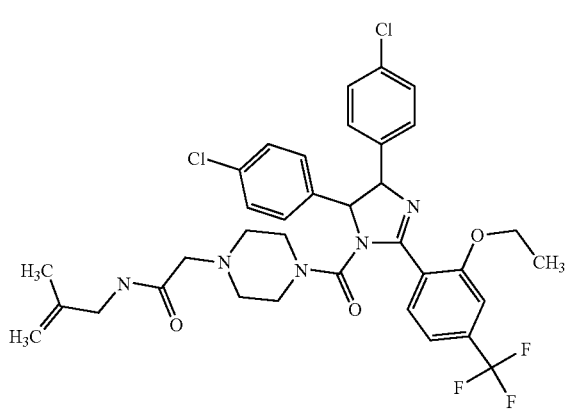

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(2-methyl-allyl)-acetamide was prepared in an analogous manner as described in example 8B. LR-MS: 702.5 [(M+H)⁺].

EXAMPLE 160

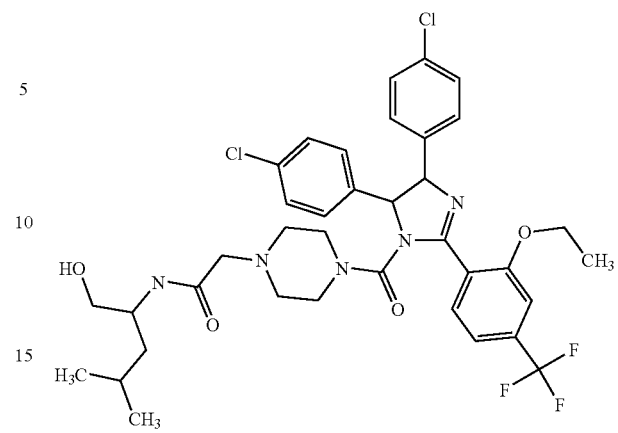

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(1-hydroxymethyl-3-methyl-butyl)-acetamide was prepared in an analogous manner as described in example 8B. LR-MS: 748.5 [(M+H)⁺].

EXAMPLE 161

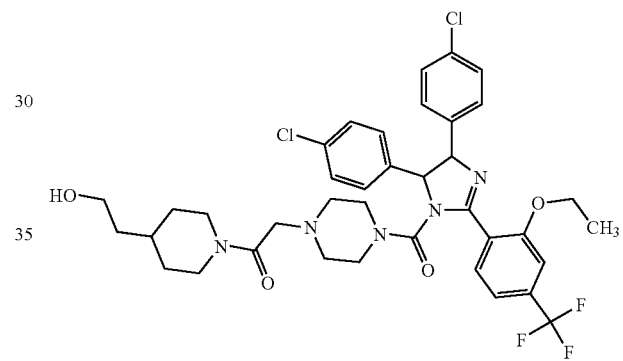

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-[4-(2-hydroxy-ethyl)-piperidin-1-yl]-ethanone was prepared in an analogous manner as described in example 8B. LR-MS: 760.50 [(M+H)⁺].

EXAMPLE 162

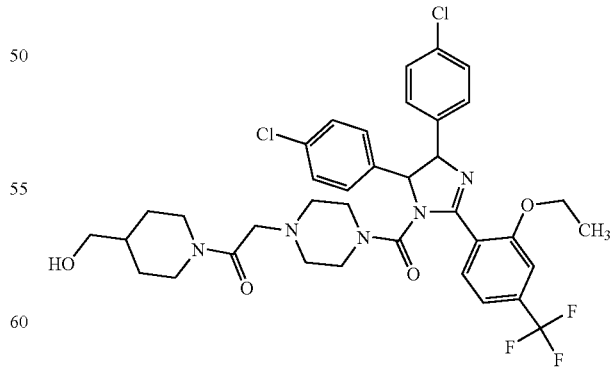

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-(4-hydroxymethyl-piperidin-1-yl)-ethanone was prepared in an analogous manner as described in example 8B. LR-MS: 746.50 [(M+H)⁺].

EXAMPLE 163

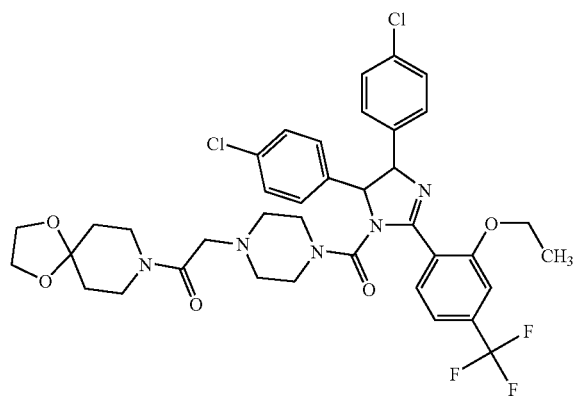

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-(1,4-dioxa-8-aza-spiro[4.5]dec-8-yl)-ethanone was prepared in an analogous manner as described in example 8B. LR-MS: 774.50 [(M+H)+].

EXAMPLE 164

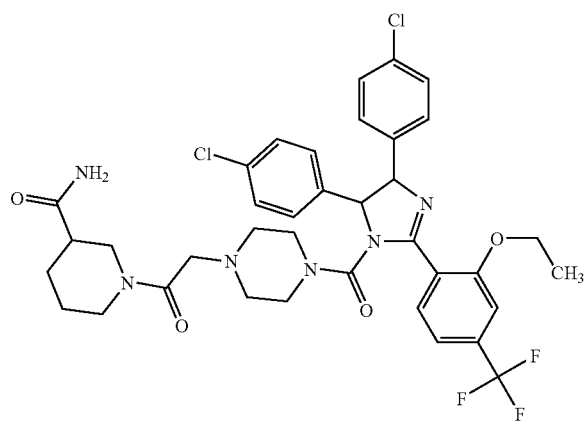

1-({4-[4,5-Bis-(4-chloro-phenyl)-2-(2-ethoxy-4-trifluoromethyl-phenyl)-4,5-dihydro-imidazole-1-carbonyl]-piperazin-1-yl}-acetyl)-piperidine-3-carboxylic acid amide was prepared in an analogous manner as described in example 8B. LR-MS: 760 [(M+H)+].

EXAMPLE 165

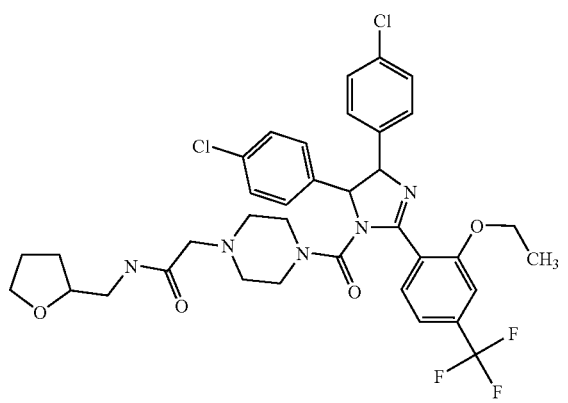

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(tetrahydro-furan-2-ylmethyl)-acetamide was prepared in an analogous manner as described in example 8B. LR-MS: 732.5 [(M+H)+].

EXAMPLE 166

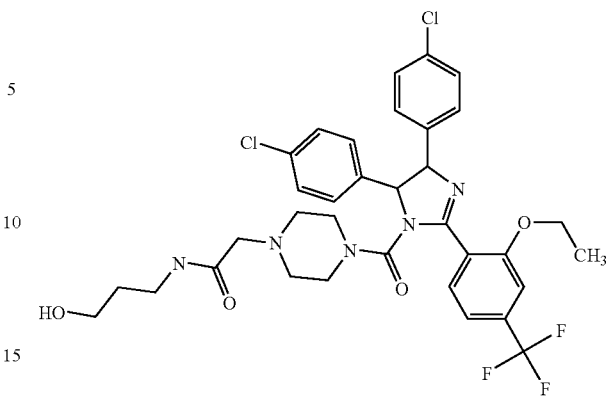

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(3-hydroxy-propyl)-acetamide was prepared in an analogous manner as described in example 8B. LR-MS: 706.30 [(M+H)+].

EXAMPLE 167

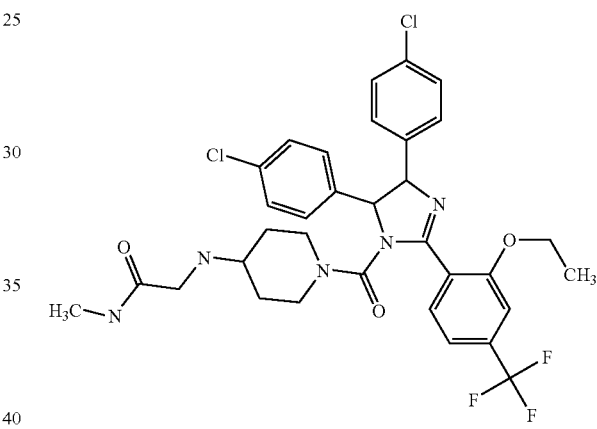

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-methyl-acetamide was prepared in an analogous manner as described in example 8B. LR-MS: 676.5 [(M+H)+].

EXAMPLE 168

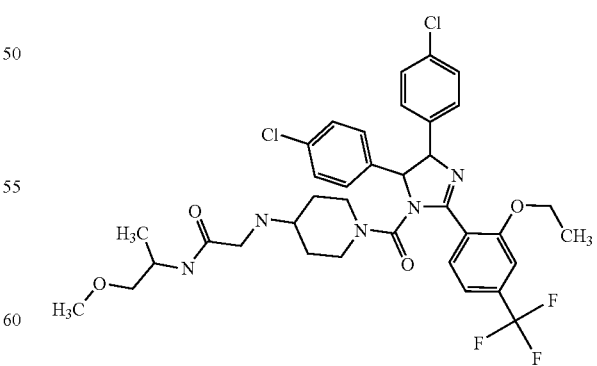

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(2-methoxy-1-methyl-ethyl)-acetamide was prepared in an analogous manner as described in example 8B. LR-MS: 734.5 [(M+H)+].

EXAMPLE 169

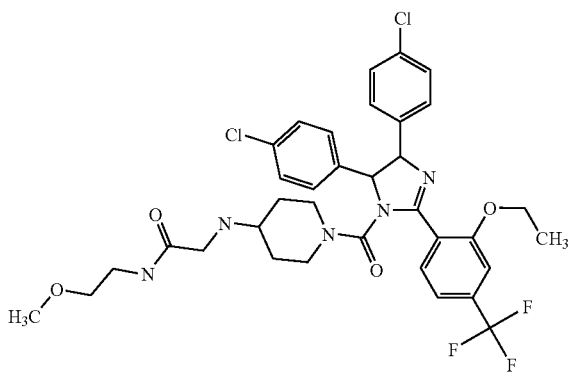

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(2-methoxy-ethyl)-acetamide was prepared in an analogous manner as described in example 8B. LR-MS: 720.5 [(M+H)$^+$].

EXAMPLE 170

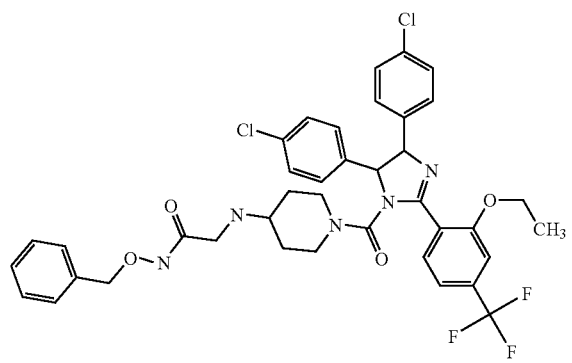

N-Benzyloxy-2-{1-[4,5-bis-(4-chloro-phenyl)-2-(2-ethoxy-4-trifluoromethyl-phenyl)-4,5-dihydro-imidazole-1-carbonyl]-piperidin-4-ylamino}-acetamide was prepared in an analogous manner as described in example 8B. LR-MS: 768.5 [(M+H)$^+$].

EXAMPLE 171

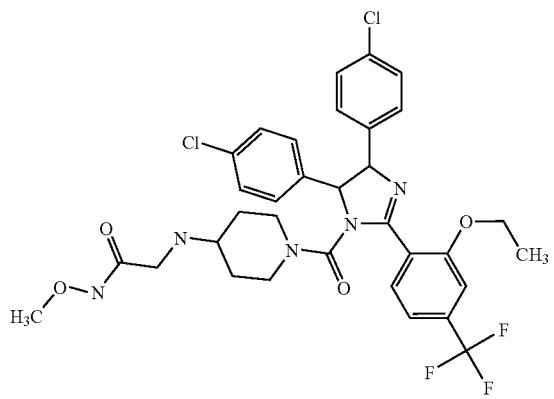

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-methoxy-acetamide was prepared in an analogous manner as described in example 8B. LR-MS: 692.4 [(M+H)$^+$].

EXAMPLE 172

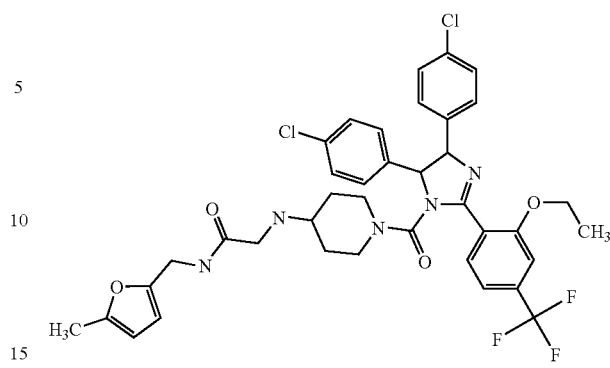

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(5-methyl-furan-2-ylmethyl)-acetamide was prepared in an analogous manner as described in example 8B. LR-MS: 756.5 [(M+H)$^+$].

EXAMPLE 173

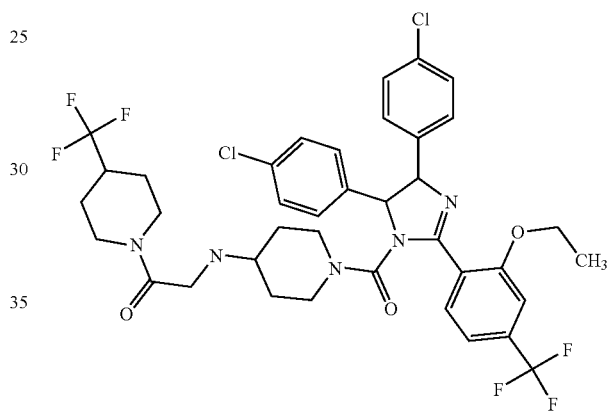

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-1-(4-trifluoromethyl-piperidin 1-yl)-ethanone was prepared in an analogous manner as described in example 8B. LR-MS: 798.5 [(M+H)$^+$].

EXAMPLE 174

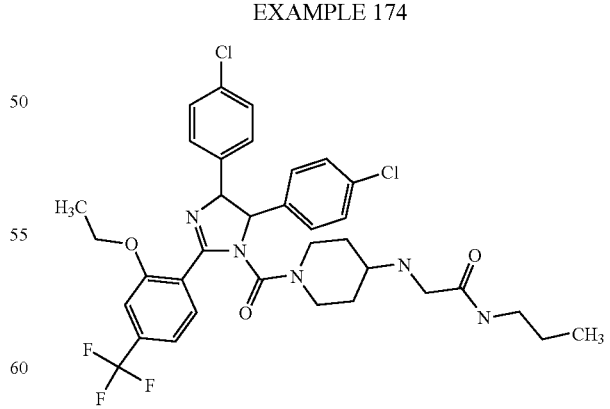

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-propyl-acetamide was prepared in an analogous manner as described in example 8B. LR-MS: 704.5 [(M+H)$^+$].

EXAMPLE 175

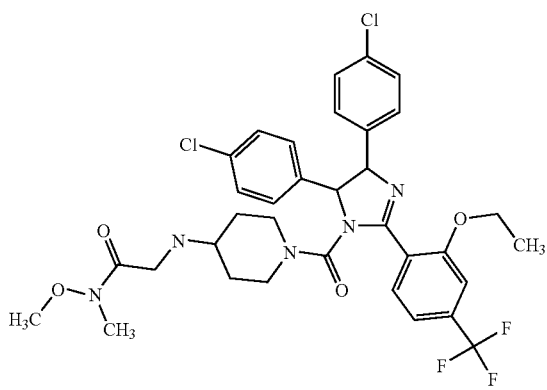

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-methoxy-N-methyl-acetamide was prepared in an analogous manner as described in example 8B. LR-MS: 706.4 [(M+H)$^+$].

EXAMPLE 176

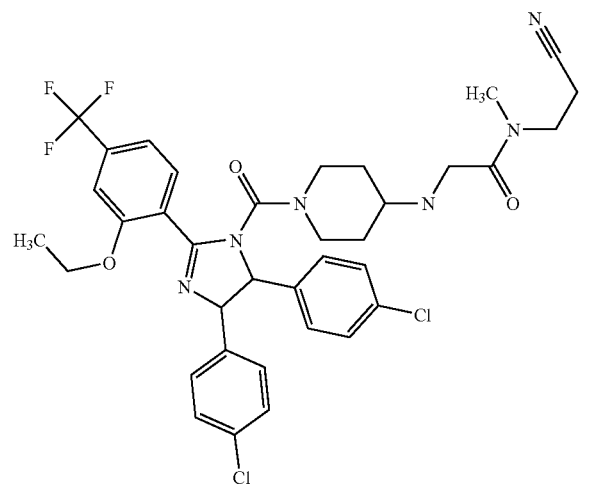

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(2-cyano-ethyl)-N-methyl-acetamide was prepared in an analogous manner as described in example 8B. LR-MS: 729.5 [(M+H)$^+$].

EXAMPLE 177

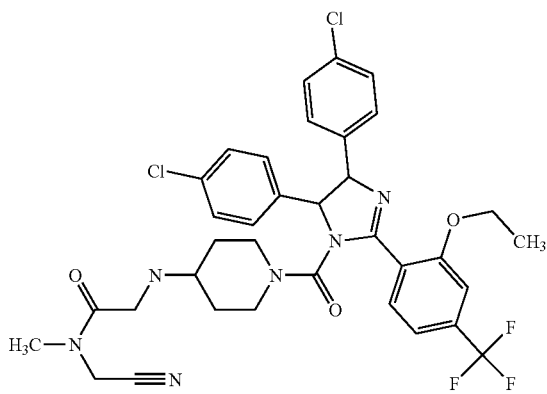

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-cyanomethyl-N-methyl-acetamide was prepared in an analogous manner as described in example 8B. LR-MS: 715.5 [(M+H)$^+$].

EXAMPLE 178

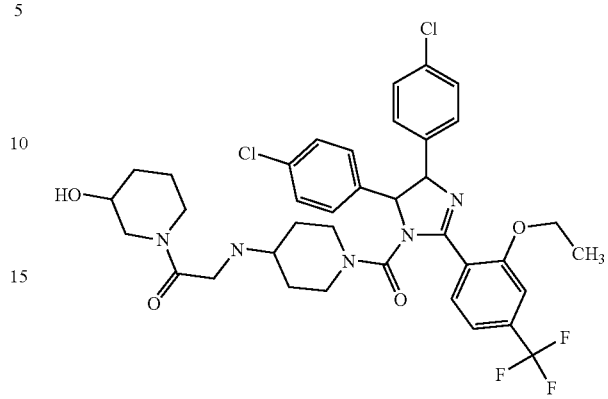

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-1-(3-hydroxy-piperidin-1-yl)-ethanone was prepared in an analogous manner as described in example 8B. LR-MS: 746.5 [(M+H)$^+$].

EXAMPLE 179

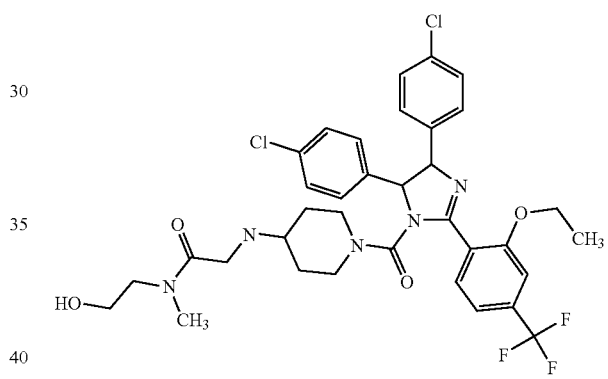

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(2-hydroxy-ethyl)-N-methyl-acetamide was prepared in an analogous manner as described in example 8B. LR-MS: 720.4 [(M+H)$^+$].

EXAMPLE 180

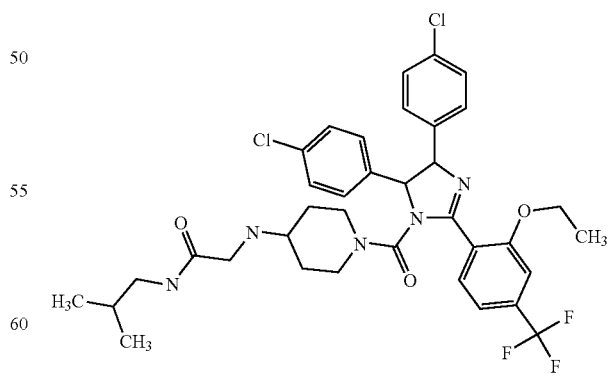

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-isobutyl-acetamide was prepared in an analogous manner as described in example 8B. LR-MS: 718.5 [(M+H)$^+$].

EXAMPLE 181

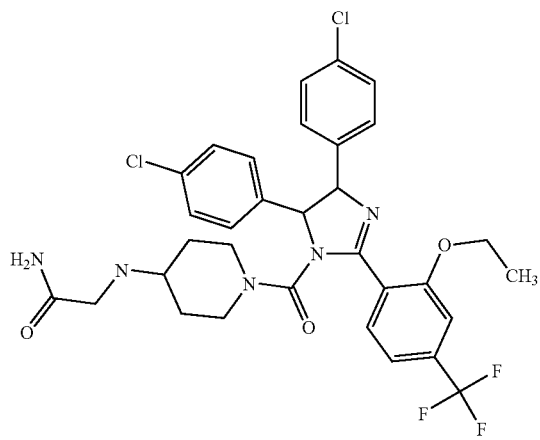

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-acetamide was prepared in an analogous manner as described in example 8B. LR-MS: 662.4 [(M+H)$^+$].

EXAMPLE 182

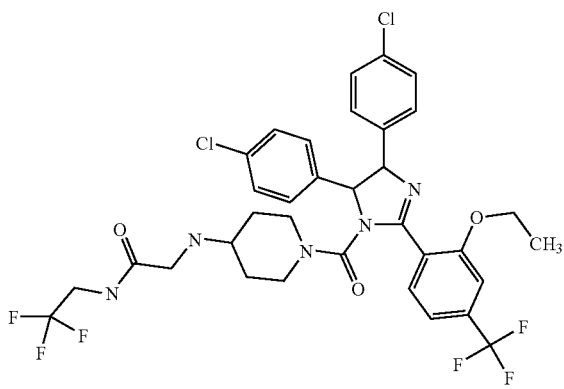

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(2,2,2-trifluoro-ethyl)-acetamide was prepared in an analogous manner as described in example 8B. LR-MS: 744.5 [(M+H)$^+$].

EXAMPLE 183

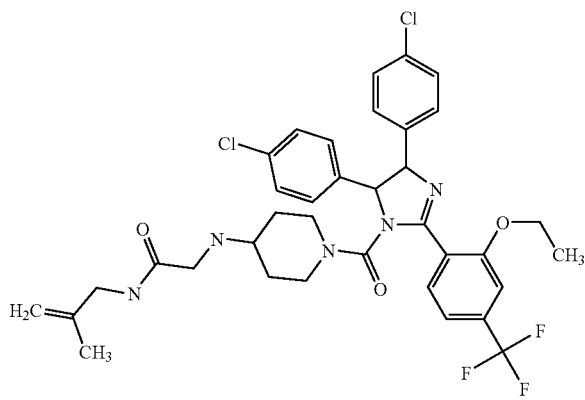

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(2-methyl-allyl)-acetamide was prepared in an analogous manner as described in example 8B. LR-MS: 716.5 [(M+H)$^+$].

EXAMPLE 184

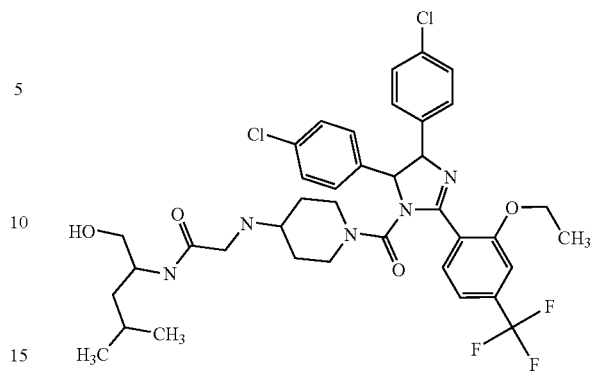

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(1-hydroxymethyl-3-methyl-butyl)-acetamide was prepared in an analogous manner as described in example 8B. LR-MS: 762.6 [(M+H)$^+$].

EXAMPLE 185

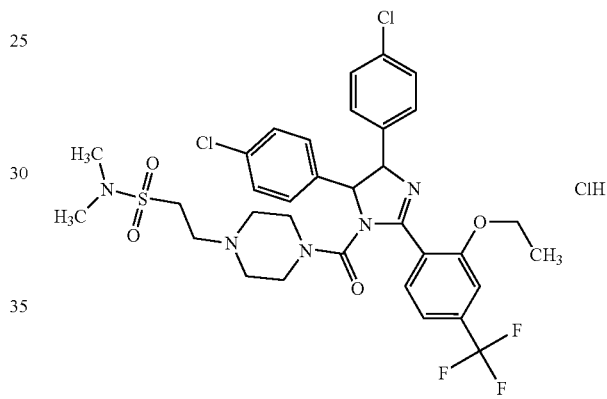

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-ethanesulfonic acid dimethylamide hydrochloride was prepared in an analogous manner as described in example 8A. LR-MS: 726.2 [(M+H)$^+$].

EXAMPLE 186

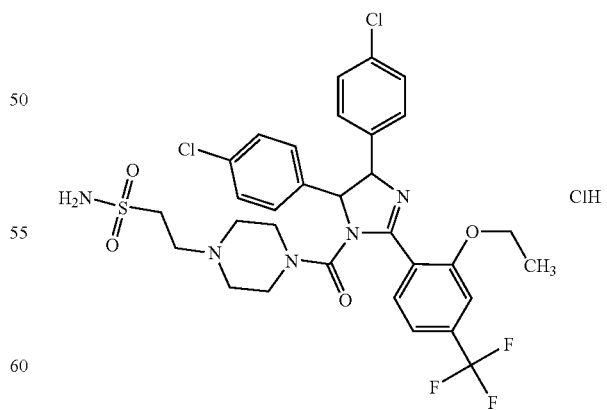

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-ethanesulfonic acid amide hydrochloride was prepared in an analogous manner as described in example 8A. LR-MS: 698.1 [(M+H)$^+$].

EXAMPLE 187

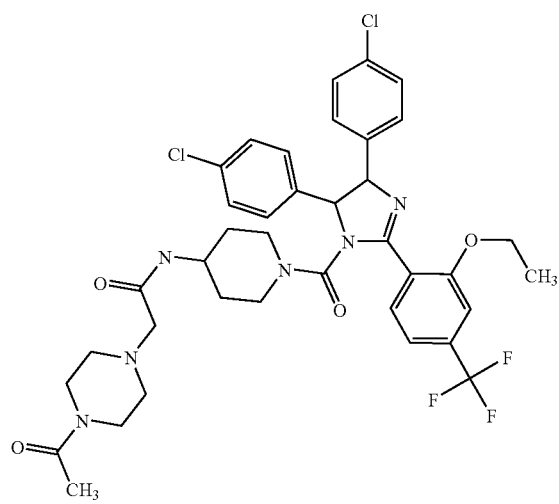

2-(4-Acetyl-piperazin-1-yl)-N-{1-[4,5-bis-(4-chloro-phenyl)-2-(2-ethoxy-4-trifluoromethyl-phenyl)-4,5-dihydro-imidazole-1-carbonyl]-piperidin-4-yl}-acetamide was prepared in an analogous manner as described in example 9. LR-MS: 773.4 [(M+H)$^+$].

EXAMPLE 188

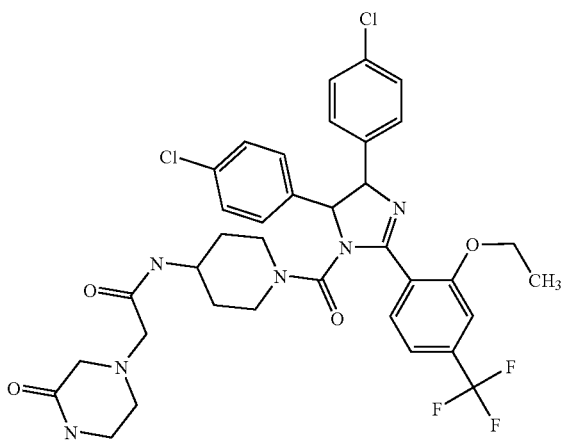

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-(3-oxo-piperazin-1-yl)-acetamide was prepared in an analogous manner as described in example 9. LR-MS: 745.4 [(M+H)$^+$].

EXAMPLE 189

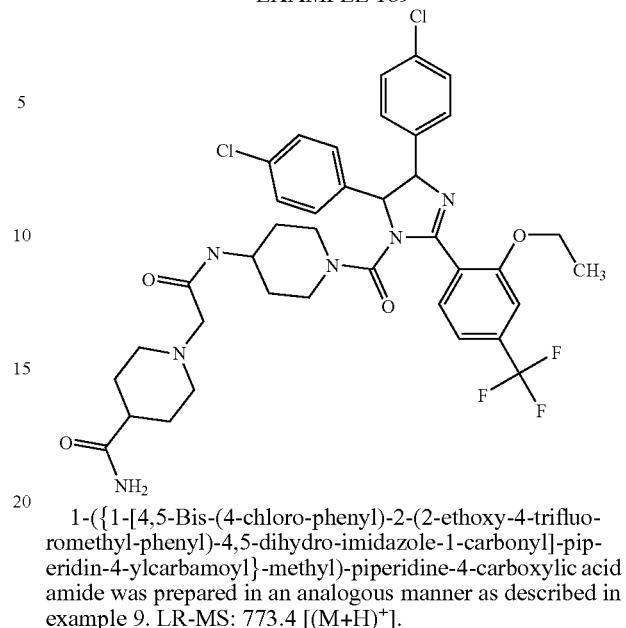

1-({1-[4,5-Bis-(4-chloro-phenyl)-2-(2-ethoxy-4-trifluoromethyl-phenyl)-4,5-dihydro-imidazole-1-carbonyl]-piperidin-4-ylcarbamoyl}-methyl)-piperidine-4-carboxylic acid amide was prepared in an analogous manner as described in example 9. LR-MS: 773.4 [(M+H)$^+$].

EXAMPLE 190

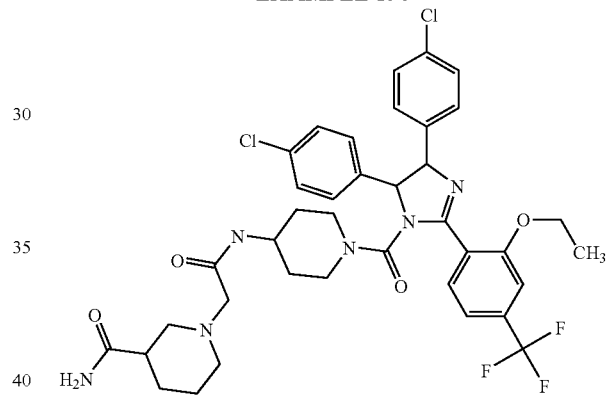

1-({1-[4,5-Bis-(4-chloro-phenyl)-2-(2-ethoxy-4-trifluoromethyl-phenyl)-4,5-dihydro-imidazole-1-carbonyl]-piperidin-4-ylcarbamoyl}-methyl)-piperidine-3-carboxylic acid amide was prepared in an analogous manner as described in example 9. LR-MS: 773.4 [(M+H)$^+$].

EXAMPLE 191

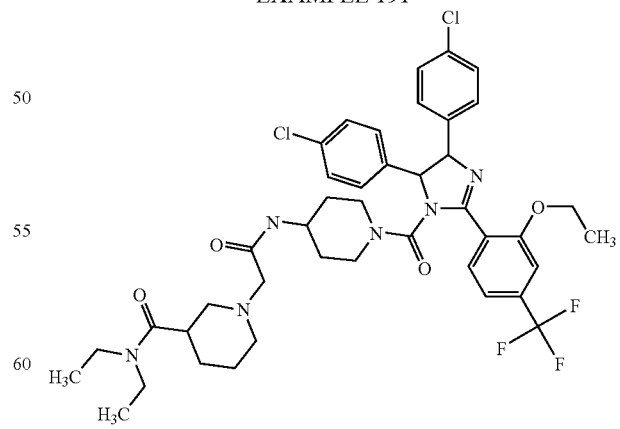

1-({1-[4,5-Bis-(4-chloro-phenyl)-2-(2-ethoxy-4-trifluoromethyl-phenyl)-4,5-dihydro-imidazole-1-carbonyl]-piperidin-4-ylcarbamoyl}-methyl)-piperidine-3-carboxylic acid diethylamide was prepared in an analogous manner as described in example 9. LR-MS: 829.5 [(M+H)$^+$].

EXAMPLE 192

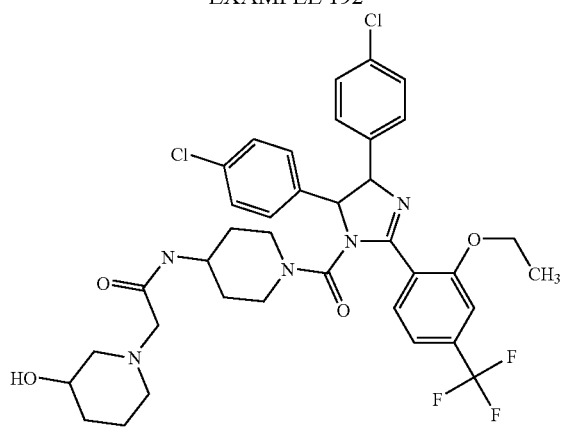

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-(3-hydroxy-piperidin-1-yl)-acetamide was prepared in an analogous manner as described in example 9. LR-MS: 746.4 [(M+H)+].

EXAMPLE 193

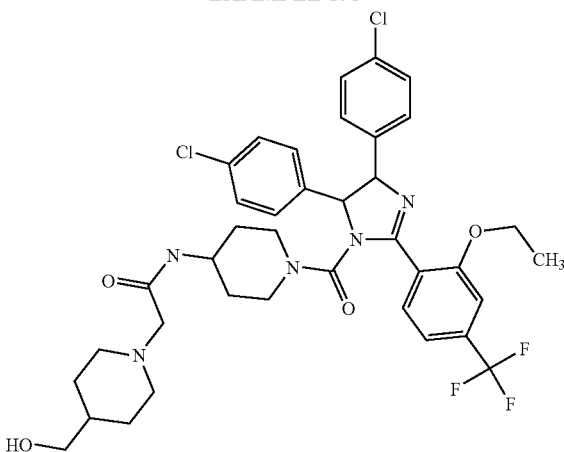

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-(4-hydroxymethyl-piperidin-1-yl)-acetamide was prepared in an analogous manner as described in example 9. LR-MS: 760.7 [(M+H)+].

EXAMPLE 194

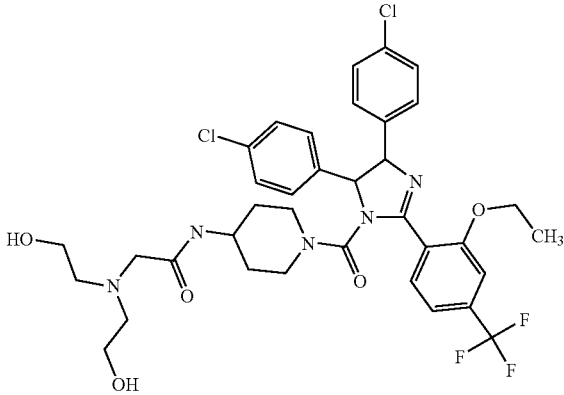

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-[bis-(2-hydroxy-ethyl)-amino]-acetamide was prepared in an analogous manner as described in example 9. LR-MS: 750.4 [(M+H)+].

EXAMPLE 195

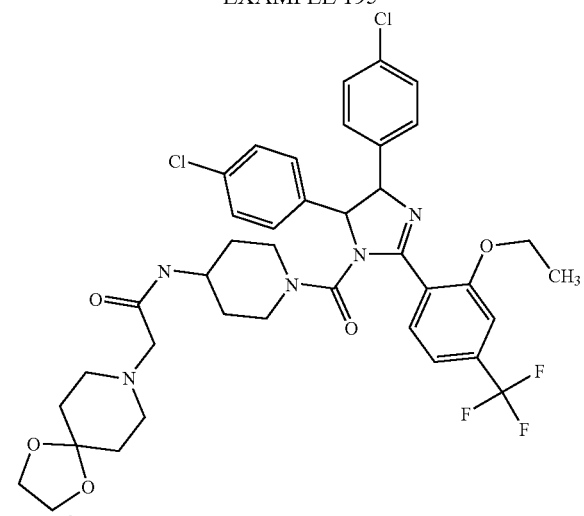

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-(1,4-dioxa-8-aza-spiro[4.5]dec-8-yl)-acetamide was prepared in an analogous manner as described in example 9. LR-MS: 788.4 [(M+H)+].

EXAMPLE 196

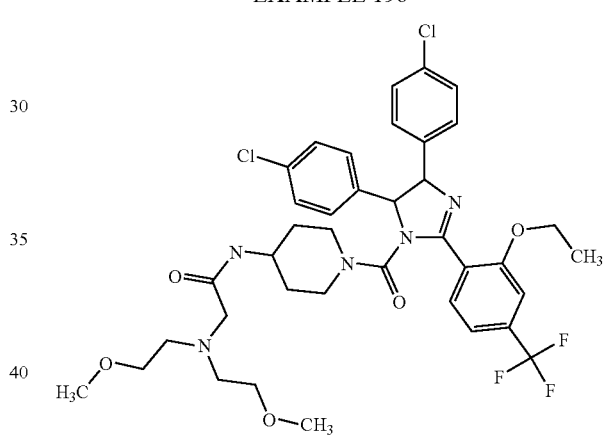

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-[bis-(2-methoxy-ethyl)-amino]-acetamide was prepared in an analogous manner as described in example 9. LR-MS: 778.4 [(M+H)+].

EXAMPLE 197

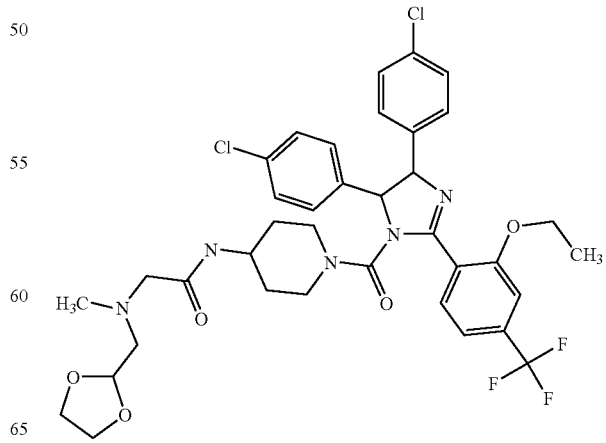

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-([1,3]dioxolan-2-ylmethyl-methyl-amino)-acetamide was prepared in an analogous manner as described in example 9. LR-MS: 762.4 [(M+H)+].

EXAMPLE 198

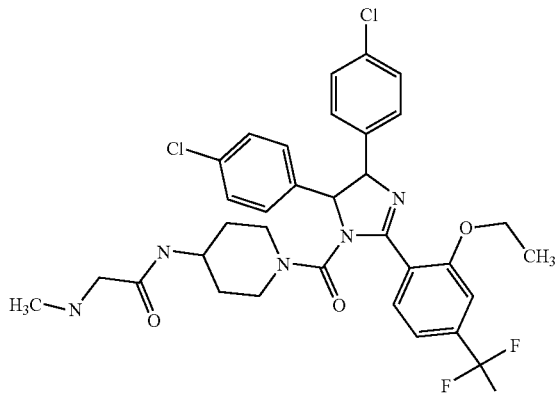

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-methylamino-acetamide was prepared in an analogous manner as described in example 9. LR-MS: 676.4 [(M+H)+].

EXAMPLE 199

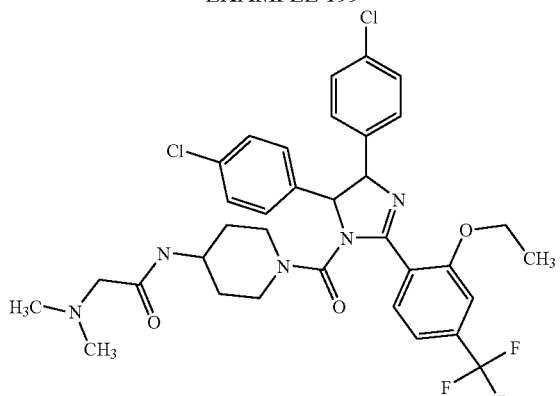

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-dimethylamino-acetamide was prepared in an analogous manner as described in example 9. LR-MS: 690.4 [(M+H)+].

EXAMPLE 200

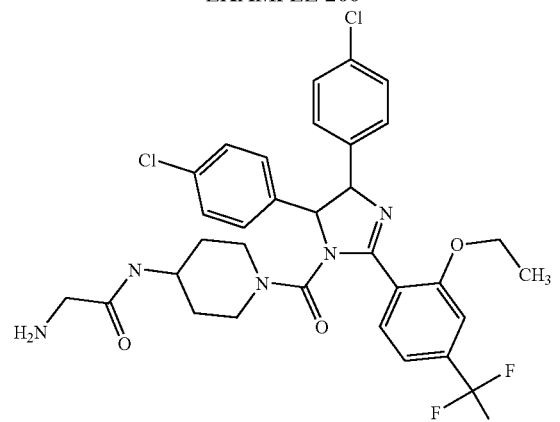

2-Amino-N-{1-[4,5-bis-(4-chloro-phenyl)-2-(2-ethoxy-4-trifluoromethyl-phenyl)-4,5-dihydro-imidazole-1-carbonyl]-piperidin-4-yl}-acetamide was prepared in an analogous manner as described in example 9. LR-MS: 662 [(M+H)+].

EXAMPLE 201

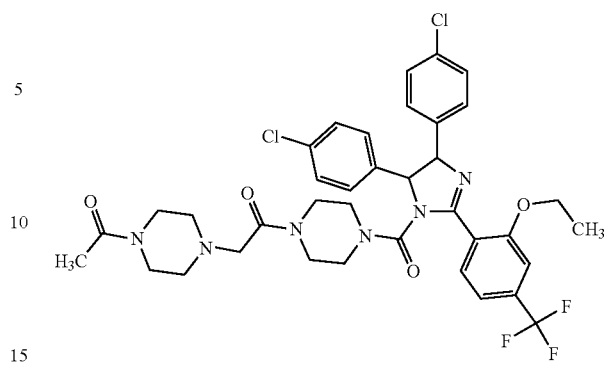

2-(4-Acetyl-piperazin-1-yl)-1-{4-[4,5-bis-(4-chloro-phenyl)-2-(2-ethoxy-4-trifluoromethyl-phenyl)-4,5-dihydro-imidazole-1-carbonyl]-piperazin-1-yl}-ethanone was prepared in an analogous manner as described in example 9. LR-MS: 759.4 [(M+H)+].

EXAMPLE 202

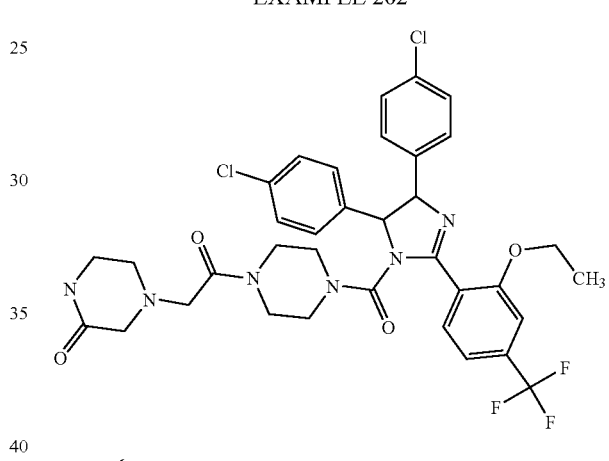

4-(2-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-oxo-ethyl)-piperazin-2-one was prepared in an analogous manner as described in example 9. LR-MS: 732.2 [(M+H)+].

EXAMPLE 203

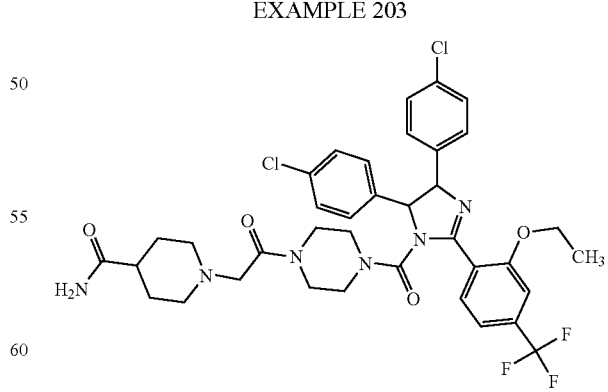

1-(2-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-oxo-ethyl)-piperidine-4-carboxylic acid amide was prepared in an analogous manner as described in example 9. LR-MS: 759.4 [(M+H)+].

EXAMPLE 204

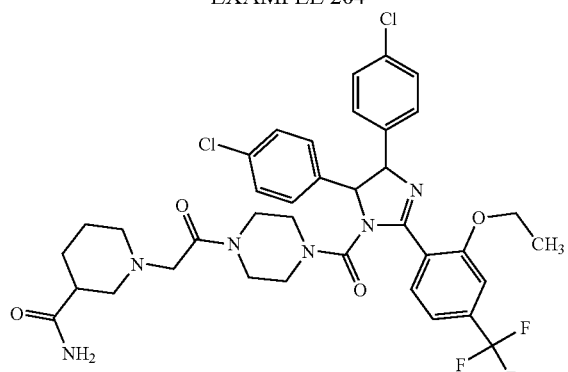

1-(2-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-oxo-ethyl)-piperidine-3-carboxylic acid amide was prepared in an analogous manner as described in example 9. LR-MS: 759.4 [(M+H)$^+$].

EXAMPLE 205

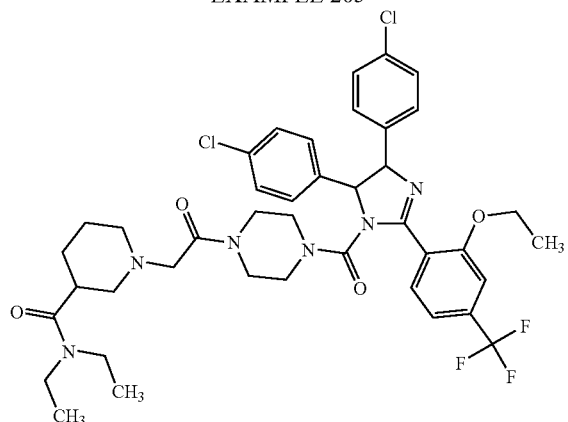

1-(2-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-oxo-ethyl)-piperidine-3-carboxylic acid diethylamide was prepared in an analogous manner as described in example 9. LR-MS: 815.6 [(M+H)$^+$].

EXAMPLE 206

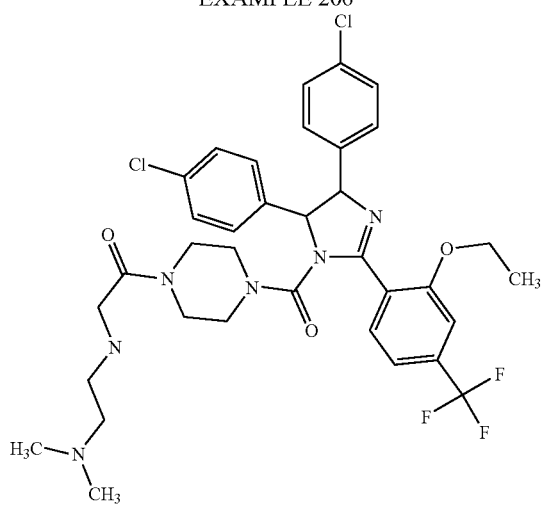

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-(2-dimethylamino-ethylamino)-ethanone was prepared in an analogous manner as described in example 9. LR-MS: 719.7 [(M+H)$^+$].

EXAMPLE 207

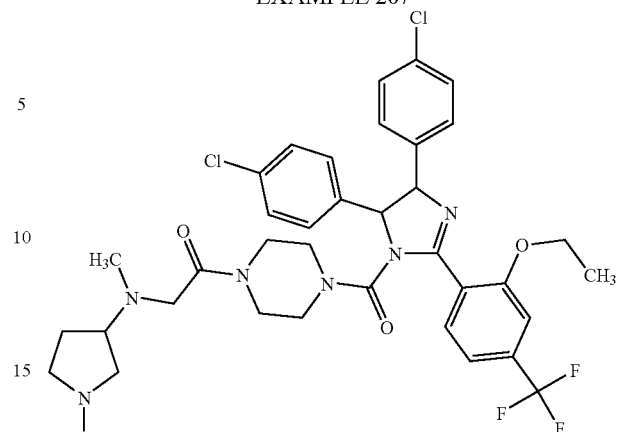

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-[methyl-(1-methyl-pyrrolidin-3-yl)-amino]-ethanone was prepared in an analogous manner as described in example 9. LR-MS: 745.6 [(M+H)$^+$].

EXAMPLE 208

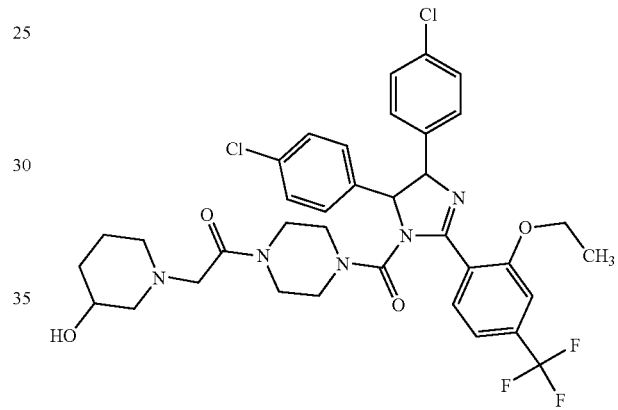

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-(3-hydroxy-piperidin-1-yl)-ethanone was prepared in an analogous manner as described in example 9. LR-MS: 732.6 [(M+H)$^+$].

EXAMPLE 209

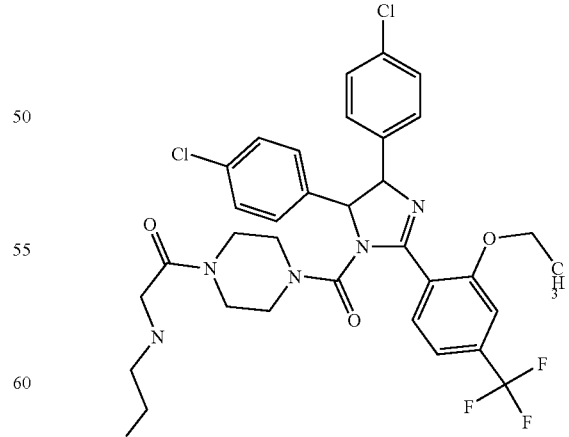

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-(2-hydroxy-ethylamino)-ethanone was prepared in an analogous manner as described in example 9. LR-MS: 692.3 [(M+H)$^+$].

EXAMPLE 210

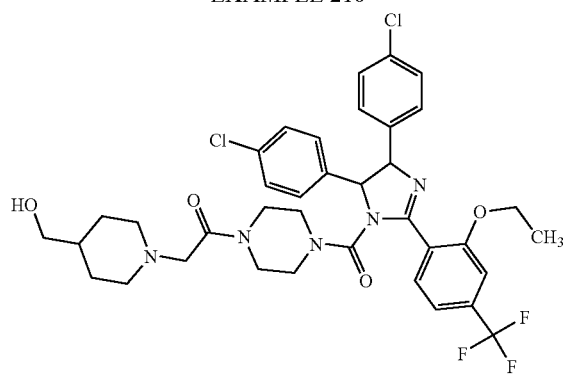

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-(4-hydroxymethyl-piperidin-1-yl)-ethanone was prepared in an analogous manner as described in example 9. LR-MS: 746.4 [(M+H)+].

EXAMPLE 211

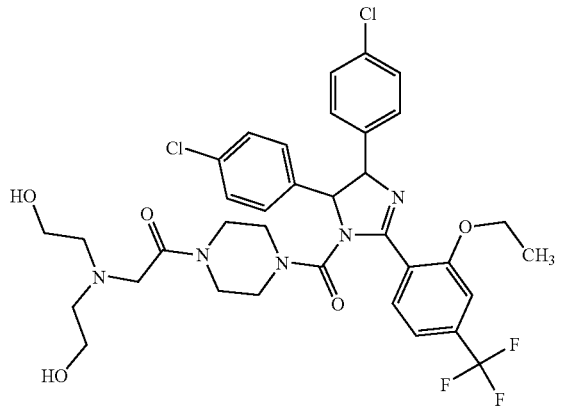

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-[bis-(2-hydroxy-ethyl)-amino]-ethanone was prepared in an analogous manner as described in example 9. LR-MS: 736.4 [(M+H)+].

EXAMPLE 212

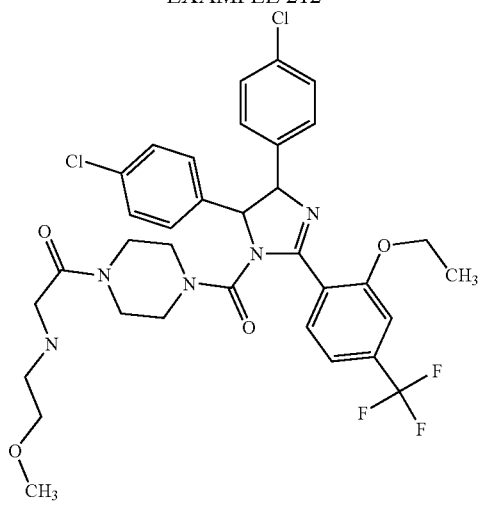

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-(2-methoxy-ethylamino)-ethanone was prepared in an analogous manner as described in example 9. LR-MS: 706.3 [(M+H)+].

EXAMPLE 213

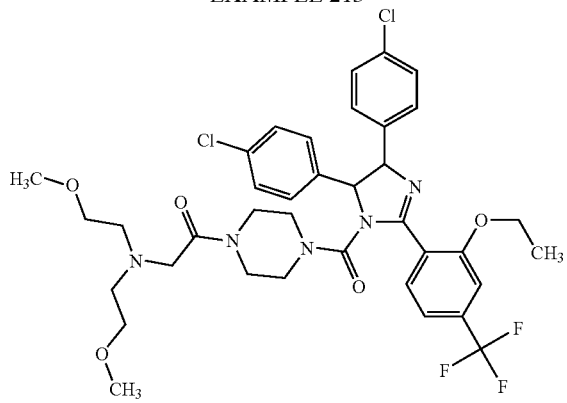

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-[bis-(2-methoxy-ethyl)-amino]-ethanone was prepared in an analogous manner as described in example 9. LR-MS: 764.4 [(M+H)+].

EXAMPLE 214

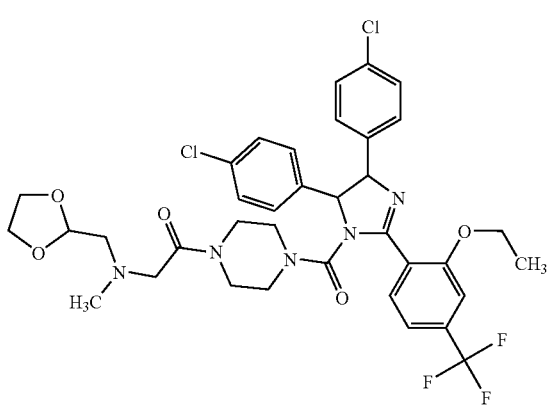

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-([1,3]dioxolan-2-ylmethyl-methyl-amino)-ethanone was prepared in an analogous manner as described in example 9. LR-MS: 748.6 [(M+H)+].

EXAMPLE 215

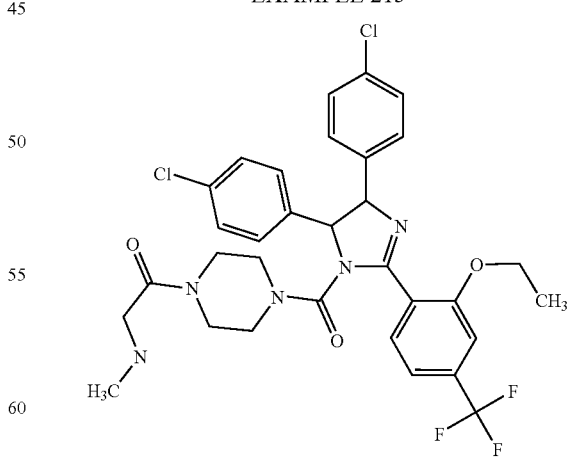

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-methylamino-ethanone was prepared in an analogous manner as described in example 9. LR-MS: 662.1 [(M+H)+].

EXAMPLE 216

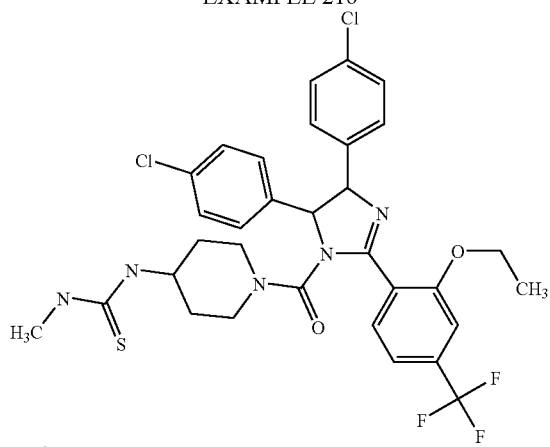

1-{1-[4,5-Bis-(4-chloro-phenyl)-2-(2-ethoxy-4-trifluoromethyl-phenyl)-4,5-dihydro-imidazole-1-carbonyl]-piperidin-4-yl}-3-methyl-thiourea was prepared in an analogous manner as described in example 10. LR-MS: 678.3 [(M+H)$^+$].

EXAMPLE 217

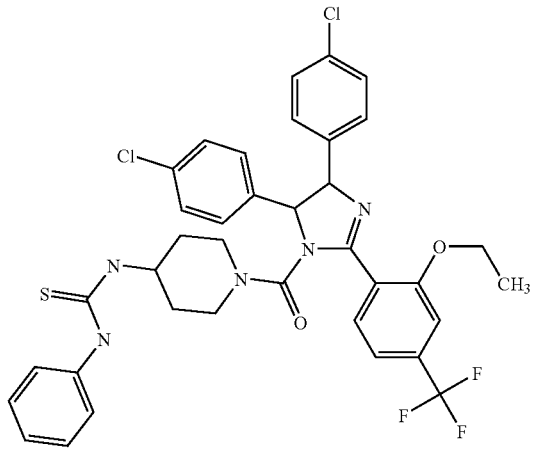

1-{1-[4,5-Bis-(4-chloro-phenyl)-2-(2-ethoxy-4-trifluoromethyl-phenyl)-4,5-dihydro-imidazole-1-carbonyl]-piperidin-4-yl}-3-phenyl-thiourea was prepared in an analogous manner as described in example 10. LR-MS: 740.3 [(M+H)$^+$].

EXAMPLE 218

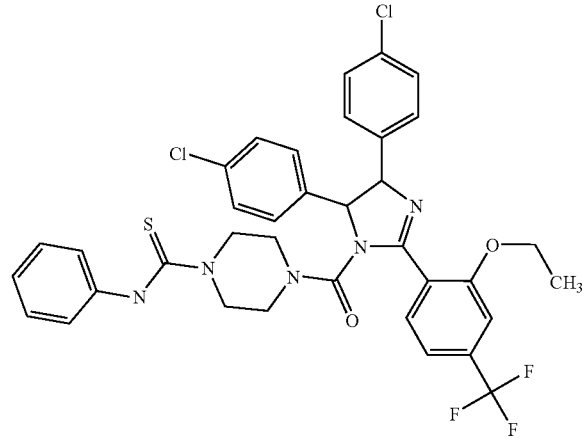

4-[4,5-Bis-(4-chloro-phenyl)-2-(2-ethoxy-4-trifluoromethyl-phenyl)-4,5-dihydro-imidazole-1-carbonyl]-piperazine-1-carbothioic acid phenylamide was prepared in an analogous manner as described in example 10. LR-MS: 726.3 [(M+H)$^+$].

EXAMPLE 219

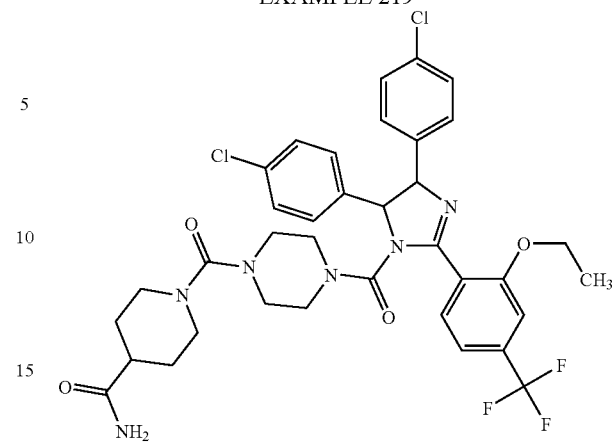

1-{4-[4,5-Bis-(4-chloro-phenyl)-2-(2-ethoxy-4-trifluoromethyl-phenyl)-4,5-dihydro-imidazole-1-carbonyl]-piperazine-1-carbonyl}-piperidine-4-carboxylic acid amide was prepared in an analogous manner as described in example 11. LR-MS: 745.5 [(M+H)$^+$].

EXAMPLE 220

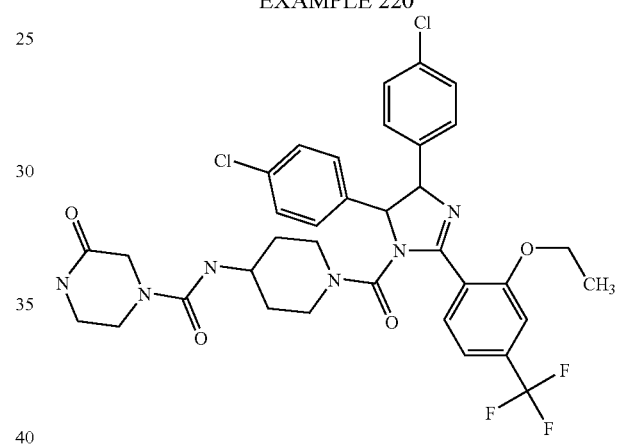

3-Oxo-piperazine-1-carboxylic acid {1-[4,5-bis-(4-chloro-phenyl)-2-(2-ethoxy-4-trifluoromethyl-phenyl)-4,5-dihydro-imidazole-1-carbonyl]-piperidin-4-yl}-amide was prepared in an analogous manner as described in example 11. LR-MS: 732.4 [(M+H)$^+$].

EXAMPLE 221

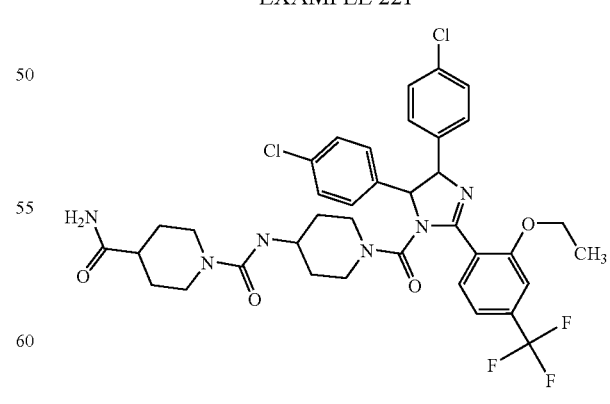

Piperidine-1,4-dicarboxylic acid 4-amide 1-({1-[4,5-bis-(4-chloro-phenyl)-2-(2-ethoxy-4-trifluoromethyl-phenyl)-4,5-dihydro-imidazole-1-carbonyl]-piperidin-4-yl}-amide) was prepared in an analogous manner as described in example 11. LR-MS: 759.5 [(M+H)$^+$].

EXAMPLE 222

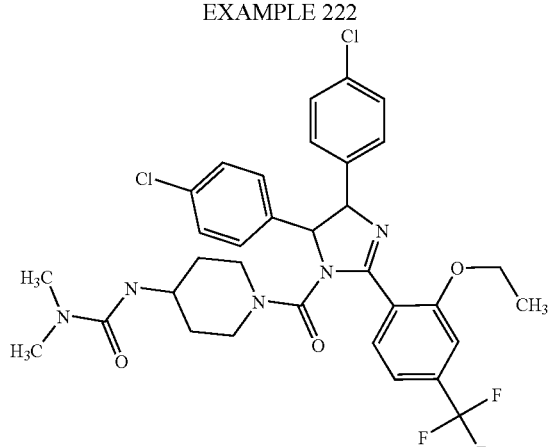

3-{1-[4,5-Bis-(4-chloro-phenyl)-2-(2-ethoxy-4-trifluoromethyl-phenyl)-4,5-dihydro-imidazole-1-carbonyl]-piperidin-4-yl}-1,1-dimethyl-urea was prepared in an analogous manner as described in example 11. LR-MS: 676.4 [(M+H)$^+$].

EXAMPLE 223

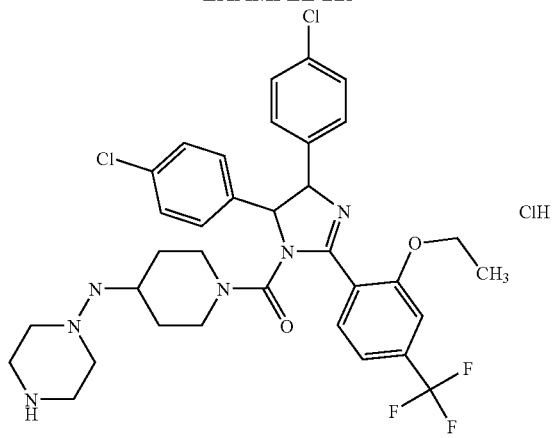

[4,5-Bis-(4-chloro-phenyl)-2-(2-ethoxy-4-trifluoromethyl-phenyl)-4,5-dihydro-imidazol-1-yl]-(4-piperazin-1-ylmethyl-piperidin-1-yl)-methanone hydrochloride was prepared in an analogous manner as described in example 13A. LR-MS: 688.4 [(M+H)$^+$].

EXAMPLE 224

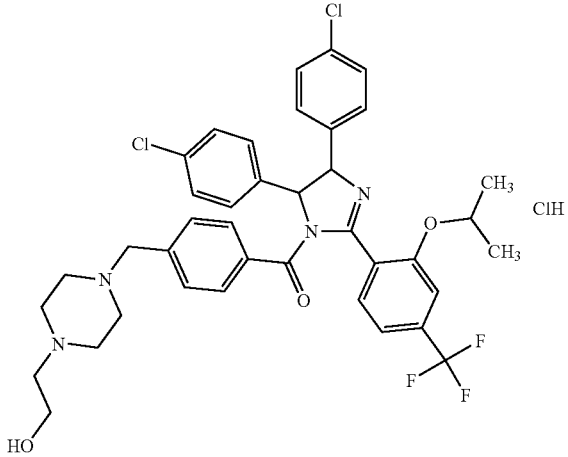

[4,5-Bis-(4-chloro-phenyl)-2-(2-isopropoxy-4-trifluoromethyl-phenyl)-4,5-dihydro-imidazol-1-yl]-{4-[4-(2-hydroxy-ethyl)-piperazin-1-ylmethyl]-phenyl}-methanone hydrochloride was prepared in an analogous manner as described in example 14. LR-MS: 741.6 [(M+H)$^+$].

EXAMPLE 225

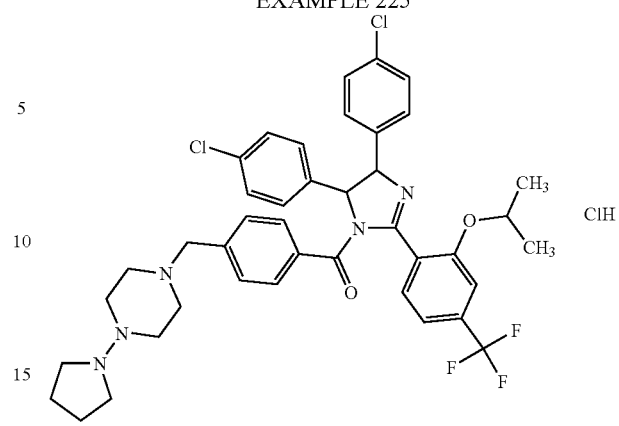

[4,5-Bis-(4-chloro-phenyl)-2-(2-isopropoxy-4-trifluoromethyl-phenyl)-4,5-dihydro-imidazol-1-yl]-[4-(4-pyrrolidin-1-yl-piperidin-1-ylmethyl)-phenyl]-methanone hydrochloride was prepared in an analogous manner as described in example 14. LR-MS: 763.3 [(M+H)$^+$].

EXAMPLE 226

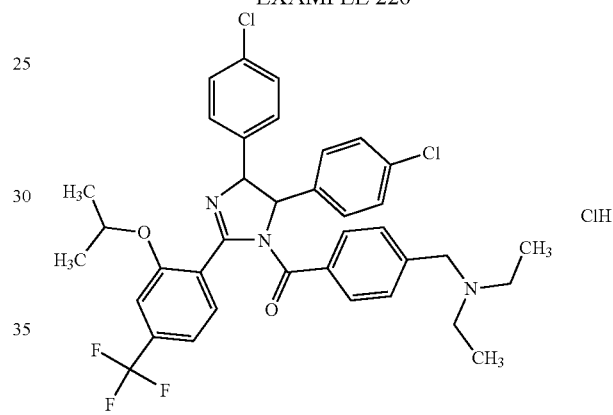

[4,5-Bis-(4-chloro-phenyl)-2-(2-isopropoxy-4-trifluoromethyl-phenyl)-4,5-dihydro-imidazol-1-yl]-(4-diethylaminomethyl-phenyl)-methanone hydrochloride was prepared in an analogous manner as described in example 14. LR-MS: 682.3 [(M+H)$^+$].

EXAMPLE 227

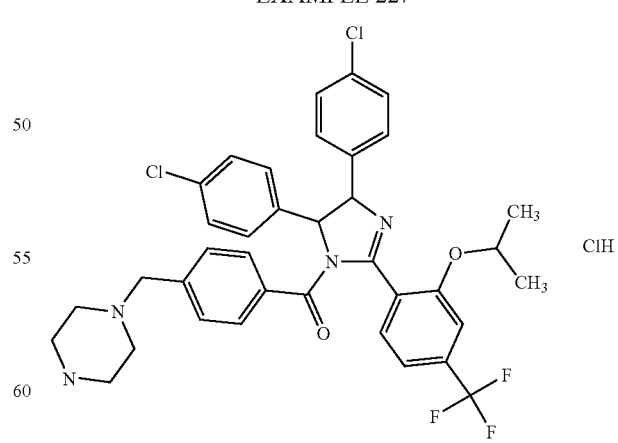

[4,5-Bis-(4-chloro-phenyl)-2-(2-isopropoxy-4-trifluoromethyl-phenyl)-4,5-dihydro-imidazol-1-yl]-(4-piperazin-1-ylmethyl-phenyl)-methanone hydrochloride was prepared in an analogous manner as described in example 14. LR-MS: 695.3 [(M+H)$^+$].

EXAMPLE 228

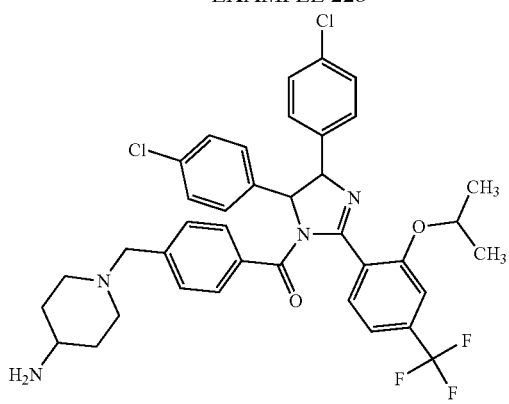

[4-(4-Amino-piperidin-1-ylmethyl)-phenyl]-[4,5-bis-(4-chloro-phenyl)-2-(2-isopropoxy-4-trifluoromethyl-phenyl)-4,5-dihydro-imidazol-1-yl]-methanone hydrochloride was prepared in an analogous manner as described in example 14. LR-MS: 709.3 [(M+H)+].

EXAMPLE 229

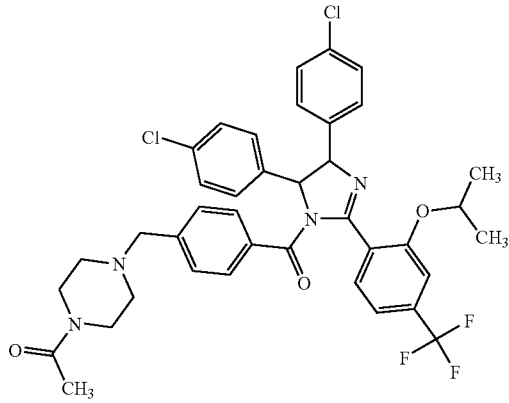

1-(4-{4-[4,5-Bis-(4-chloro-phenyl)-2-(2-isopropoxy-4-trifluoromethyl-phenyl)-4,5-dihydro-imidazole-1-carbonyl]-benzyl}-piperazin-1-yl)-ethanone hydrochloride was prepared in an analogous manner as described in example 14. LR-MS: 737.3 [(M+H)+].

EXAMPLE 230

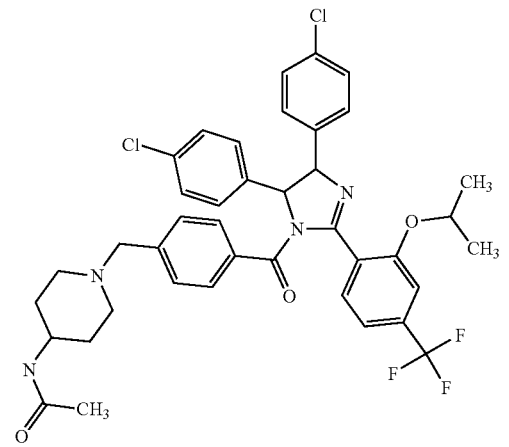

N-(1-{4-[4,5-Bis-(4-chloro-phenyl)-2-(2-isopropoxy-4-trifluoromethyl-phenyl)-4,5-dihydro-imidazole-1-carbonyl]-benzyl}-piperidin-4-yl)-acetamide hydrochloride was prepared in an analogous manner as described in example 14. LR-MS: 751.4 [(M+H)+].

EXAMPLE 231

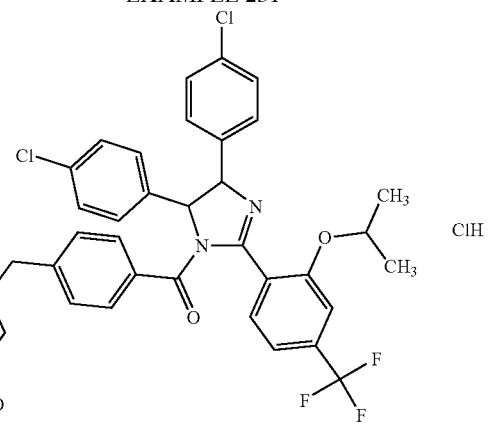

4-{4-[4,5-Bis-(4-chloro-phenyl)-2-(2-isopropoxy-4-trifluoromethyl-phenyl)-4,5-dihydro-imidazole-1-carbonyl]-benzyl}-piperazin-2-one hydrochloride was prepared in an analogous manner as described in example 14. LR-MS: 709.3 [(M+H)+].

EXAMPLE 232

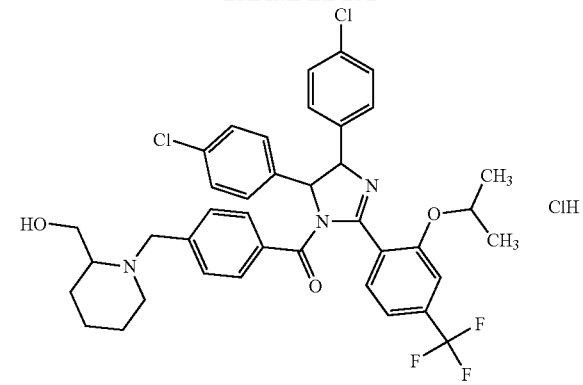

[4,5-Bis-(4-chloro-phenyl)-2-(2-isopropoxy-4-trifluoromethyl-phenyl)-4,5-dihydro-imidazol-1-yl]-[4-(2-hydroxymethyl-piperidin-1-ylmethyl)-phenyl]-methanone hydrochloride was prepared in an analogous manner as described in example 14. LR-MS: 724.3 [(M+H)+].

EXAMPLE 233

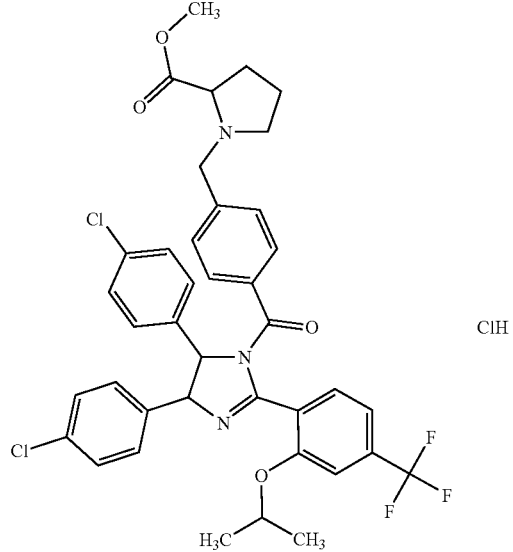

1-{4-[4,5-Bis-(4-chloro-phenyl)-2-(2-isopropoxy-4-trifluoromethyl-phenyl)-4,5-dihydro-imidazole-1-carbonyl]-benzyl}-pyrrolidine-2-carboxylic acid methyl ester hydrochloride was prepared in an analogous manner as described in example 14. LR-MS: 738.3 [(M+H)+].

EXAMPLE 234

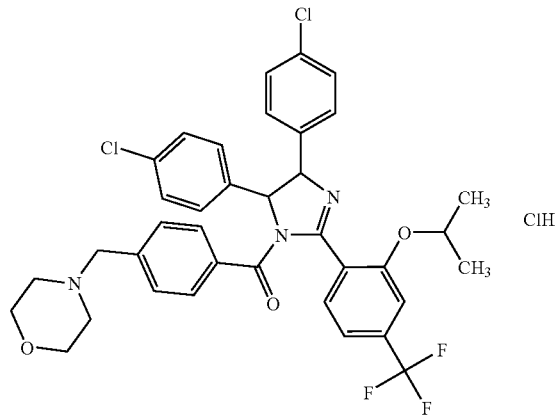

[4,5-Bis-(4-chloro-phenyl)-2-(2-isopropoxy-4-trifluoromethyl-phenyl)-4,5-dihydro-imidazol-1-yl]-(4-morpholin-4-ylmethyl-phenyl)-methanone hydrochloride was prepared in an analogous manner as described in example 14. LR-MS: 696.3 [(M+H)+].

EXAMPLE 235

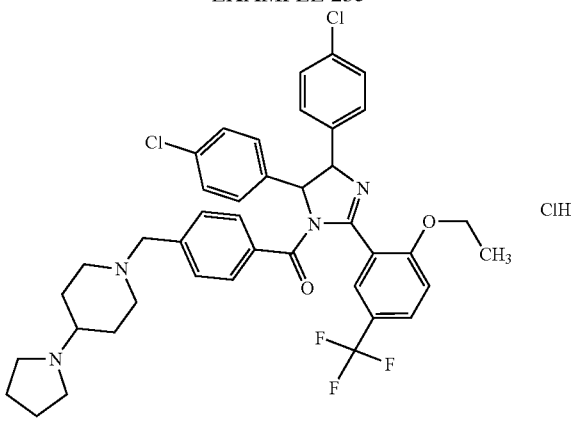

[4,5-Bis-(4-chloro-phenyl)-2-(2-ethoxy-5-trifluoromethyl-phenyl)-4,5-dihydro-imidazol-1-yl]-[4-(4-pyrrolidin-1-yl-piperidin-1-ylmethyl)-phenyl]-methanone hydrochloride was prepared in an analogous manner as described in example 14. LR-MS: 749.4 [(M+H)+].

EXAMPLE 236

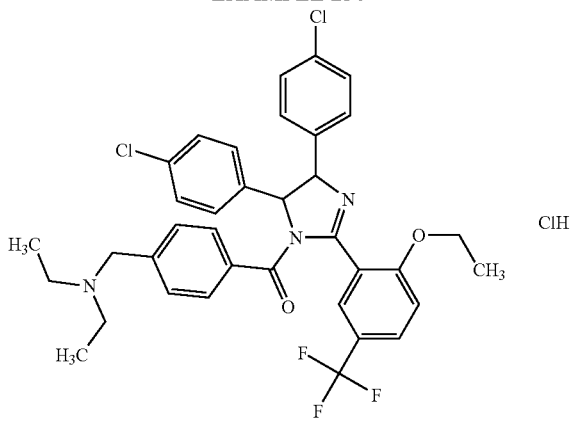

[4,5-Bis-(4-chloro-phenyl)-2-(2-ethoxy-5-trifluoromethyl-phenyl)-4,5-dihydro-imidazol-1-yl]-(4-diethylaminomethyl-phenyl)-methanone hydrochloride was prepared in an analogous manner as described in example 14. LR-MS: 668.1 [(M+H)+].

EXAMPLE 237

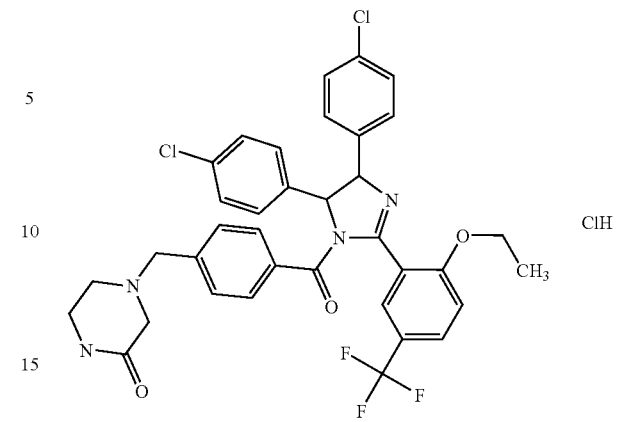

4-{4-[4,5-Bis-(4-chloro-phenyl)-2-(2-ethoxy-5-trifluoromethyl-phenyl)-4,5-dihydro-imidazole-1-carbonyl]-benzyl}-piperazin-2-one hydrochloride was prepared in an analogous manner as described in example 14. LR-MS: 695.3 [(M+H)+].

EXAMPLE 238

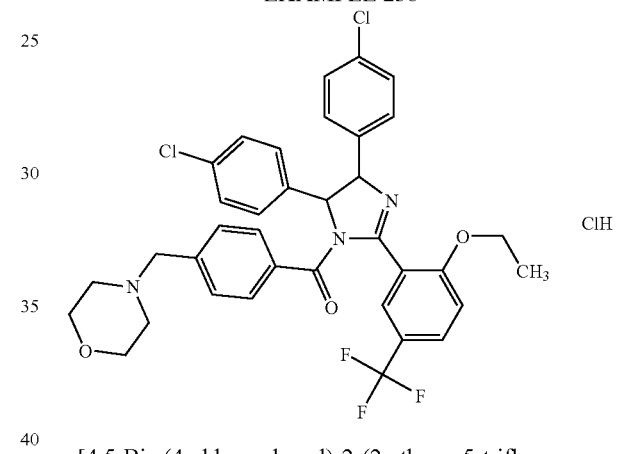

[4,5-Bis-(4-chloro-phenyl)-2-(2-ethoxy-5-trifluoromethyl-phenyl)-4,5-dihydro-imidazol-1-yl]-(4-morpholin-4-ylmethyl-phenyl)-methanone was prepared in an analogous manner as described in example 14. LR-MS: 682.3 [(M+H)+].

EXAMPLE 239

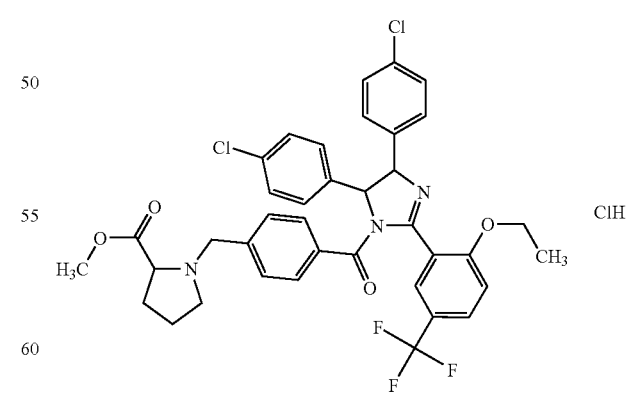

1-{4-[4,5-Bis-(4-chloro-phenyl)-2-(2-ethoxy-5-trifluoromethyl-phenyl)-4,5-dihydro-imidazole-1-carbonyl]-benzyl}-pyrrolidine-2-carboxylic acid methyl ester hydrochloride was prepared in an analogous manner as described in example 14. LR-MS: 724.3 [(M+H)+].

EXAMPLE 240

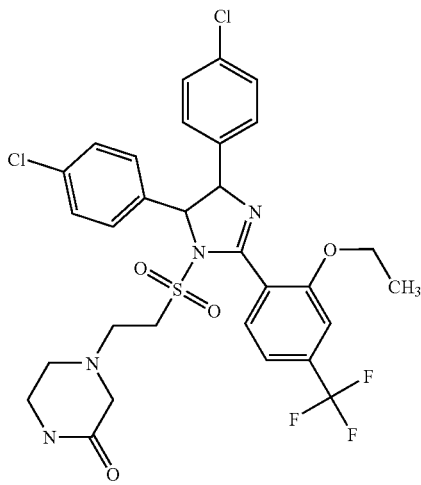

4-{2-[4,5-Bis-(4-chloro-phenyl)-2-(2-ethoxy-4-trifluoromethyl-phenyl)-4,5-dihydro-imidazole-1-sulfonyl]-ethyl}-piperazin-2-one hydrochloride was prepared in an analogous manner as described in example 15. LR-MS: 669.2 [(M+H)$^+$].

EXAMPLE 241

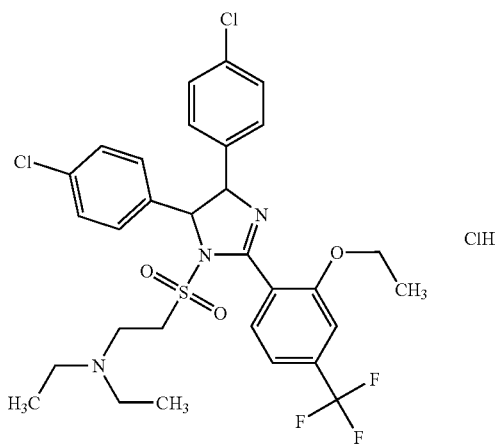

{2-[4,5-Bis-(4-chloro-phenyl)-2-(2-ethoxy-4-trifluoromethyl-phenyl)-4,5-dihydro-imidazole-1-sulfonyl]-ethyl}-diethyl-amine hydrochloride was prepared in an analogous manner as described in example 15. LR-MS: 642.2 [(M+H)$^+$].

EXAMPLE 242

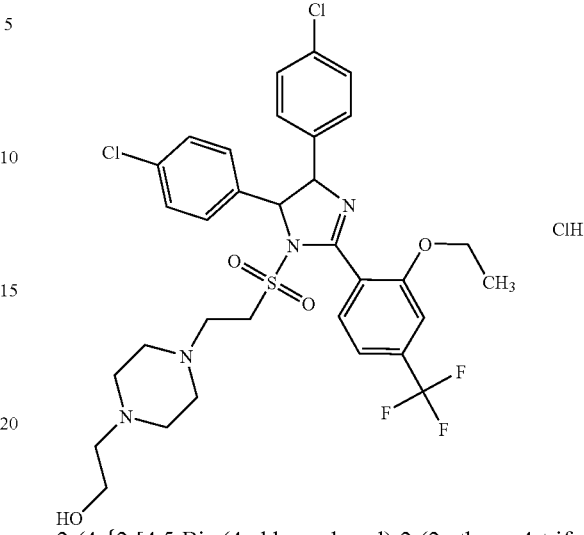

2-(4-{2-[4,5-Bis-(4-chloro-phenyl)-2-(2-ethoxy-4-trifluoromethyl-phenyl)-4,5-dihydro-imidazole-1-sulfonyl]-ethyl}-piperazin-1-yl)-ethanol hydrochloride was prepared in an analogous manner as described in example 15. LR-MS: 699.3 [(M+H)$^+$].

EXAMPLE 243

In Vitro Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

IC$_{50}$s showing biological activity that applies to compounds of the subject matter of this invention ranges from about 0.020 uM to about 5 uM. Specific data for some examples are as follows:

| Example | IC$_{50}$ (µM) |
|---------|----------------|
| 6 | 0.100 |
| 16 | 1.740 |
| 26 | 0.800 |
| 36 | 4.260 |
| 176 | 0.021 |

What is claimed is:

1. A compound selected from the group consisting of:
[4,5-Bis-(4-chloro-phenyl)-2-(2-ethoxy-4-trifluoromethyl-phenyl)-4,5-dihydro-imidazol-1-yl]-[4-(propane-2-sulfonyl)-piperazin-1-yl]-methanone;
1-Benzyl-4-[4,5-bis-(4-chloro-phenyl)-2-(2-ethoxy-4-trifluoromethyl-phenyl)-4,5-dihydro-imidazole-1-carbonyl]-piperazin-2-one hydrochloride;
[4,5-Bis-(4-chloro-phenyl)-2-(2-ethoxy-4-trifluoromethyl-phenyl)-4,5-dihydro-imidazol-1-yl]-[4-(morpholine-4-sulfonyl)-piperazin-1-yl]-methanone;
3-{4-[4,5-Bis-(4-chloro-phenyl)-2-(2-ethoxy-4-trifluoromethyl-phenyl)-4,5-dihydro-imidazole-1-carbonyl]-piperazin-1-yl}-propionitrile hydrochloride;
2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-methyl-acetamide;
4-[4,5-Bis-(4-chloro-phenyl)-2-(2-ethoxy-4-trifluoromethyl-phenyl)-4,5-dihydro-imidazole-1-carbonyl]-piperazine-1-carbothioic acid methylamide;
4-{4-[4,5-Bis-(4-chloro-phenyl)-2-(2-ethoxy-4-trifluoromethyl-phenyl)-4,5-dihydro-imidazole-1-carbonyl]-piperazine-1-carbonyl}-piperazin-2-one;
4-{1-[4,5-Bis-(4-chloro-phenyl)-2-(2-ethoxy-4-trifluoromethyl-phenyl)-4,5-dihydro-imidazole-1-carbonyl]-piperidin-4-ylmethyl}-piperazin-2-one hydrochloride;
[4,5-Bis-(4-chloro-phenyl)-2-(2-ethoxy-4-trifluoromethyl-phenyl)-4,5-dihydro-imidazol-1-yl]-[4-(3,3,3-trifluoro-2-hydroxy-propyl)-piperazin-1-yl]-methanone hydrochloride;
[4,5-Bis-(4-chloro-phenyl)-2-(2-ethoxy-5-trifluoromethyl-phenyl)-4,5-dihydro-imidazol-1-yl]-{4-[4-(2-hydroxy-ethyl)-piperazin-1-ylmethyl]-phenyl}-methanone hydrochloride;
4-{2-[4,5-Bis-(4-chloro-phenyl)-2-(2-ethoxy-4-trifluoromethyl-phenyl)-4,5-dihydro-imidazole-1-sulfonyl]-ethyl}-morpholine hydrochloride;
1-[4,5-Bis-(4-chloro-phenyl)-2-(2-ethoxy-4-trifluoromethyl-phenyl)-4,5-dihydro-imidazole-1-carbonyl]-piperidine-4-carboxylic acid methyl ester;
4,5-Bis-(4-chloro-phenyl)-2-(2-ethoxy-4-trifluoromethyl-phenyl)-4,5-dihydro-imidazole-1-carboxylic acid cyanomethyl-methyl-amide;
[4,5-Bis-(4-chloro-phenyl)-2-(2-ethoxy-4-trifluoromethyl-phenyl)-4,5-dihydro-imidazol-1-yl]-(1,4-dioxa-8-aza-spiro[4.5]dec-8-yl)-methanone;
1-[4,5-Bis-(4-chloro-phenyl)-2-(2-ethoxy-4-trifluoromethyl-phenyl)-4,5-dihydro-imidazole-1-carbonyl]-piperidine-3-carboxylic acid ethyl ester;
4,5-Bis-(4-chloro-phenyl)-2-(2-ethoxy-4-trifluoromethyl-phenyl)-4,5-dihydro-imidazole-1-carboxylic acid [1,3]dioxolan-2-ylmethyl-methyl-amide;
4,5-Bis-(4-chloro-phenyl)-2-(2-ethoxy-4-trifluoromethyl-phenyl)-4,5-dihydro-imidazole-1-carboxylic acid (3-hydroxy-propyl)-amide;
4,5-Bis-(4-chloro-phenyl)-2-(2-ethoxy-4-trifluoromethyl-phenyl)-4,5-dihydro-imidazole-1-carboxylic acid [2-(1-methyl-pyrrolidin-2-yl)-ethyl]-amide;
4,5-Bis-(4-chloro-phenyl)-2-(2-ethoxy-4-trifluoromethyl-phenyl)-4,5-dihydro-imidazole-1-carboxylic acid (2-pyridin-2-yl-ethyl)-amide;
4,5-Bis-(4-chloro-phenyl)-2-(2-ethoxy-4-trifluoromethyl-phenyl)-4,5-dihydro-imidazole-1-carboxylic acid (furan-2-ylmethyl)-amide;
4,5-Bis-(4-chloro-phenyl)-2-(2-ethoxy-4-trifluoromethyl-phenyl)-4,5-dihydro-imidazole-1-carboxylic acid (pyridin-3-ylmethyl)-amide;
1-{1-[4,5-Bis-(4-chloro-phenyl)-2-(2-ethoxy-4-trifluoromethyl-phenyl)-4,5-dihydro-imidazole-1-carbonyl]-piperidin-4-yl}-1,3-dihydro-benzoimidazol-2-one;
4,5-Bis-(4-chloro-phenyl)-2-(2-ethoxy-4-trifluoromethyl-phenyl)-4,5-dihydro-imidazole-1-carboxylic acid methyl-(1-methyl-pyrrolidin-3-yl)-amide;
1-[4,5-Bis-(4-chloro-phenyl)-2-(2-ethoxy-4-trifluoromethyl-phenyl)-4,5-dihydro-imidazole-1-carbonyl]-piperidine-2-carboxylic acid ethyl ester;
[4,5-Bis-(4-chloro-phenyl)-2-(2-ethoxy-4-trifluoromethyl-phenyl)-4,5-dihydro-imidazol-1-yl]-(4-pyrimidin-2-yl-piperazin-1-yl)-methanone;
4,5-Bis-(4-chloro-phenyl)-2-(2-ethoxy-4-trifluoromethyl-phenyl)-4,5-dihydro-imidazole-1-carboxylic acid 3-methoxy-benzylamide;
4,5-Bis-(4-chloro-phenyl)-2-(2-ethoxy-4-trifluoromethyl-phenyl)-4,5-dihydro-imidazole-1-carboxylic acid (2-hydroxy-ethyl)-amide;
4,5-Bis-(4-chloro-phenyl)-2-(2-ethoxy-4-trifluoromethyl-phenyl)-4,5-dihydro-imidazole-1-carboxylic acid (2-hydroxy-ethyl)-methyl-amide;
4,5-Bis-(4-chloro-phenyl)-2-(2-ethoxy-4-trifluoromethyl-phenyl)-4,5-dihydro-imidazole-1-carboxylic acid (2-methoxy-1-methyl-ethyl)-amide;
4,5-Bis-(4-chloro-phenyl)-2-(2-ethoxy-4-trifluoromethyl-phenyl)-4,5-dihydro-imidazole-1-carboxylic acid (1-ethyl-pyrrolidin-2-ylmethyl)-amide;
4,5-Bis-(4-chloro-phenyl)-2-(2-ethoxy-4-trifluoromethyl-phenyl)-4,5-dihydro-imidazole-1-carboxylic acid (2-cyano-ethyl)-methyl-amide;
4,5-Bis-(4-chloro-phenyl)-2-(2-ethoxy-4-trifluoromethyl-phenyl)-4,5-dihydro-imidazole-1-carboxylic acid methyl-pyridin-2-yl-amide;
4,5-Bis-(4-chloro-phenyl)-2-(2-ethoxy-4-trifluoromethyl-phenyl)-4,5-dihydro-imidazole-1-carboxylic acid methyl-(1-methyl-piperidin-4-yl)-amide;
4,5-Bis-(4-chloro-phenyl)-2-(2-ethoxy-4-trifluoromethyl-phenyl)-4,5-dihydro-imidazole-1-carboxylic acid furan-2-ylmethyl-methyl-amide;
4,5-Bis-(4-chloro-phenyl)-2-(2-ethoxy-4-trifluoromethyl-phenyl)-4,5-dihydro-imidazole-1-carboxylic acid (2-hydroxy-benzyl)-methyl-amide;
4,5-Bis-(4-chloro-phenyl)-2-(2-ethoxy-4-trifluoromethyl-phenyl)-4,5-dihydro-imidazole-1-carboxylic acid 4-sulfamoyl-benzylamide;
4,5-Bis-(4-chloro-phenyl)-2-(2-ethoxy-4-trifluoromethyl-phenyl)-4,5-dihydro-imidazole-1-carboxylic acid methoxy-methyl-amide;
4,5-Bis-(4-chloro-phenyl)-2-(2-ethoxy-4-trifluoromethyl-phenyl)-4,5-dihydro-imidazole-1-carboxylic acid (3-imidazol-1-yl-propyl)-amide;
1-[4,5-Bis-(4-chloro-phenyl)-2-(2-ethoxy-4-trifluoromethyl-phenyl)-4,5-dihydro-imidazole-1-carbonyl]-pyrrolidine-2-carboxylic acid methyl ester;
[4,5-Bis-(4-chloro-phenyl)-2-(2-ethoxy-4-trifluoromethyl-phenyl)-4,5-dihydro-imidazol-1-yl]-[4-(3-pyrrolidin-1-yl-propyl)-piperazin-1-yl]-methanone;
[4,5-Bis-(4-chloro-phenyl)-2-(2-ethoxy-4-trifluoromethyl-phenyl)-4,5-dihydro-imidazol-1-yl]-[4-(furan-2-carbonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-(4-pyridin-4-yl-piperazin-1-yl)-methanone;

[4,5-Bis-(4-chloro-phenyl)-2-(2-ethoxy-4-trifluoromethyl-phenyl)-4,5-dihydro-imidazol-1-yl]-[4-(2,3-dihydro-benzo[1,4]dioxine-2-carbonyl)-piperazin-1-yl]-methanone;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-l-piperidin-1-yl-ethanone;

[4,5-Bis-(4-chloro-phenyl)-2-(2-ethoxy-4-trifluoromethyl-phenyl)-4,5-dihydro-imidazol-1-yl]-[4-(2-morpholin-4-yl-ethyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(3-piperidin-1-yl-propyl)-piperazin-1-yl]-methanone;

4,5-Bis-(4-chloro-phenyl)-2-(2-ethoxy-4-trifluoromethyl-phenyl)-4,5-dihydro-imidazole-1-carboxylic acid [2-(2-oxo-imidazolidin-1-yl)-ethyl]-amide; and

[4,5-Bis-(4-chloro-phenyl)-2-(2-ethoxy-4-trifluoromethyl-phenyl)-4,5-dihydro-imidazol-1-yl]-[4-(3-dipropylamino-propyl)-piperazin-1-yl]-methanone.

2. A compound selected from the group consisting of:

6-{4-[4,5-Bis-(4-chloro-phenyl)-2-(2-ethoxy-4-trifluoromethyl-phenyl)-4,5-dihydro-imidazole-1-carbonyl]-piperazin-1-yl}-nicotinonitrile;

[4,5-Bis-(4-chloro-phenyl)-2-(2-ethoxy-4-trifluoromethyl-phenyl)-4,5-dihydro-imidazol-1-yl]-[4-(3-dimethylamino-propyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-(4-pyridin-4-ylmethyl-piperazin-1-yl)-methanone;

{4-[4,5-Bis-(4-chloro-phenyl)-2-(2-ethoxy-4-trifluoromethyl-phenyl)-4,5-dihydro-imidazole-1-carbonyl]-piperazin-1-yl}-acetic acid ethyl ester;

[4,5-Bis-(4-chloro-phenyl)-2-(2-ethoxy-4-trifluoromethyl-phenyl)-4,5-dihydro-imidazol-1-yl]-[4-(2-ethoxy-ethyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(2-diisopropylamino-ethyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(2-dimethylamino-ethyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(tetrahydro-furan-2-carbonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(2-dipropylamino-ethyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(3-diethylamino-propyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(2-pyrrolidin-1-yl-ethyl)-piperazin-1-yl]-methanone;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N,N-dimethyl-acetamide;

[4,5-Bis-(4-chloro-phenyl)-2-(2-ethoxy-4-trifluoromethyl-phenyl)-4,5-dihydro-imidazol-1-yl]-[4-(2-methoxy-ethyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(2-diethylamino-ethyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(5-trifluoromethyl-pyridin-2-yl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(3-methoxy-propyl)-piperazin-1-yl]-methanone;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-pyrrolidin-1-yl-ethanone;

[4,5-Bis-(4-chloro-phenyl)-2-(2-ethoxy-4-trifluoromethyl-phenyl)-4,5-dihydro-imidazol-1-yl]-[4-(1-methyl-piperidin-3-ylmethyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(tetrahydro-furan-2-ylmethyl)-piperazin-1-yl]-methanone;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-nicotinonitrile;

[4,5-Bis-(4-chloro-phenyl)-2-(2-ethoxy-4-trifluoromethyl-phenyl)-4,5-dihydro-imidazol-1-yl]-(4-phenyl-piperidin-1-yl)-methanone;

[4,5-Bis-(4-chloro-phenyl)-2-(2-ethoxy-4-trifluoromethyl-phenyl)-4,5-dihydro-imidazol-1-yl]-[4-(2-piperidin-1-yl-ethyl)-piperazin-1-yl]-methanone;

4,5-Bis-(4-chloro-phenyl)-2-(2-ethoxy-4-trifluoromethyl-phenyl)-4,5-dihydro-imidazole-1-carboxylic acid (2-methoxy-ethyl)-amide;

[4,5-Bis-(4-chloro-phenyl)-2-(2-ethoxy-4-trifluoromethyl-phenyl)-4,5-dihydro-imidazol-1-yl]-(2,3,5,6-tetrahydro-[1,2']bipyrazinyl-4-yl)-methanone;

4,5-Bis-(4-chloro-phenyl)-2-(2-ethoxy-4-trifluoromethyl-phenyl)-4,5-dihydro-imidazole-1-carboxylic acid methoxy-amide;

4,5-Bis-(4-chloro-phenyl)-2-(2-ethoxy-4-trifluoromethyl-phenyl)-4,5-dihydro-imidazole-1-carboxylic acid ethoxy-amide;

4,5-Bis-(4-chloro-phenyl)-2-(2-ethoxy-4-trifluoromethyl-phenyl)-4,5-dihydro-imidazole-1-carboxylic acid (2,5-dimethoxy-phenyl)-amide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-morpholin-4-yl-ethanone;

[4,5-Bis-(4-chloro-phenyl)-2-(2-ethoxy-4-trifluoromethyl-phenyl)-4,5-dihydro-imidazol-1-yl]-[4-(3,5-dimethoxy-phenyl)-piperazin-1-yl]-methanone;

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-methoxy-ethanone hydrochloride;

[4,5-Bis-(4-chloro-phenyl)-2-(2-ethoxy-4-trifluoromethyl-phenyl)-4,5-dihydro-imidazol-1-yl]-[4-(4-fluoro-phenyl)-piperazin-1-yl]-methanone hydrochloride;

4,5-Bis-(4-chloro-phenyl)-2-(2-ethoxy-4-trifluoromethyl-phenyl)-4,5-dihydro-imidazole-1-carboxylic acid bis-(2-methoxy-ethyl)-amide;

[4,5-Bis-(4-chloro-phenyl)-2-(2-ethoxy-4-trifluoromethyl-phenyl)-4,5-dihydro-imidazol-1-yl]-[4-(4-propyl-benzenesulfonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(thiophene-2-carbonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(1,5-dimethyl-1H-pyrazole-3-carbonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(5-chloro-1,3-dimethyl-1H-pyrazole-4-sulfonyl)-piperazin-1-yl]-methanone;

Acetic acid 2-{4-[4,5-bis-(4-chloro-phenyl)-2-(2-ethoxy-4-trifluoromethyl-phenyl)-4,5-dihydro-imidazole-1-carbonyl]-piperazin-1-yl}-1,1-dimethyl-2-oxo-ethyl ester;

[4,5-Bis-(4-chloro-phenyl)-2-(2-ethoxy-4-trifluoromethyl-phenyl)-4,5-dihydro-imidazol-1-yl]-[4-(furan-3-carbonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(pyridine-4-carbonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(thiophene-3-carbonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(thiophene-2-sulfonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(4-methyl-[1,2,3]thiadiazole-5-carbonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(2,4-dimethyl-thiazole-5-sulfonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(3,5-dimethyl-isoxazole-4-carbonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(thiophene-3-sulfonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(2,5-dichloro-thiophene-3-carbonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(2,5-dimethyl-furan-3-carbonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(1,2-dimethyl-1H-imidazole-4-sulfonyl)-piperazin-1-yl]-methanone; and 1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-methoxy-ethanone.

3. A compound selected from the group consisting of:

[4,5-Bis-(4-chloro-phenyl)-2-(2-ethoxy-4-trifluoromethyl-phenyl)-4,5-dihydro-imidazol-1-yl]-[4-(2,5-dichloro-thiophene-3-sulfonyl)-piperazin-1-yl]-methanone;

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-thiophen-2-yl-ethanone;

1-(4-{4-[4,5-Bis-(4-chloro-phenyl)-2-(2-ethoxy-4-trifluoromethyl-phenyl)-4,5-dihydro-imidazole-1-carbonyl]-piperazine-1-carbonyl}-piperidin-1-yl)-ethanone;

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid dimethylamide;

[4,5-Bis-(4-chloro-phenyl)-2-(2-ethoxy-4-trifluoromethyl-phenyl)-4,5-dihydro-imidazol-1-yl]-[4-(butane-1-sulfonyl)-piperazin-1-yl]-methanone;

3-{4-[4,5-Bis-(4-chloro-phenyl)-2-(2-ethoxy-4-trifluoromethyl-phenyl)-4,5-dihydro-imidazole-1-carbonyl]-piperazine-1-sulfonyl}-thiophene-2-carboxylic acid methyl ester;

[4,5-Bis-(4-chloro-phenyl)-2-(2-ethoxy-4-trifluoromethyl-phenyl)-4,5-dihydro-imidazol-1-yl]-[4-(5-chloro-thiophene-2-sulfonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-(4-trifluoromethanesulfonyl-piperazin-1-yl)-methanone;

[4,5-Bis-(4-chloro-phenyl)-2-(2-ethoxy-4-trifluoromethyl-phenyl)-4,5-dihydro-imidazol-1-yl]-[4-(3,5-dimethyl-isoxazole-4-sulfonyl)-piperazin-1-yl]-methanone;

4-[4,5-Bis-(4-chloro-phenyl)-2-(2-ethoxy-4-trifluoromethyl-phenyl)-4,5-dihydro-imidazole-1-carbonyl]-1-(2-methoxy-ethyl)-piperazin-2-one;

4-[4,5-Bis-(4-chloro-phenyl)-2-(2-ethoxy-4-trifluoromethyl-phenyl)-4,5-dihydro-imidazole-1-carbonyl]-1-(2-morpholin-4-yl-ethyl)-piperazin-2-one hydrochloride;

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid amide;

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid methylamide;

[4,5-Bis-(4-chloro-phenyl)-2-(2-ethoxy-4-trifluoromethyl-phenyl)-4,5-dihydro-imidazol-1-yl]-[4-(pyrrolidine-1-sulfonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-[4-(piperidine-1-sulfonyl)-piperazin-1-yl]-methanone;

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid isobutyl-amide;

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid (2-methoxy-ethyl)-amide;

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid bis-(2-methoxy-ethyl)-amide;

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid (tetrahydro-furan-2-ylmethyl)-amide;

[4,5-Bis-(4-chloro-phenyl)-2-(2-ethoxy-4-trifluoromethyl-phenyl)-4,5-dihydro-imidazol-1-yl]-[4-(3-hydroxy-piperidine-1-sulfonyl)-piperazin-1-yl]-methanone;

[4,5-Bis-(4-chloro-phenyl)-2-(2-ethoxy-4-trifluoromethyl-phenyl)-4,5-dihydro-imidazol-1-yl]-{4-[4-(2-hydroxy-ethyl)-piperazine-1-sulfonyl]-piperazin-1-yl}-methanone;

1-(4-{4-[4,5-Bis-(4-chloro-phenyl)-2-(2-ethoxy-4-trifluoromethyl-phenyl)-4,5-dihydro-imidazole-1-carbonyl]-piperazine-1-sulfonyl}-piperazin-1-yl)-ethanone;

4-{4-[4,5-Bis-(4-chloro-phenyl)-2-(2-ethoxy-4-trifluoromethyl-phenyl)-4,5-dihydro-imidazole-1-carbonyl]-piperazine-1-sulfonyl}-piperazin-2-one;

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid (2-dimethylamino-ethyl)-amide;

[4,5-Bis-(4-chloro-phenyl)-2-(2-ethoxy-4-trifluoromethyl-phenyl)-4,5-dihydro-imidazol-1-yl]-[4-(4-pyrrolidin-1-yl-piperidine-1-sulfonyl)-piperazin-1-yl]-methanone;

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid (2,2,2-trifluoro-ethyl)-amide;

4-[4,5-Bis-(4-chloro-phenyl)-2-(2-ethoxy-4-trifluoromethyl-phenyl)-4,5-dihydro-imidazole-1-carbonyl]-piperazine-1-sulfonic acid (2-cyano-ethyl)-methyl-amide;

[4,5-Bis-(4-chloro-phenyl)-2-(2-ethoxy-4-trifluoromethyl-phenyl)-4,5-dihydro-imidazol-1-yl]-[4-(3,3,3-trifluoro-propyl)-piperazin-1-yl]-methanone hydrochloride;

{4-[4,5-Bis-(4-chloro-phenyl)-2-(2-ethoxy-4-trifluoromethyl-phenyl)-4,5-dihydro-imidazole-1-carbonyl]-piperazin-1-yl}-acetonitrile hydrochloride;

[4,5-Bis-(4-chloro-phenyl)-2-(2-ethoxy-4-trifluoromethyl-phenyl)-4,5-dihydro-imidazol-1-yl]-[4-(2-methoxy-ethyl)-piperazin-1-yl]-methanone hydrochloride;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(2-methoxy-1-methyl-ethyl)-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(2-methoxy-ethyl)-acetamide;

N-Benzyloxy-2-{4-[4,5-bis-(4-chloro-phenyl)-2-(2-ethoxy-4-trifluoromethyl-phenyl)-4,5-dihydro-imidazole-1-carbonyl]-piperazin-1-yl}-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-methoxy-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-ethoxy-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(5-methyl-furan-2-ylmethyl)-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-(4-trifluoromethyl-piperidin-1-yl)-ethanone;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-propyl-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-isopropyl-N-methyl-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-methoxy-N-methyl-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(2-cyano-ethyl)-N-methyl-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-cyanomethyl-N-methyl-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-(3-hydroxy-piperidin-1-yl)-ethanone;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(2-hydroxy-ethyl)-N-methyl-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-isobutyl-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N,N-bis-(2-methoxy-ethyl)-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-thiomorpholin-4-yl-ethanone;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-furan-2-ylmethyl-N-methyl-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-[1,3]dioxolan-2-ylmethyl-N-methyl-acetamide; and 1-(4-Acetyl-piperazin-1-yl)-2-{4-[4,5-bis-(4-chloro-phenyl)-2-(2-ethoxy-4-trifluoromethyl-phenyl)-4,5-dihydro-imidazole-1-carbonyl]-piperazin-1-yl}-ethanone.

4. A compound selected from the group consisting of:

1-({4-[4,5-Bis-(4-chloro-phenyl)-2-(2-ethoxy-4-trifluoromethyl-phenyl)-4,5-dihydro-imidazole-1-carbonyl]-piperazin-1-yl}-acetyl)-piperidine-3-carboxylic acid diethylamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-cyclopropyl-acetamide;

4-({4-[4,5-Bis-(4-chloro-phenyl)-2-(2-ethoxy-4-trifluoromethyl-phenyl)-4,5-dihydro-imidazole-1-carbonyl]-piperazin-1-yl}-acetyl)-piperazin-2-one;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(2,2,2-trifluoro-ethyl)-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N,N-diethyl-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(2-methyl-allyl)-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(1-hydroxymethyl-3-methyl-butyl)-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-1-[4-(2-hydroxy-ethyl)-piperidin-1-yl]-ethanone;

2-{4-[4,5-Bis-(4-chloro-phenyl)-2-(2-ethoxy-4-trifluoromethyl-phenyl)-4,5dihydro-imidazole-1-carbonyl]-piperazin-1-yl}-1-(4-hydroxymethyl-piperidin-1-yl)-ethanone;

2-{4-[4,5-Bis-(4-chloro-phenyl)-2-(2-ethoxy-4-trifluoromethyl-phenyl)-4,5dihydro-imidazole-1-carbonyl]-piperazin-1-yl}-1-(1,4-dioxa-8-aza-spiro[4.5]dec-8-yl)-ethanone;

1-({4-[4,5-Bis-(4-chloro-phenyl)-2-(2-ethoxy-4-trifluoromethyl-phenyl)-4,5-dihydro-imidazole-1-carbonyl]-piperazin-1-yl}-acetyl)-piperidine-3-carboxylic acid amide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(tetrahydro-furan-2-ylmethyl)-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-N-(3-hydroxy-propyl)-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-methyl-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(2-methoxy-1-methyl-ethyl)-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(2-methoxy-ethyl)-acetamide;

N-Benzyloxy-2-{1-[4,5-bis-(4-chloro-phenyl)-2-(2-ethoxy-4-trifluoromethyl-phenyl)-4,5-dihydro-imidazole-1-carbonyl]-piperidin-4-ylamino}-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-methoxy-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(5-methyl-furan-2-ylmethyl)-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-1-(4-trifluoromethyl-piperidin-1-yl)-ethanone;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-propyl-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-methoxy-N-methyl-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(2-cyano-ethyl)-N-methyl-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-cyanomethyl-N-methyl-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-1-(3-hydroxy-piperidin-1-yl)-ethanone;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(2-hydroxy-ethyl)-N-methyl-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-isobutyl-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(2,2,2-trifluoro-ethyl)-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(2-methyl-allyl)-acetamide;

2-{1-[4,5-Bis-(4-chloro-phenyl)-2-(2-ethoxy-4-trifluoromethyl-phenyl)-4,5-dihydro-imidazole-1-carbonyl]-piperidin-4-ylamino}-N-(1-hydroxymethyl-3-methyl-butyl)-acetamide;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-ethanesulfonic acid dimethylamide hydrochloride;

2-{4-[4,5-Bis-(4-chloro-phenyl)-2-(2-ethoxy-4-trifluoromethyl-phenyl)-4,5-dihydro-imidazole-1-carbonyl]-piperazin-1-yl}-ethanesulfonic acid amide hydrochloride;

2-(4-Acetyl-piperazin-1-yl)-N-{1-[4,5-bis-(4-chloro-phenyl)-2-(2-ethoxy-4-trifluoromethyl-phenyl)-4,5-dihydro-imidazole-1-carbonyl]-piperidin-4-yl}-acetamide;

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-(3-oxo-piperazin-1-yl)-acetamide;

1-({1-[4,5-Bis-(4-chloro-phenyl)-2-(2-ethoxy-4-trifluoromethyl-phenyl)-4,5-dihydro-imidazole-1-carbonyl]-piperidin-4-ylcarbamoyl}-methyl)-piperidine-4-carboxylic acid amide;

1-({1-[4,5-Bis-(4-chloro-phenyl)-2-(2-ethoxy-4-trifluoromethyl-phenyl)-4,5-dihydro-imidazole-1-carbonyl]-piperidin-4-ylcarbamoyl}-methyl)-piperidine-3-carboxylic acid amide;

1-({1-[4,5-Bis-(4-chloro-phenyl)-2-(2-ethoxy-4-trifluoromethyl-phenyl)-4,5-dihydro-imidazole-1-carbonyl]-piperidin-4-ylcarbamoyl}-methyl)-piperidine-3-carboxylic acid diethylamide;

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-(3-hydroxy-piperidin-1-yl)-acetamide;

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-(4-hydroxymethyl-piperidin-1-yl)-acetamide;

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-[bis-(2-hydroxy-ethyl)-amino]-acetamide;

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-(1,4-dioxa-8-aza-spiro[4.5]dec-8-yl)-acetamide;

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-[bis-(2-methoxy-ethyl)-amino]-acetamide;

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-([1,3]dioxolan-2-ylmethyl-methyl-amino)-acetamide;

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-methylamino-acetamide;

N-{1-[4,5-Bis-(4-chloro-phenyl)-2-(2-ethoxy-4-trifluoromethyl-phenyl)-4,5-dihydro-imidazole-1-carbonyl]-piperidin-4-yl}-2-dimethylamino-acetamide;

2-Amino-N-{1-[4,5-bis-(4-chloro-phenyl)-2-(2-ethoxy-4-trifluoromethyl-phenyl) -4,5-dihydro-imidazole-1-carbonyl]-piperidin-4-yl}-acetamide;

2-(4-Acetyl-piperazin-1-yl)-1-{4-[4,5-bis-(4-chloro-phenyl)-2-(2-ethoxy-4-trifluoromethyl-phenyl)-4,5-dihydro-imidazole-1-carbonyl]-piperazin-1-yl}-ethanone; and 4-(2-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-oxo-ethyl)-piperazin-2-one.

5. A compound selected from the group consisting of:

1-(2-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-oxo-ethyl)-piperidine-4-carboxylic acid amide;

1-(2-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-oxo-ethyl)-piperidine-3-carboxylic acid amide;

1-(2-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-oxo-ethyl)-piperidine-3-carboxylic acid diethylamide;

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-(2-dimethylamino-ethylamino)-ethanone;

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-[methyl-(1-methyl-pyrrolidin-3-yl)-amino]-ethanone;

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-(3-hydroxy-piperidin-1-yl)-ethanone;

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-(2-hydroxy-ethylamino)-ethanone;

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-(4-hydroxymethyl-piperidin-1-yl)-ethanone;

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-[bis-(2-hydroxy-ethyl)-amino]-ethanone;

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-(2-methoxy-ethylamino)-ethanone;

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-[bis-(2-methoxy-ethyl)-amino]-ethanone;

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-([1,3]dioxolan-2-ylmethyl-methyl-amino)-ethanone;

1-{4-[4,5-Bis-(4-chloro-phenyl)-2-(2-ethoxy-4-trifluoromethyl-phenyl)-4,5-dihydro-imidazole-1-carbonyl]-piperazin-1-yl}-2-methylamino-ethanone;

1-{1-[4,5-Bis-(4-chloro-phenyl)-2-(2-ethoxy-4-trifluoromethyl-phenyl)-4,5-dihydro-imidazole-1-carbonyl]-piperidin-4-yl}-3-methyl-thiourea;

1-{1-[4,5-Bis-(4-chloro-phenyl)-2-(2-ethoxy-4-trifluoromethyl-phenyl)-4,5-dihydro-imidazole-1-carbonyl]-piperidin-4-yl}-3-phenyl-thiourea;

4-[4,5-Bis-(4-chloro-phenyl)-2-(2-ethoxy-4-trifluoromethyl-phenyl)-4,5-dihydro-imidazole-1-carbonyl]-piperazine-1-carbothioic acid phenylamide;

1-{4-[4,5-Bis-(4-chloro-phenyl)-2-(2-ethoxy-4-trifluoromethyl-phenyl)-4,5-dihydro-imidazole-1-carbonyl]-piperazine-1-carbonyl}-piperidine-4-carboxylic acid amide;

3-Oxo-piperazine-1-carboxylic acid {1-[4,5-bis-(4-chloro-phenyl)-2-(2-ethoxy-4-trifluoromethyl-phenyl)-4,5-dihydro-imidazole-1-carbonyl]-piperidin-4-yl}-amide;

Piperidine-1,4-dicarboxylic acid 4-amide 1-({1-[4,5-bis-(4-chloro-phenyl)-2-(2-ethoxy-4-trifluoromethyl-phenyl)-4,5-dihydro-imidazole-1-carbonyl]-piperidin-4-yl}-amide);

3-{1-[4,5-Bis-(4-chloro-phenyl)-2-(2-ethoxy-4-trifluoromethyl-phenyl)-4,5-dihydro-imidazole-1-carbonyl]-piperidin-4-yl}-1,1-dimethyl-urea;

[4,5-Bis-(4-chloro-phenyl)-2-(2-ethoxy-4-trifluoromethyl-phenyl)-4,5-dihydro-imidazol-1-yl]-(4-piperazin-1-ylmethyl-piperidin-1-yl)-methanone hydrochloride;

[4,5-Bis-(4-chloro-phenyl)-2-(2-isopropoxy-4-trifluoromethyl-phenyl)-4,5-dihydro-imidazol-1-yl]-{4-[4-(2-hydroxy-ethyl)-piperazin-1-ylmethyl]-phenyl}-methanone hydrochloride;

[4,5-Bis-(4-chloro-phenyl)-2-(2-isopropoxy-4-trifluoromethyl-phenyl)-4,5-dihydro-imidazol-1-yl]-[4-(4-pyrrolidin-1-yl-piperidin-1-ylmethyl)-phenyl]-methanone hydrochloride;

[4,5-Bis-(4-chloro-phenyl)-2-(2-isopropoxy-4-trifluoromethyl-phenyl)-4,5-dihydro-imidazol-1-yl]-(4-diethylaminomethyl-phenyl)-methanone hydrochloride;

[4,5-Bis-(4-chloro-phenyl)-2-(2-isopropoxy-4-trifluoromethyl-phenyl)-4,5-dihydro-imidazol-1-yl]-(4-piperazin-1-ylmethyl-phenyl)-methanone hydrochloride;

[4-(4-Amino-piperidin-1-ylmethyl)-phenyl]-[4,5-bis-(4-chloro-phenyl)-2-(2-isopropoxy-4-trifluoromethyl-phenyl)-4,5-dihydro-imidazol-1-yl]-methanone hydrochloride;

1-(4-{4-[4,5-Bis-(4-chloro-phenyl)-2-(2-isopropoxy-4-trifluoromethyl-phenyl)-4,5-dihydro-imidazole-1-carbonyl]-benzyl}-piperazin-1-yl)-ethanone hydrochloride;

N-(1-{4-[4,5-Bis-(4-chloro-phenyl)-2-(2-isopropoxy-4-trifluoromethyl-phenyl)-4,5-dihydro-imidazole-1-carbonyl]-benzyl}-piperidin-4-yl)-acetamide hydrochloride;

4-{4-[4,5-Bis-(4-chloro-phenyl)-2-(2-isopropoxy-4-trifluoromethyl-phenyl)-4,5-dihydro-imidazole-1-carbonyl]-benzyl}-piperazin-2-one hydrochloride;

[4,5-Bis-(4-chloro-phenyl)-2-(2-isopropoxy-4-trifluoromethyl-phenyl)-4,5-dihydro-imidazol-1-yl]-[4-(2-hydroxymethyl-piperidin-1-ylmethyl)-phenyl]-methanone hydrochloride;

1-{4-[4,5-Bis-(4-chloro-phenyl)-2-(2-isopropoxy-4-trifluoromethyl-phenyl)-4,5-dihydro-imidazole-1-carbonyl]-benzyl}-pyrrolidine-2-carboxylic acid methyl ester hydrochloride;

[4,5-Bis-(4-chloro-phenyl)-2-(2-isopropoxy-4-trifluoromethyl-phenyl)-4,5-dihydro-imidazol-1-yl]-(4-morpholin-4-ylmethyl-phenyl)-methanone hydrochloride;

[4,5-Bis-(4-chloro-phenyl)-2-(2-ethoxy-5-trifluoromethyl-phenyl)-4,5-dihydro-imidazol-1-yl]-[4-(4-pyrrolidin-1-yl-piperidin-1-ylmethyl)-phenyl]-methanone hydrochloride;

[4,5-Bis-(4-chloro-phenyl)-2-(2-ethoxy-5-trifluoromethyl-phenyl)-4,5-dihydro-imidazol-1-yl]-(4-diethylaminomethyl-phenyl)-methanone hydrochloride;

4-{4-[4,5-Bis-(4-chloro-phenyl)-2-(2-ethoxy-5-trifluoromethyl-phenyl)-4,5-dihydro-imidazole-1-carbonyl]-benzyl}-piperazin-2-one hydrochloride;

[4,5-Bis-(4-chloro-phenyl)-2-(2-ethoxy-5-trifluoromethyl-phenyl)-4,5-dihydro-imidazol-1-yl]-(4-morpholin-4-ylmethyl-phenyl)-methanone;

1-{4-[4,5-Bis-(4-chloro-phenyl)-2-(2-ethoxy-5-trifluoromethyl-phenyl)-4,5-dihydro-imidazole-1-carbonyl]-benzyl}-pyrrolidine-2-carboxylic acid methyl ester hydrochloride;

4-{2-[4,5-Bis-(4-chloro-phenyl)-2-(2-ethoxy-4-trifluoromethyl-phenyl)-4,5-dihydro-imidazole-1-sulfonyl]-ethyl}-piperazin-2-one hydrochloride;

{2-[4,5-Bis-(4-chloro-phenyl)-2-(2-ethoxy-4-trifluoromethyl-phenyl)-4,5-dihydro-imidazole-1-sulfonyl]-ethyl}-diethyl-amine hydrochloride; and 2-(4-{2-[4,5-Bis-(4-chloro-phenyl)-2-(2-ethoxy-4-trifluoromethyl-phenyl)-4,5-dihydro-imidazole-1-sulfonyl]-ethyl}-piperazin-1-yl)-ethanol hydrochloride.

\* \* \* \* \*